(12) United States Patent
Afar et al.

(10) Patent No.: US 7,037,667 B1
(45) Date of Patent: May 2, 2006

(54) TUMOR ANTIGEN USEFUL IN DIAGNOSIS AND THERAPY OF PROSTATE AND COLON CANCER

(75) Inventors: Daniel E. H. Afar, Pacific Palisades, CA (US); Rene S. Hubert, Los Angeles, CA (US); Kahan Leong, Playa Del Rey, CA (US); Arthur B. Raitano, Los Angeles, CA (US); Douglas Saffran, Los Angeles, CA (US); Stephen C. Mitchell, Santa Monica, CA (US); Aya Jakobovits, Beverly Hills, CA (US); Mary Faris, Los Angeles, CA (US); Igor Vivanco, Los Angeles, CA (US)

(73) Assignee: Agensys, Inc., San Diego, CA (US)

( * ) Notice: Subject to any disclaimer, the term of this patent is extended or adjusted under 35 U.S.C. 154(b) by 100 days.

(21) Appl. No.: 09/615,285

(22) Filed: Jul. 12, 2000

Related U.S. Application Data

(63) Continuation-in-part of application No. 09/323,597, filed on Jun. 1, 1999

(60) Provisional application No. 60/129,521, filed on Apr. 14, 1999, provisional application No. 60/091,474, filed on Jun. 29, 1998, and provisional application No. 60/087,598, filed on Jun. 1, 1998.

(51) Int. Cl.
*G01N 33/574* (2006.01)
*G01N 33/48* (2006.01)
*C12Q 1/68* (2006.01)

(52) U.S. Cl. .............................. 435/7.23; 435/6; 436/64

(58) Field of Classification Search .................. 436/64; 435/6, 7.23, 7.1, 7.2, 7.4; 424/9.1
See application file for complete search history.

(56) References Cited

U.S. PATENT DOCUMENTS

| | | | |
|---|---|---|---|
| 6,043,033 A | 3/2000 | Bandman et al. .............. | 435/6 |
| 6,166,194 A * | 12/2000 | Wong et al. ................ | 536/18.7 |
| 6,262,245 B1 | 7/2001 | Xu et al. ................... | 536/23.5 |
| 6,294,663 B1 | 9/2001 | O'Brien et al. ............ | 536/23.5 |
| 6,331,427 B1 | 12/2001 | Robison ..................... | 435/226 |
| 6,350,448 B1 | 2/2002 | Bandman et al. ......... | 424/94.63 |

FOREIGN PATENT DOCUMENTS

| | | |
|---|---|---|
| EP | 1033401 | 9/2000 |
| WO | WO93/01309 | 1/1993 |
| WO | WO94/16083 | 7/1994 |
| WO | WO 98/37093 | 8/1998 |
| WO | WO 98/37418 | 8/1998 |
| WO | WO 99/62942 | 12/1999 |
| WO | WO 00/00605 | 1/2000 |
| WO | WO 00/04149 | 1/2000 |
| WO | WO 00/12758 | 3/2000 |
| WO | WO 00/18961 | 4/2000 |
| WO | WO 00/23111 | 4/2000 |
| WO | WO 00/55351 | 9/2000 |
| WO | WO 00/65067 | 11/2000 |
| WO | WO 01/22920 | 4/2001 |
| WO | WO 01/25272 | 4/2001 |
| WO | WO 01/34802 | 5/2001 |
| WO | WO 01/51633 | 7/2001 |
| WO | WO 01/57194 | 8/2001 |
| WO | WO 01/60860 | 8/2001 |
| WO | WO 01/73032 | 10/2001 |
| WO | WO 01/96538 | 12/2001 |
| WO | WO 02/04953 | 1/2002 |
| WO | WO 02/30268 | 4/2002 |

OTHER PUBLICATIONS

Wong et al. (Sequence Comparison, USPTO Protein Database, Jun. 1998).*

Afar D.E. et al. (2001). "Catalytic cleavage of the androgen–regulated TMPRSS2 protease results in its secretion by prostate and prostate cancer epithelia," *Cancer Res.* 61(4):1686–1692.

Hessels D. et al. (2004). "Applicability of biomarkers in the early diagnosis of prostate cancer," *Expert Rev. Mol. Diagn.* 4(4):513–526.

Lin B. et al. (1999). "Prostate–localized and androgen–regulated expression of the membrane–bound serine protease TMPRSS2," *Cancer Res.* 59(17):4180–4184.

(Continued)

*Primary Examiner*—Gary B. Nickol
(74) *Attorney, Agent, or Firm*—Morrison & Foerster LLP

(57) ABSTRACT

Compositions for the diagnosis and therapy of prostate and colon cancer, derived from or based on a novel prostate-specific, androgen-related, cell membrane associated and secreted serine protease termed 20P1F12/TMPRSS2 are described. A full length cDNA comprising the entire coding sequence of the 20P1F12/TMPRSS2 gene (also designated 20P1F12-GTC1 herein) is provided (FIG. 1). Among the compositions provided are antibodies that bind to 20P1F12/TMPRSS2 proteins and polypeptide fragments thereof, including antibodies labeled with a detectable marker or toxin or therapeutic composition. The invention also provides prognostic and diagnostic methods of examining a biological sample for evidence of disregulated cellular growth by comparing the status of 20P1F12/TMPRSS2 in the biological sample to the status of 20P1F12/TMPRSS2 in a corresponding normal sample, wherein alterations in the status of 20P1F12/TMPRSS2 in the biological sample are associated with disregulated cellular growth. The invention further provides various therapeutic compositions and strategies for treating prostate cancer, including particularly, 20P1F12/TMPRSS2 polypeptide and anti-20P1F12/TMPRSS2 antibody therapy methods and compositions, cancer vaccines, and small molecule therapy.

10 Claims, 38 Drawing Sheets

(1 of 38 Drawing Sheet(s) Filed in Color)

OTHER PUBLICATIONS

Paoloni–Giacobino A. et al. (2001). "Corrigenda," *Genomics* 77(1–2):114. (Correction to Paoloni–Giacobino A. et al. (1997). "Cloning of the TMPRSS2 Gene, Which Encodes a Novel Serine Protease with Transmembrane, LDLRA, and SRCR Domains and Maps to 21q22.3," *Genomics*, 44(3):309–320.)

Vaarala M.H. et al. (2001). "The TMPRSS2 gene encoding transmembrane serine protease is overexpressed in a majority of prostate cancer patients: detection of mutated TMPRSS2 form in a case of aggressive disease," *Int. J. Cancer* 94(5):705–710.

Wilson S. et al. (2004). "The membrane–anchored serine protease, TMPRSS2, activates PAR–2 in prostate cancer cells," *Biochem. J.* Nov. 10, 2004 [Epub ahead of print], located at <http://www.ncbi.nlm.nih.gov/entrez/query.fogi?cmd=Retrieve&db=pubmed&dopt=Abstract&list_uids=15537383> last visited on Dec. 1, 2004, 2 pages.

Paoloni–Giacobino, A., et al., "Cloning of the TMPRSS2 Gene, Which Encodes a Novel Serine Protease with Transmembrane, LDLRA and SRCR domains and maps to 21q22.3.", *Genomics*, vol. 44(3), 1997, pp 309–320.

Database EMBL Nucleotide and Protein Sequences, Mar. 11, 1997, XP002132696, Hinxton, GB, Abstract.

Database EMBL Nucleotide and Protein Sequences, Mar. 20, 1997, XP002132697, Hinxton, GB, Abstract.

Fair, W.R. et al., "Prostate–Specific Membrane Antigen", *Prostate*, vol. 32(2), 1997, XP–000870112, pp 140–148.

Young, Cyf et al., "Expression and Androgenic Regulation of Human Prostate–Specific Kallikreins", *Journal of Andrology*, vol. 16 (2), Apr. 1995, XP–000867297, pp. 97–99.

Tanimoto, T. et al., "Hespin, a Cell Surface Serine Protease Identified in Hepatomoa Cells, is Overexpressed in Ovarian Cancer", *Cancer Research*, vol. 57(14), Jul. 15, 1997, XP–000867297, pp. 2884–2887.

Yamamoto, M., "Raised Prostate–Specific Antigen in Adenocarcinoma of the Colon", *International Urology and Nephrology*, vol. 29(2), 1997, XP–000889898 pp. 221–225.

Database EMBL Nucleotide and Protein Sequences, Nov. 16, 1998, XP–002132700, Hinxton, GB, Abstract.

Lin, B. et al., "Prostate–localized and Androgen–regulated Expression of the Membrane–bound Serine Protease TMPRSS2[1], " *Cancer Research*, 1999, pp. 4180–4184.

Hildmann, T. et al., "A Contiguous 3–Mb Sequence–Ready Map in the S3–MX Region on 21q22.2 Based on High–Throughput Nonisotopic Library Screenings," *Genome Research*, 1999, 9:360–372.

\* cited by examiner

```
              11          20          29          38          47          56
5'  GGC GGA GGC GGA GGC GGA GGG CGA GGG GCG GGG AGC GCC GCC TGG AGC GCG GCA
    --- --- --- --- --- --- --- --- --- --- --- --- --- --- --- --- --- ---

65          74          83          92         101         110
    GGT CAT ATT GAA CAT TCC AGA TAC CTA TCA TTA CTC GAT GCT GTT GAT AAC AGC
    --- --- --- --- --- --- --- --- --- --- --- --- --- --- --- --- --- ---

119         128         137         146         155         164
    AAG ATG GCT TTG AAC TCA GGG TCA CCA CCA GCT ATT GGA CCT TAC TAT GAA AAC
    --- --- --- --- --- --- --- --- --- --- --- --- --- --- --- --- --- ---
         M   A   L   N   S   G   S   P   P   A   I   G   P   Y   Y   E   N 173         182         191         200         209         218
    CAT GGA TAC CAA CCG GAA AAC CCC TAT CCC GCA CAG CCC ACT GTG GTC CCC ACT
    --- --- --- --- --- --- --- --- --- --- --- --- --- --- --- --- --- ---
     H   G   Y   Q   P   E   N   P   Y   P   A   Q   P   T   V   V   P   T 227         236         245         254         263         272
    GTC TAC GAG GTG CAT CCG GCT CAG TAC TAC CCG TCC CCC GTG CCC CAG TAC GCC
    --- --- --- --- --- --- --- --- --- --- --- --- --- --- --- --- --- ---
     V   Y   E   V   H   P   A   Q   Y   Y   P   S   P   V   P   Q   Y   A 281         290         299         308         317         326
    CCG AGG GTC CTG ACG CAG GCT TCC AAC CCC GTC GTC TGC ACG CAG CCC AAA TCC
    --- --- --- --- --- --- --- --- --- --- --- --- --- --- --- --- --- ---
     P   R   V   L   T   Q   A   S   N   P   V   V   C   T   Q   P   K   S 335         344         353         362         371         380
    CCA TCC GGG ACA GTG TGC ACC TCA AAG ACT AAG AAA GCA CTG TGC ATC ACC TTG
    --- --- --- --- --- --- --- --- --- --- --- --- --- --- --- --- --- ---
     P   S   G   T   V   C   T   S   K   T   K   K   A   L   C   I   T   L 389         398         407         416         425         434
    ACC CTG GGG ACC TTC CTC GTG GGA GCT GCG CTG GCC GCT GGC CTA CTC TGG AAG
    --- --- --- --- --- --- --- --- --- --- --- --- --- --- --- --- --- ---
     T   L   G   T   F   L   V   G   A   A   L   A   A   G   L   L   W   K 443         452         461         470         479         488
    TTC ATG GGC AGC AAG TGC TCC AAC TCT GGG ATA GAG TGC GAC TCC TCA GGT ACC
    --- --- --- --- --- --- --- --- --- --- --- --- --- --- --- --- --- ---
     F   M   G   S   K   C   S   N   S   G   I   E   C   D   S   S   G   T 497         506         515         524         533         542
    TGC ATC AAC CCC TCT AAC TGG TGT GAT GGC GTG TCA CAC TGC CCC GGC GGG GAG
    --- --- --- --- --- --- --- --- --- --- --- --- --- --- --- --- --- ---
     C   I   N   P   S   N   W   C   D   G   V   S   H   C   P   G   G   E 551         560         569         578         587         596
    GAC GAG AAT CGG TGT GTT CGC CTC TAC GGA CCA AAC TTC ATC CTT CAG GTG TAC
    --- --- --- --- --- --- --- --- --- --- --- --- --- --- --- --- --- ---
     D   E   N   R   C   V   R   L   Y   G   P   N   F   I   L   Q   V   Y 605         614         623         632         641         650
    TCA TCT CAG AGG AAG TCC TGG CAC CCT GTG TGC CAA GAC GAC TGG AAC GAG AAC
    --- --- --- --- --- --- --- --- --- --- --- --- --- --- --- --- --- ---
     S   S   Q   R   K   S   W   H   P   V   C   Q   D   D   W   N   E   N 659         668         677         686         695         704
    TAC GGG CGG GCG GCC TGC AGG GAC ATG GGC TAT AAG AAT AAT TTT TAC TCT AGC
    --- --- --- --- --- --- --- --- --- --- --- --- --- --- --- --- --- ---
     Y   G   R   A   A   C   R   D   M   G   Y   K   N   N   F   Y   S   S
```

```
          713            722            731            740            749            758
CAA GGA ATA GTG GAT GAC AGC GGA TCC ACC AGC TTT ATG AAA CTG AAC ACA AGT
--- --- --- --- --- --- --- --- --- --- --- --- --- --- --- --- --- ---
 Q   G   I   V   D   D   S   G   S   T   S   F   M   K   L   N   T   S 767            776            785            794            803            812
GCC GGC AAT GTC GAT ATC TAT AAA AAA CTG TAC CAC AGT GAT GCC TGT TCT TCA
--- --- --- --- --- --- --- --- --- --- --- --- --- --- --- --- --- ---
 A   G   N   V   D   I   Y   K   K   L   Y   H   S   D   A   C   S   S 821            830            839            848            857            866
AAA GCA GTG GTT TCT TTA CGC TGT ATA GCC TGC GGG GTC AAC TTG AAC TCA AGC
--- --- --- --- --- --- --- --- --- --- --- --- --- --- --- --- --- ---
 K   A   V   V   S   L   R   C   I   A   C   G   V   N   L   N   S   S 875            884            893            902            911            920
CGC CAG AGC AGG ATT GTG GGC GGC GAG AGC GCG CTC CCG GGG GCC TGG CCC TGG
--- --- --- --- --- --- --- --- --- --- --- --- --- --- --- --- --- ---
 R   Q   S   R   I   V   G   G   E   S   A   L   P   G   A   W   P   W 929            938            947            956            965            974
CAG GTC AGC CTG CAC GTC CAG AAC GTC CAC GTG TGC GGA GGC TCC ATC ATC ACC
--- --- --- --- --- --- --- --- --- --- --- --- --- --- --- --- --- ---
 Q   V   S   L   H   V   Q   N   V   H   V   C   G   G   S   I   I   T 983            992           1001           1010           1019           1028
CCC GAG TGG ATC GTG ACA GCC GCC CAC TGC GTG GAA AAA CCT CTT AAC AAT CCA
--- --- --- --- --- --- --- --- --- --- --- --- --- --- --- --- --- ---
 P   E   W   I   V   T   A   A   H   C   V   E   K   P   L   N   N   P 1037           1046           1055           1064           1073           1082
TGG CAT TGG ACG GCA TTT GCG GGG ATT TTG AGA CAA TCT TTC ATG TTC TAT GGA
--- --- --- --- --- --- --- --- --- --- --- --- --- --- --- --- --- ---
 W   H   W   T   A   F   A   G   I   L   R   Q   S   F   M   F   Y   G 1091           1100           1109           1118           1127           1136
GCC GGA TAC CAA GTA GAA AAA GTG ATT TCT CAT CCA AAT TAT GAC TCC AAG ACC
--- --- --- --- --- --- --- --- --- --- --- --- --- --- --- --- --- ---
 A   G   Y   Q   V   E   K   V   I   S   H   P   N   Y   D   S   K   T 1145           1154           1163           1172           1181           1190
AAG AAC AAT GAC ATT GCG CTG ATG AAG CTG CAG AAG CCT CTG ACT TTC AAC GAC
--- --- --- --- --- --- --- --- --- --- --- --- --- --- --- --- --- ---
 K   N   N   D   I   A   L   M   K   L   Q   K   P   L   T   F   N   D 1199           1208           1217           1226           1235           1244
CTA GTG AAA CCA GTG TGT CTG CCC AAC CCA GGC ATG ATG CTG CAG CCA GAA CAG
--- --- --- --- --- --- --- --- --- --- --- --- --- --- --- --- --- ---
 L   V   K   P   V   C   L   P   N   P   G   M   M   L   Q   P   E   Q 1253           1262           1271           1280           1289           1298
CTC TGC TGG ATT TCC GGG TGG GGG GCC ACC GAG GAG AAA GGG AAG ACC TCA GAA
--- --- --- --- --- --- --- --- --- --- --- --- --- --- --- --- --- ---
 L   C   W   I   S   G   W   G   A   T   E   E   K   G   K   T   S   E 1307           1316           1325           1334           1343           1352
GTG CTG AAC GCT GCC AAG GTG CTT CTC ATT GAG ACA CAG AGA TGC AAC AGC AGA
--- --- --- --- --- --- --- --- --- --- --- --- --- --- --- --- --- ---
 V   L   N   A   A   K   V   L   L   I   E   T   Q   R   C   N   S   R 1361           1370           1379           1388           1397           1406
TAT GTC TAT GAC AAC CTG ATC ACA CCA GCC ATG ATC TGT GCC GGC TTC CTG CAG
--- --- --- --- --- --- --- --- --- --- --- --- --- --- --- --- --- ---
 Y   V   Y   D   N   L   I   T   P   A   M   I   C   A   G   F   L   Q
```

```
        1415        1424        1433        1442        1451        1460
GGG AAC GTC GAT TCT TGC CAG GGT GAC AGT GGA GGG CCT CTG GTC ACT TCG AAG
--- --- --- --- --- --- --- --- --- --- --- --- --- --- --- --- --- ---
 G   N   V   D   S   C   Q   G   D   S   G   G   P   L   V   T   S   K 1469        1478        1487        1496        1505        1514
AAC AAT ATC TGG TGG CTG ATA GGG GAT ACA AGC TGG GGT TCT GGC TGT GCC AAA
--- --- --- --- --- --- --- --- --- --- --- --- --- --- --- --- --- ---
 N   N   I   W   W   L   I   G   D   T   S   W   G   S   G   C   A   K 1523        1532        1541        1550        1559        1568
GCT TAC AGA CCA GGA GTG TAC GGG AAT GTG ATG GTA TTC ACG GAC TGG ATT TAT
--- --- --- --- --- --- --- --- --- --- --- --- --- --- --- --- --- ---
 A   Y   R   P   G   V   Y   G   N   V   M   V   F   T   D   W   I   Y 1577        1586        1595        1604        1613        1622
CGA CAA ATG AGG GCA GAC GGC TAA TCC ACA TGG TCT TCG TCC TTG ACG TCG TTT
--- --- --- --- --- --- --- --- --- --- --- --- --- --- --- --- --- ---
 R   Q   M   R   A   D   G   *

1631        1640        1649        1658        1667        1676
TAC AAG AAA ACA ATG GGG CTG GTT TTG CTT CCC CGT GCA TGA TTT ACT CTT AGA
--- --- --- --- --- --- --- --- --- --- --- --- --- --- --- --- --- ---
        1685        1694        1703        1712        1721        1730
GAT GAT TCA GAG GTC ACT TCA TTT TTA TTA AAC AGT GAA CTT GTC TGG CAA AAA
--- --- --- --- --- --- --- --- --- --- --- --- --- --- --- --- --- ---
        1739
AAA AAA AAA A 3'
--- --- --- -
```

FIG 2

```
   1 gtcatattga acattccaga tacctatcat tactcgatgc tgttgataac agcaagatgg
  61 ctttgaactc agggtcacca ccagctattg gaccttacta tgaaaccat ggataccaac
 121 cggaaaaccc ctatcccgca cagcccactg tggtccccac tgtctacgag gtgcatccgg
 181 ctcagtacta cccgtccccc gtgccccagt acgccccgag ggtcctgacg caggcttcca
 241 accccgtcgt ctgcacgcag cccaaatccc catccgggac agtgtgcacc tcaaagacta
 301 agaaagcact gtgcatcacc ttgaccctgg ggacttcct cgtgggagct gcgctggccg
 361 ctggcctact ctggaagttc atgggcagca agtgctccaa ctctgggata gagtccgact
 421 cctcaggtac ctgcatcaac ccctctaact ggtgtgatgg cgtgtcacac tgccccggcg
 481 gggaggacga aatcggtgt gttcgcctct acggaccaaa cttcatcctt cagatgtact
 541 catctcagag gaagtcctgg caccctgtgt gccaagacga ctggaacgag aactacgggc
 601 gggcggcctg cagggacatg ggctataaga ataatttta ctctagccaa ggaatagtgg
 661 atgacagcgg atccaccagc tttatgaaac tgaacacaag tgccggcaat gtcgatatct
 721 ataaaaaact gtaccacagt gatgcctgtt cttcaaaagc agtggtttct ttacgctgtt
 781 tagcctgcgg ggtcaacttg aactcaagcc gccagagcag gatcgtgggc ggtgagagcg
 841 cgctcccggg ggcctggccc tggcaggtca gcctgcacgt ccagaacgtc cacgtgtgcg
 901 gaggctccat catcaccccc gagtggatcg tgacagccgc ccactgcgtg aaaaacctc
 961 ttaacaatcc atggcattgg acggcatttg cggggatttt gagacaatct ttcatgttct
1021 atggagccgg ataccaagta caaaagtga tttctcatcc aaattatgac tccaagacca
1081 agaacaatga cattgcgctg atgaagctgc agaagcctct gactttcaac gacctagtga
1141 aaccagtgtg tctgccaac ccaggcatga tgctgcagcc agaacagctc tgctggattt
1201 ccgggtgggg ggccaccgag gagaaaggga gacctcaga agtgctgaac gctgccaagg
1261 tgcttctcat tgagacacag agatgcaaca gcagatatgt ctatgacaac ctgatcacac
1321 cagccatgat ctgtgccggc ttcctgcagg ggaacgtcga ttcttgccag ggtgacagtg
1381 gagggcctct ggtcacttcg aacaacaata tctggtggct gataggggat acaagctggg
1441 gttctggctg tgccaaagct acagaccag gagtgtacgg aatgtgatg gtattcacgg
1501 actggattta tcgacaaatg aaggcaaacg gctaatccac atggtcttcg tccttgacgt
1561 cgttttacaa gaaaacaatg gggctggttt tgcttcccg tgcatgattt actcttagag
1621 atgattcaga ggtcacttca tttttattaa acagtgaact tgtctggctt tggcactctc
1681 tgccatactg tgcaggctgc agtggctccc ctgccagcc tgctctccct aaccccttgt
1741 ccgcaagggg tgatggccgg ctggttgtgg gcactggcgg tcaattgtgg aaggaagagg
1801 gttggaggct gcccccattg agatcttcct gctgagtcct ttccaggggc caattttgga
1861 tgagcatgga gctgtcactt ctcagctgct ggatgacttg agatgaaaaa ggagagacat
1921 ggaaagggag acagccaggt ggcacctgca gcggctgccc tctggggcca cttggtagtg
1981 tcccagcct acttcacaag gggatttgc tgatgggttc ttagagcctt agcagccctg
2041 gatggtggcc agaaataaag gaccagccc ttcatgggtg gtgacgtggt agtcacttgt
2101 aagggaaca gaaacatttt tgttcttatg gggtgagaat atagacagtg cccttggtgc
2161 gagggaagca attgaaaagg aacttgccct gagcactcct ggtgcaggtc tccacctgca
2221 cattgggtgg ggctcctggg agggagactc agccttcctc ctcatcctcc ctgaccctgc
2281 tcctagcacc ctggagagtg aatgccctt ggtccctggc agggcgccaa gtttggcacc
2341 atgtcggcct cttcaggcct gatagtcatt ggaaattgag gtccatgggg gaaatcaagg
2401 atgctcagtt taaggtacac tgtttccatg ttatgtttct acacattgat ggtggtgacc
2461 ctgagttcaa agccatctt
```

ORF AMINO ACID SEQUENCE

MALNSGSPPAIGPYYENHGYQPENPYPAQPTVVPTVYEVHPAQYYPSPVPQYAPRVLTQASNPVVCTQPKSPSGTV
CTSKTKKALCITLTLGTFLVGAALAAGLLWKFMGSKCSNSGIECDSSGTCINPSNWCDGVSHCPGGEDENRCVRLY
GPNFILQMYSSQRKSWHPVCQDDWNENYGRAACRDMGYKNNFYSSQGIVDDSGSTSFMKLNTSAGNVDIYKKLYHS
DACSSKAVVSLRCLACGVNLNSSRQSRIVGGESALPGAWPWQVSLHVQNVHVCGGSIITPEWIVTAAHCVEKPLNN
PWHWTAFAGILRQSFMFYGAGYQVQKVISHPNYDSKTKNNDIALMKLQKPLTFNDLVKPVCLPNPGMMLQPEQLCW
ISGWGATEEKGKTSEVLNAAKVLLIETQRCNSRYVYDNLITPAMICAGFLQGNVDSCQGDSGGPLVTSNNNIWWLI
GDTSWGSGCAKAYRPGVYGNVMVFTDWIYRQMKANG

FIG 3A

```
          15  16                    30 31                    45 46                    60 61                    75 76                     90
GTC1          MALNSGSPPAIGPYY       ENHGYQFENPYPAQP           TVVFTVYEVHPAQYY          PSPVPQYAPRVLTQA           SNPVVCTQPKSPSGT          VCTSKTKKALCITLT   90
TMPRSS2       MALNSGSPPAIGPYY       ENIIGYQFENPYPAQP          TVVFTVYEVHPAQYY          PSPVPQYAPRVLTQA           SNPVVCTQPKSPSGT          VCTSKTKKALCITLT   90

91                   105 106                   120 121                   135 136                   150 151                   165 166                   180
GTC1          LGTFLVGAALAAGLL       WKFMGSKCSNSGIEC           DSSGTCINPSNWCDG           VSHCPGGEDENRCVR           LYGPNFILQVYSSQR           KSWHPVCQDDWNENY  180
TMPRSS2       LGTFLVGAALAAGLL       WKFMGSKCSNSGIEC           DSSGTCINPSNWCDG           VSHCPGGEDENRCVR           LYGPNFILQMYSSQR           KSWHPVCQDDWNENY  180

181                  195 196                  210 211                  225 226                  240 241                  255 256                  270
GTC1          GRAACRDMGYKNNFY       SSQGIVDDSGSTSFM           KLNTSAGNVDIYKKL           YHSDACSSKAVVSLR           CIACGVNLNSSRQSR           IVGGESALPGAWPWQ  270
TMPRSS2       GRAACRDMGYKNNFY       SSQGIVDDSGSTSFM           KLNTSAGNVDIYKKL           YHSDACSSKAVVSLR           CLACGVNLNSSRQSR           IVGGESALPGAWPWQ  270

271                  285 286                  300 301                  315 316                  330 331                  345 346                  360
GTC1          VSLHVQNVHVCGGSI       ITPEWIVTAAHCVEK           PLNNPWHWTAFAGIL           RQSFMFYGAGYQVEK           VISHPNYDSKTKNND           IALMKLQKPLTFNDL  360
TMPRSS2       VSLHVQNVHVCGGSI       ITPEWIVTAAHCVEK           PLNNPWHWTAFAGIL           RQSFMFYGAGYQVQK           VISHPNYDSKTKNND           IALMKLQKPLTTNDL  360

361                  375 376                  390 391                  405 406                  420 421                  435 436                  450
GTC1          VKPVCLPNPGMMLQP       EQLCWISGWGATEEK           GKTSEVLNAAKVLLI           TPAMICAGFLQGNVD           SCQGDSGGPLVTSKN  450
TMPRSS2       VKPVCLPNPGMMLQP       EQLCWISGWGATEEK           GKTSEVLNAAKVLLI           TPAMICAGFLQGNVD           SCQGDSGGPLVTSNN  450

451                  465 466                  480 481
GTC1          NIWWLIGDTSWGSGC       AKAYRPGVYGNVMVF           TDWIYRQMRADG              492
TMPRSS2       NIWWLIGDTSWGSGC       AKAYRPGVYGNVMVF           TDWIYRQMKANG              492
```

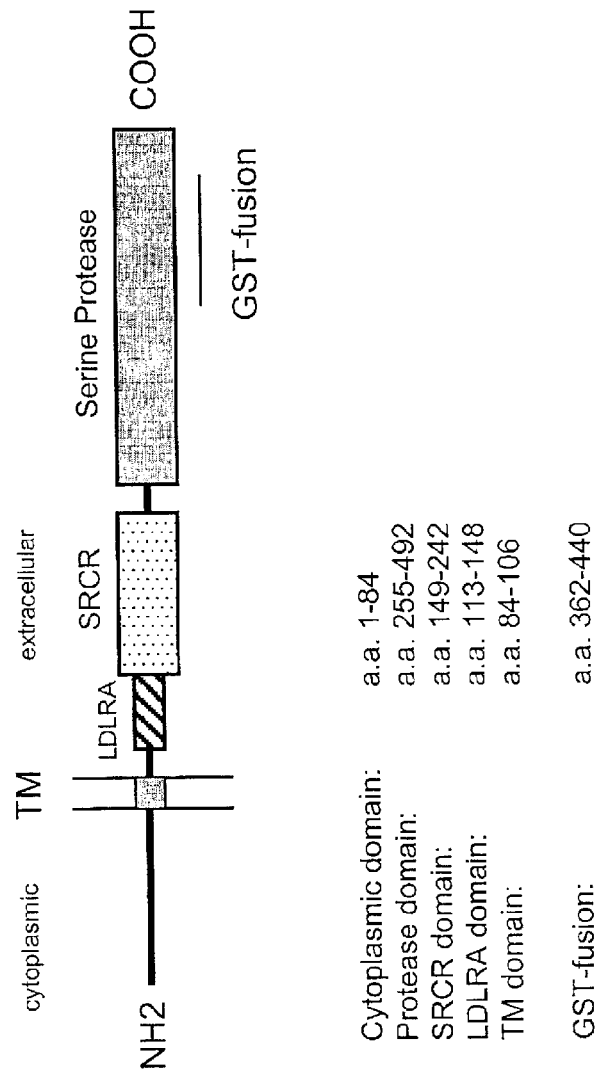

FIG 4

```
GATCTTCCTGCTGAGTCCTTTCCAGGGGCCAATTTTTGGATGAGCATGGAGCTGTCACCTCTCAGCTGCTGGATGAC
TTGAGATGAAAAAGGAGAGACATGGAAAGGGAGACAGCCAGGTGGCACCTGCAGCGGCTGCCCTCTGGGGCCACTT
GGTAGTGTCCCCAGCCTACCTCTCCACAAGGGGATTTTGCTGATGGGTTCTTANAGCCTTAGCAGCCCTGGATGGT
GGCCAGAAATAAAGGGACCAGCCCTTCATGGGTGGTGACGTGGTANTCACTTGTAAGGGGAACAGAAACATTTTTG
TTCTTATGGGGTGAGAATATAGACAGTGCCCTTGGTGCGAGGGAAGCAATTGAAAAGGAACTTGCCCTGAGCACTC
CTGGTGCA
```

A
1. Brain
2. Prostate
3. LAPC-4 AD
4. LAPC-4 AI
5. LAPC-9 AD
6. HeLa
7. Murine cDNA
8. Neg. control

B
1. Brain
2. Heart
3. Kidney
4. Liver
5. Lung
6. Pancreas
7. Placenta
8. Skeletal Muscle

C
1. Colon
2. Ovary
3. Leukocytes
4. Prostate
5. Small Intestine
6. Spleen
7. Testis
8. Thymus

- Prostate tumor pool
- Bladder tumor pool
- HeLa
- H2O
- Markers

FIG. 8

FIG. 9
A. In transfected 293T cells:
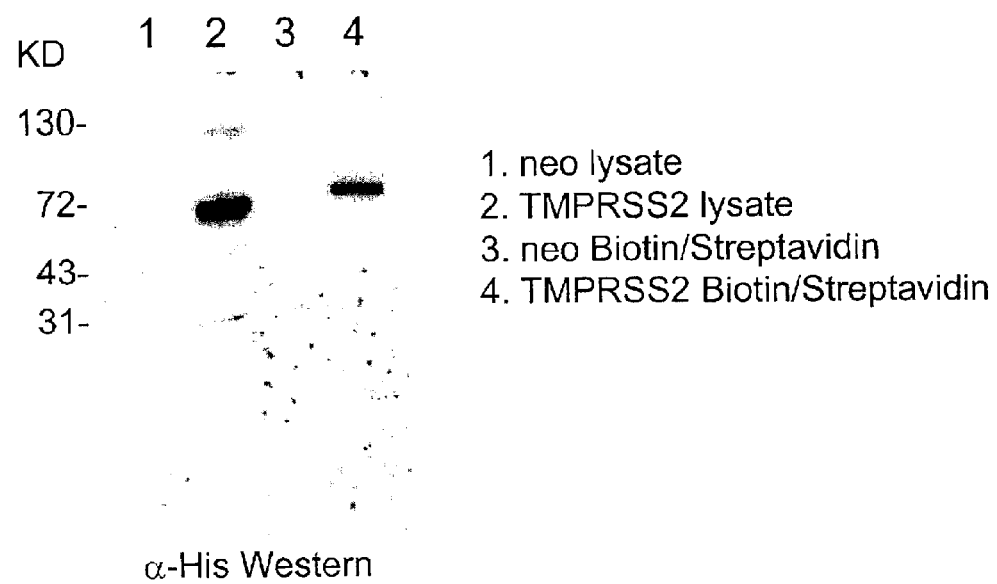
1. neo lysate
2. TMPRSS2 lysate
3. neo Biotin/Streptavidin
4. TMPRSS2 Biotin/Streptavidin
α-His Western
B. In prostate cancer cells:
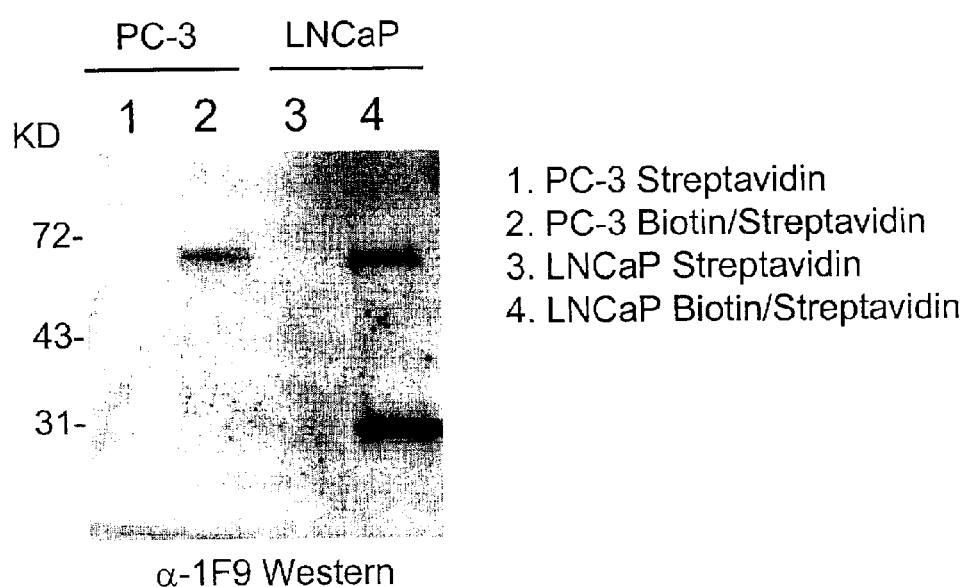
1. PC-3 Streptavidin
2. PC-3 Biotin/Streptavidin
3. LNCaP Streptavidin
4. LNCaP Biotin/Streptavidin
α-1F9 Western

Panel:

1. LNCaP androgen-deprived 1 week
2. LNCaP FBS
3. LNCaP androgen-deprived 24 hrs + mock 9 hrs
4. LNCaP androgen deprived 24 hrs + Mib 9hrs LNCaP cells were androgen deprived for 1 week (grown in 2% CS-FBS) and were then stimulated with 10 nM mibolerone for various time points FIG. 13
NIH 3T3
TMPRSS2
NIH 3T3
neo

FIG 23
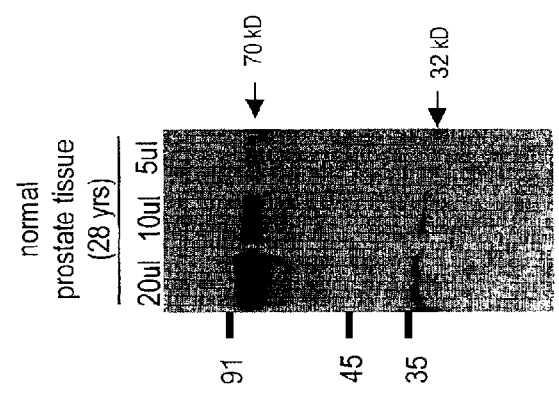
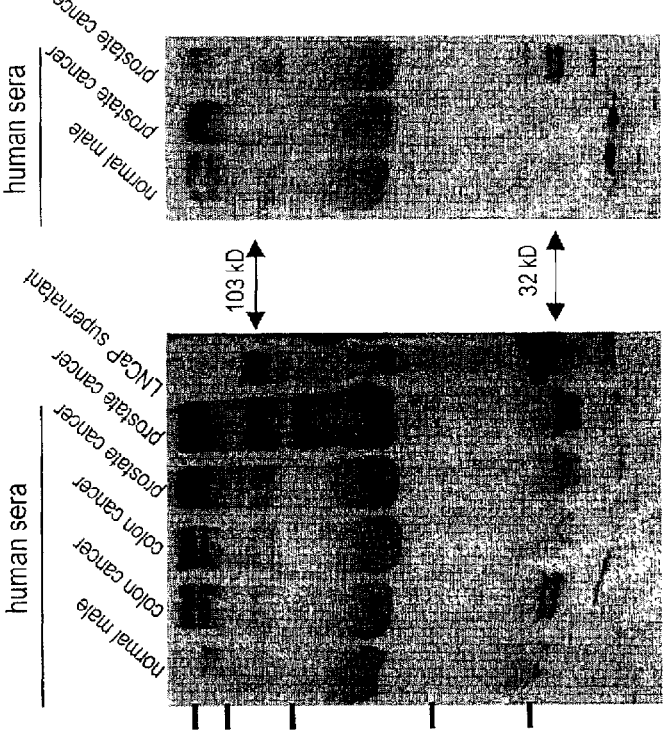
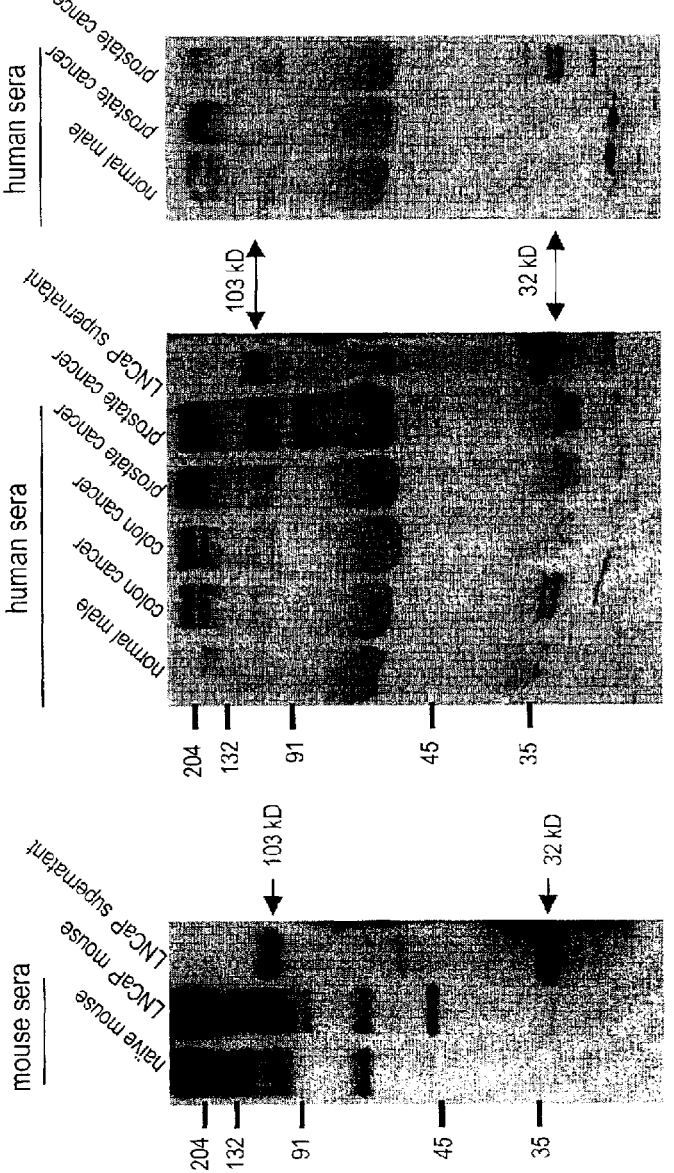
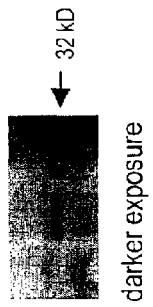

FIG 24
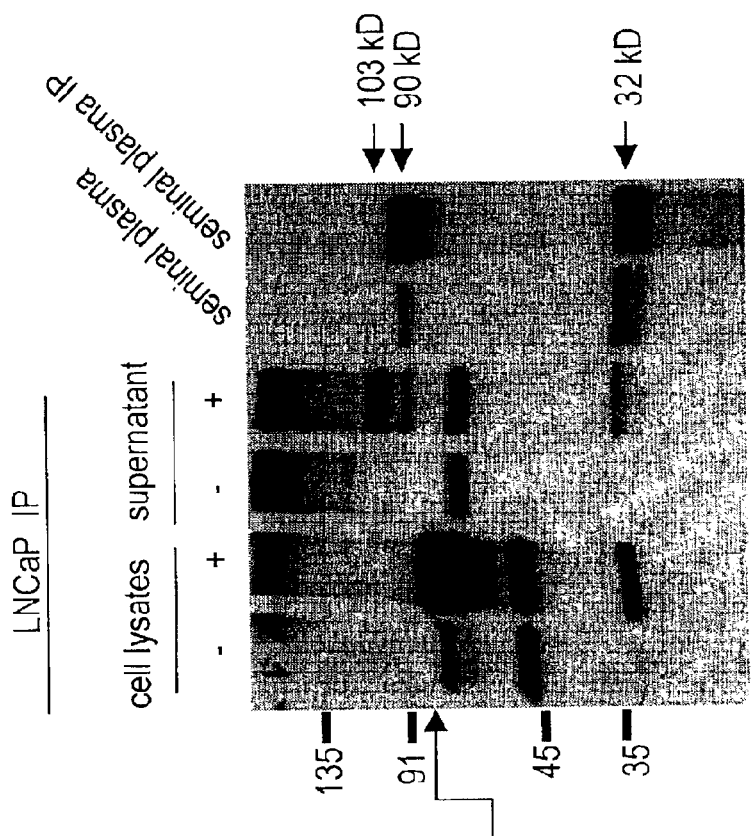
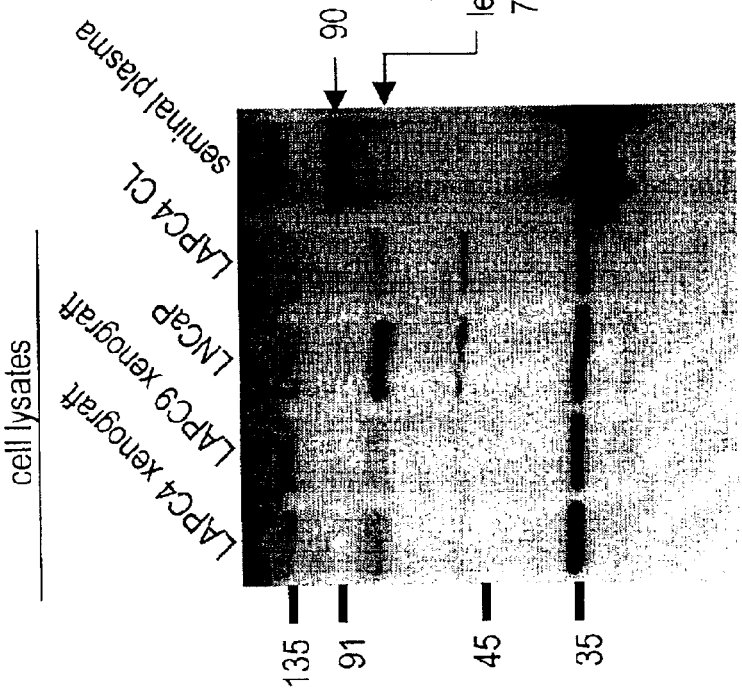

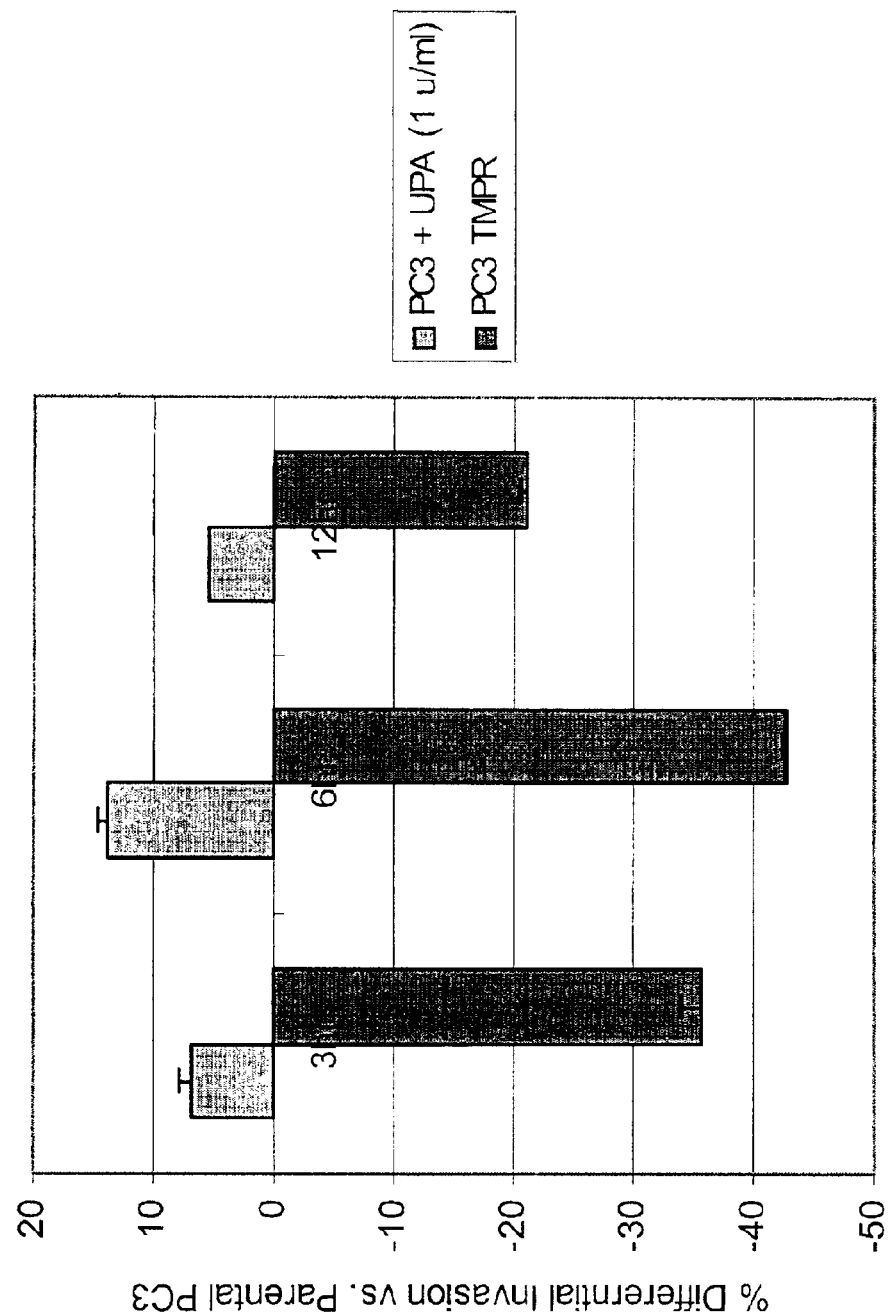

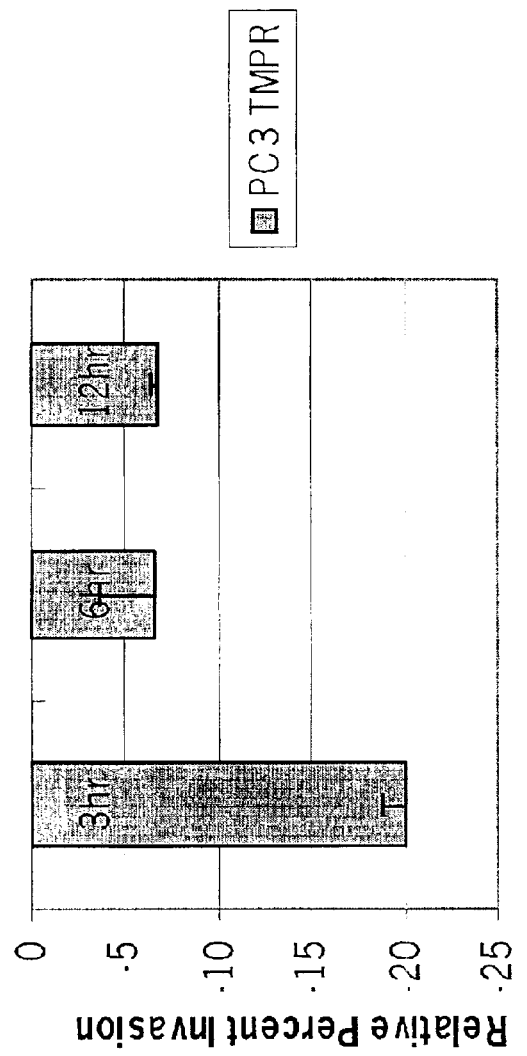

7,037,667 B1

SEQUENCE LISTING

```
<160> NUMBER OF SEQ ID NOS: 43

<210> SEQ ID NO 1
<211> LENGTH: 1738
<212> TYPE: DNA
<213> ORGANISM: Homo sapiens
<220> FEATURE:
<221> NAME/KEY: CDS
<222> LOCATION: (112)...(1588)

<400> SEQUENCE: 1
ggcggaggcg gaggcggagg gcgaggggcg gggagcgccg cctggagcgc ggcaggtcat        60
attgaacatt ccagatacct atcattactc gatgctgttg ataacagcaa g atg gct       117
                                                          Met Ala
                                                            1 ttg aac tca ggg tca cca cca gct att gga cct tac tat gaa aac cat        165
Leu Asn Ser Gly Ser Pro Pro Ala Ile Gly Pro Tyr Tyr Glu Asn His
          5                  10                  15 gga tac caa ccg gaa aac ccc tat ccc gca cag ccc act gtg gtc ccc        213
Gly Tyr Gln Pro Glu Asn Pro Tyr Pro Ala Gln Pro Thr Val Val Pro
     20                  25                  30 act gtc tac gag gtg cat ccg gct cag tac tac ccg tcc ccc gtg ccc        261
Thr Val Tyr Glu Val His Pro Ala Gln Tyr Tyr Pro Ser Pro Val Pro
 35                  40                  45                  50 cag tac gcc ccg agg gtc ctg acg cag gct tcc aac ccc gtc gtc tgc        309
Gln Tyr Ala Pro Arg Val Leu Thr Gln Ala Ser Asn Pro Val Val Cys
                 55                  60                  65 acg cag ccc aaa tcc cca tcc ggg aca gtg tgc acc tca aag act aag        357
Thr Gln Pro Lys Ser Pro Ser Gly Thr Val Cys Thr Ser Lys Thr Lys
             70                  75                  80 aaa gca ctg tgc atc acc ttg acc ctg ggg acc ttc ctc gtg gga gct        405
Lys Ala Leu Cys Ile Thr Leu Thr Leu Gly Thr Phe Leu Val Gly Ala
         85                  90                  95
```

-continued

| | |
|---|---|
| gcg ctg gcc gct ggc cta ctc tgg aag ttc atg ggc agc aag tgc tcc<br>Ala Leu Ala Ala Gly Leu Leu Trp Lys Phe Met Gly Ser Lys Cys Ser<br>100                                105                         110 | 453 |
| aac tct ggg ata gag tgc gac tcc tca ggt acc tgc atc aac ccc tct<br>Asn Ser Gly Ile Glu Cys Asp Ser Ser Gly Thr Cys Ile Asn Pro Ser<br>115                               120                       125                  130 | 501 |
| aac tgg tgt gat ggc gtg tca cac tgc ccc ggc ggg gag gac gag aat<br>Asn Trp Cys Asp Gly Val Ser His Cys Pro Gly Gly Glu Asp Glu Asn<br>                   135                       140                       145 | 549 |
| cgg tgt gtt cgc ctc tac gga cca aac ttc atc ctt cag gtg tac tca<br>Arg Cys Val Arg Leu Tyr Gly Pro Asn Phe Ile Leu Gln Val Tyr Ser<br>                  150                       155                       160 | 597 |
| tct cag agg aag tcc tgg cac cct gtg tgc caa gac gac tgg aac gag<br>Ser Gln Arg Lys Ser Trp His Pro Val Cys Gln Asp Asp Trp Asn Glu<br>165                                170                       175 | 645 |
| aac tac ggg cgg gcg gcc tgc agg gac atg ggc tat aag aat aat ttt<br>Asn Tyr Gly Arg Ala Ala Cys Arg Asp Met Gly Tyr Lys Asn Asn Phe<br>        180                       185                       190 | 693 |
| tac tct agc caa gga ata gtg gat gac agc gga tcc acc agc ttt atg<br>Tyr Ser Ser Gln Gly Ile Val Asp Asp Ser Gly Ser Thr Ser Phe Met<br>195                                200                       205                  210 | 741 |
| aaa ctg aac aca agt gcc ggc aat gtc gat atc tat aaa aaa ctg tac<br>Lys Leu Asn Thr Ser Ala Gly Asn Val Asp Ile Tyr Lys Lys Leu Tyr<br>                   215                       220                       225 | 789 |
| cac agt gat gcc tgt tct tca aaa gca gtg gtt tct tta cgc tgt ata<br>His Ser Asp Ala Cys Ser Ser Lys Ala Val Val Ser Leu Arg Cys Ile<br>                    230                       235                       240 | 837 |
| gcc tgc ggg gtc aac ttg aac tca agc cgc cag agc agg att gtg ggc<br>Ala Cys Gly Val Asn Leu Asn Ser Ser Arg Gln Ser Arg Ile Val Gly<br>                  245                       250                       255 | 885 |
| ggc gag agc gcg ctc ccg ggg gcc tgg ccc tgg cag gtc agc ctg cac<br>Gly Glu Ser Ala Leu Pro Gly Ala Trp Pro Trp Gln Val Ser Leu His<br>260                                265                       270 | 933 |
| gtc cag aac gtc cac gtg tgc gga ggc tcc atc atc acc ccc gag tgg<br>Val Gln Asn Val His Val Cys Gly Gly Ser Ile Ile Thr Pro Glu Trp<br>275                                280                       285                  290 | 981 |
| atc gtg aca gcc gcc cac tgc gtg gaa aaa cct ctt aac aat cca tgg<br>Ile Val Thr Ala Ala His Cys Val Glu Lys Pro Leu Asn Asn Pro Trp<br>                   295                       300                       305 | 1029 |
| cat tgg acg gca ttt gcg ggg att ttg aga caa tct ttc atg ttc tat<br>His Trp Thr Ala Phe Ala Gly Ile Leu Arg Gln Ser Phe Met Phe Tyr<br>                    310                       315                       320 | 1077 |
| gga gcc gga tac caa gta gaa aaa gtg att tct cat cca aat tat gac<br>Gly Ala Gly Tyr Gln Val Glu Lys Val Ile Ser His Pro Asn Tyr Asp<br>325                                330                       335 | 1125 |
| tcc aag acc aag aac aat gac att gcg ctg atg aag ctg cag aag cct<br>Ser Lys Thr Lys Asn Asn Asp Ile Ala Leu Met Lys Leu Gln Lys Pro<br>340                                345                       350 | 1173 |
| ctg act ttc aac gac cta gtg aaa cca gtg tgt ctg ccc aac cca ggc<br>Leu Thr Phe Asn Asp Leu Val Lys Pro Val Cys Leu Pro Asn Pro Gly<br>355                                360                       365                  370 | 1221 |
| atg atg ctg cag cca gaa cag ctc tgc tgg att tcc ggg tgg ggg gcc<br>Met Met Leu Gln Pro Glu Gln Leu Cys Trp Ile Ser Gly Trp Gly Ala<br>                    375                       380                       385 | 1269 |
| acc gag gag aaa ggg aag acc tca gaa gtg ctg aac gct gcc aag gtg<br>Thr Glu Glu Lys Gly Lys Thr Ser Glu Val Leu Asn Ala Ala Lys Val<br>                   390                       395                       400 | 1317 |
| ctt ctc att gag aca cag aga tgc aac agc aga tat gtc tat gac aac<br>Leu Leu Ile Glu Thr Gln Arg Cys Asn Ser Arg Tyr Val Tyr Asp Asn<br>405                                410                       415 | 1365 |

| | | | | | | | | | | | | | | | | |
|---|---|---|---|---|---|---|---|---|---|---|---|---|---|---|---|---|
| ctg | atc | aca | cca | gcc | atg | atc | tgt | gcc | ggc | ttc | ctg | cag | ggg | aac | gtc | 1413 |
| Leu | Ile | Thr | Pro | Ala | Met | Ile | Cys | Ala | Gly | Phe | Leu | Gln | Gly | Asn | Val | |
| | 420 | | | | | 425 | | | | | 430 | | | | | |
| gat | tct | tgc | cag | ggt | gac | agt | gga | ggg | cct | ctg | gtc | act | tcg | aag | aac | 1461 |
| Asp | Ser | Cys | Gln | Gly | Asp | Ser | Gly | Gly | Pro | Leu | Val | Thr | Ser | Lys | Asn | |
| 435 | | | | | 440 | | | | | 445 | | | | | 450 | |
| aat | atc | tgg | tgg | ctg | ata | ggg | gat | aca | agc | tgg | ggt | tct | ggc | tgt | gcc | 1509 |
| Asn | Ile | Trp | Trp | Leu | Ile | Gly | Asp | Thr | Ser | Trp | Gly | Ser | Gly | Cys | Ala | |
| | | | 455 | | | | | 460 | | | | | 465 | | | |
| aaa | gct | tac | aga | cca | gga | gtg | tac | ggg | aat | gtg | atg | gta | ttc | acg | gac | 1557 |
| Lys | Ala | Tyr | Arg | Pro | Gly | Val | Tyr | Gly | Asn | Val | Met | Val | Phe | Thr | Asp | |
| | | 470 | | | | | 475 | | | | | 480 | | | | |

| | | | | | | | | | | |
|---|---|---|---|---|---|---|---|---|---|---|
| tgg | att | tat | cga | caa | atg | agg | gca | gac | ggc | t aatccacatg gtcttcgtcc | 1608 |
| Trp | Ile | Tyr | Arg | Gln | Met | Arg | Ala | Asp | Gly | |
| | 485 | | | | | 490 | | | | |

| | | |
|---|---|---|
| ttgacgtcgt tttacaagaa aacaatgggg ctggttttgc ttccccgtgc atgatttact | 1668 |
| cttagagatg attcagaggt cacttcattt ttattaaaca gtgaacttgt ctggcaaaaa | 1728 |
| aaaaaaaaaa | 1738 |

<210> SEQ ID NO 2
<211> LENGTH: 492
<212> TYPE: PRT
<213> ORGANISM: Homo sapiens

<400> SEQUENCE: 2

Met Ala Leu Asn Ser Gly Ser Pro Pro Ala Ile Gly Pro Tyr Tyr Glu
1               5                   10                  15

Asn His Gly Tyr Gln Pro Glu Asn Pro Tyr Pro Ala Gln Pro Thr Val
                20                  25                  30

Val Pro Thr Val Tyr Glu Val His Pro Ala Gln Tyr Tyr Pro Ser Pro
            35                  40                  45

Val Pro Gln Tyr Ala Pro Arg Val Leu Thr Gln Ala Ser Asn Pro Val
        50                  55                  60

Val Cys Thr Gln Pro Lys Ser Pro Ser Gly Thr Val Cys Thr Ser Lys
65                  70                  75                  80

Thr Lys Lys Ala Leu Cys Ile Thr Leu Thr Leu Gly Thr Phe Leu Val
                85                  90                  95

Gly Ala Ala Leu Ala Ala Gly Leu Leu Trp Lys Phe Met Gly Ser Lys
            100                 105                 110

Cys Ser Asn Ser Gly Ile Glu Cys Asp Ser Ser Gly Thr Cys Ile Asn
        115                 120                 125

Pro Ser Asn Trp Cys Asp Gly Val Ser His Cys Pro Gly Gly Glu Asp
    130                 135                 140

Glu Asn Arg Cys Val Arg Leu Tyr Gly Pro Asn Phe Ile Leu Gln Val
145                 150                 155                 160

Tyr Ser Ser Gln Arg Lys Ser Trp His Pro Val Cys Gln Asp Asp Trp
                165                 170                 175

Asn Glu Asn Tyr Gly Arg Ala Ala Cys Arg Asp Met Gly Tyr Lys Asn
            180                 185                 190

Asn Phe Tyr Ser Ser Gln Gly Ile Val Asp Asp Ser Gly Ser Thr Ser
        195                 200                 205

Phe Met Lys Leu Asn Thr Ser Ala Gly Asn Val Asp Ile Tyr Lys Lys
    210                 215                 220

Leu Tyr His Ser Asp Ala Cys Ser Ser Lys Ala Val Val Ser Leu Arg
225                 230                 235                 240

```
Cys Ile Ala Cys Gly Val Asn Leu Asn Ser Ser Arg Gln Ser Arg Ile
                245                 250                 255
Val Gly Gly Glu Ser Ala Leu Pro Gly Ala Trp Pro Trp Gln Val Ser
            260                 265                 270
Leu His Val Gln Asn Val His Val Cys Gly Gly Ser Ile Ile Thr Pro
        275                 280                 285
Glu Trp Ile Val Thr Ala Ala His Cys Val Glu Lys Pro Leu Asn Asn
    290                 295                 300
Pro Trp His Trp Thr Ala Phe Ala Gly Ile Leu Arg Gln Ser Phe Met
305                 310                 315                 320
Phe Tyr Gly Ala Gly Tyr Gln Val Glu Lys Val Ile Ser His Pro Asn
                325                 330                 335
Tyr Asp Ser Lys Thr Lys Asn Asn Asp Ile Ala Leu Met Lys Leu Gln
            340                 345                 350
Lys Pro Leu Thr Phe Asn Asp Leu Val Lys Pro Val Cys Leu Pro Asn
        355                 360                 365
Pro Gly Met Met Leu Gln Pro Glu Gln Leu Cys Trp Ile Ser Gly Trp
    370                 375                 380
Gly Ala Thr Glu Glu Lys Gly Lys Thr Ser Glu Val Leu Asn Ala Ala
385                 390                 395                 400
Lys Val Leu Leu Ile Glu Thr Gln Arg Cys Asn Ser Arg Tyr Val Tyr
                405                 410                 415
Asp Asn Leu Ile Thr Pro Ala Met Ile Cys Ala Gly Phe Leu Gln Gly
            420                 425                 430
Asn Val Asp Ser Cys Gln Gly Asp Ser Gly Gly Pro Leu Val Thr Ser
        435                 440                 445
Lys Asn Asn Ile Trp Trp Leu Ile Gly Asp Thr Ser Trp Gly Ser Gly
    450                 455                 460
Cys Ala Lys Ala Tyr Arg Pro Gly Val Tyr Gly Asn Val Met Val Phe
465                 470                 475                 480
Thr Asp Trp Ile Tyr Arg Gln Met Arg Ala Asp Gly
                485                 490

<210> SEQ ID NO 3
<211> LENGTH: 2479
<212> TYPE: DNA
<213> ORGANISM: Homo sapiens
<220> FEATURE:
<221> NAME/KEY: CDS
<222> LOCATION: (57)...(1534)

<400> SEQUENCE: 3
gtcatattga acattccaga tacctatcat tactcgatgc tgttgataac agcaag atg     59
                                                                Met
                                                                  1 gct ttg aac tca ggg tca cca cca gct att gga cct tac tat gaa aac    107
Ala Leu Asn Ser Gly Ser Pro Pro Ala Ile Gly Pro Tyr Tyr Glu Asn
            5                  10                  15 cat gga tac caa ccg gaa aac ccc tat ccc gca cag ccc act gtg gtc    155
His Gly Tyr Gln Pro Glu Asn Pro Tyr Pro Ala Gln Pro Thr Val Val
         20                  25                  30 ccc act gtc tac gag gtg cat ccg gct cag tac tac ccg tcc ccc gtg    203
Pro Thr Val Tyr Glu Val His Pro Ala Gln Tyr Tyr Pro Ser Pro Val
     35                  40                  45 ccc cag tac gcc ccg agg gtc ctg acg cag gct tcc aac ccc gtc gtc    251
Pro Gln Tyr Ala Pro Arg Val Leu Thr Gln Ala Ser Asn Pro Val Val
 50                  55                  60                  65
```

-continued

```
tgc acg cag ccc aaa tcc cca tcc ggg aca gtg tgc acc tca aag act          299
Cys Thr Gln Pro Lys Ser Pro Ser Gly Thr Val Cys Thr Ser Lys Thr
             70                  75                  80 aag aaa gca ctg tgc atc acc ttg acc ctg ggg acc ttc ctc gtg gga          347
Lys Lys Ala Leu Cys Ile Thr Leu Thr Leu Gly Thr Phe Leu Val Gly
             85                  90                  95 gct gcg ctg gcc gct ggc cta ctc tgg aag ttc atg ggc agc aag tgc          395
Ala Ala Leu Ala Ala Gly Leu Leu Trp Lys Phe Met Gly Ser Lys Cys
            100                 105                 110 tcc aac tct ggg ata gag tgc gac tcc tca ggt acc tgc atc aac ccc          443
Ser Asn Ser Gly Ile Glu Cys Asp Ser Ser Gly Thr Cys Ile Asn Pro
        115                 120                 125 tct aac tgg tgt gat ggc gtg tca cac tgc ccc ggc ggg gag gac gag          491
Ser Asn Trp Cys Asp Gly Val Ser His Cys Pro Gly Gly Glu Asp Glu
130                 135                 140                 145 aat cgg tgt gtt cgc ctc tac gga cca aac ttc atc ctt cag atg tac          539
Asn Arg Cys Val Arg Leu Tyr Gly Pro Asn Phe Ile Leu Gln Met Tyr
                150                 155                 160 tca tct cag agg aag tcc tgg cac cct gtg tgc caa gac gac tgg aac          587
Ser Ser Gln Arg Lys Ser Trp His Pro Val Cys Gln Asp Asp Trp Asn
            165                 170                 175 gag aac tac ggg cgg gcg gcc tgc agg gac atg ggc tat aag aat aat          635
Glu Asn Tyr Gly Arg Ala Ala Cys Arg Asp Met Gly Tyr Lys Asn Asn
        180                 185                 190 ttt tac tct agc caa gga ata gtg gat gac agc gga tcc acc agc ttt          683
Phe Tyr Ser Ser Gln Gly Ile Val Asp Asp Ser Gly Ser Thr Ser Phe
    195                 200                 205 atg aaa ctg aac aca agt gcc ggc aat gtc gat atc tat aaa aaa ctg          731
Met Lys Leu Asn Thr Ser Ala Gly Asn Val Asp Ile Tyr Lys Lys Leu
210                 215                 220                 225 tac cac agt gat gcc tgt tct tca aaa gca gtg gtt tct tta cgc tgt          779
Tyr His Ser Asp Ala Cys Ser Ser Lys Ala Val Val Ser Leu Arg Cys
                230                 235                 240 tta gcc tgc ggg gtc aac ttg aac tca agc cgc cag agc agg atc gtg          827
Leu Ala Cys Gly Val Asn Leu Asn Ser Ser Arg Gln Ser Arg Ile Val
            245                 250                 255 ggc ggt gag agc gcg ctc ccg ggg gcc tgg ccc tgg cag gtc agc ctg          875
Gly Gly Glu Ser Ala Leu Pro Gly Ala Trp Pro Trp Gln Val Ser Leu
        260                 265                 270 cac gtc cag aac gtc cac gtg tgc gga ggc tcc atc atc acc ccc gag          923
His Val Gln Asn Val His Val Cys Gly Gly Ser Ile Ile Thr Pro Glu
    275                 280                 285 tgg atc gtg aca gcc gcc cac tgc gtg gaa aaa cct ctt aac aat cca          971
Trp Ile Val Thr Ala Ala His Cys Val Glu Lys Pro Leu Asn Asn Pro
290                 295                 300                 305 tgg cat tgg acg gca ttt gcg ggg att ttg aga caa tct ttc atg ttc         1019
Trp His Trp Thr Ala Phe Ala Gly Ile Leu Arg Gln Ser Phe Met Phe
                310                 315                 320 tat gga gcc gga tac caa gta caa aaa gtg att tct cat cca aat tat         1067
Tyr Gly Ala Gly Tyr Gln Val Gln Lys Val Ile Ser His Pro Asn Tyr
            325                 330                 335 gac tcc aag acc aag aac aat gac att gcg ctg atg aag ctg cag aag         1115
Asp Ser Lys Thr Lys Asn Asn Asp Ile Ala Leu Met Lys Leu Gln Lys
        340                 345                 350 cct ctg act ttc aac gac cta gtg aaa cca gtg tgt ctg ccc aac cca         1163
Pro Leu Thr Phe Asn Asp Leu Val Lys Pro Val Cys Leu Pro Asn Pro
    355                 360                 365 ggc atg atg ctg cag cca gaa cag ctc tgc tgg att tcc ggg tgg ggg         1211
Gly Met Met Leu Gln Pro Glu Gln Leu Cys Trp Ile Ser Gly Trp Gly
```

```
                370             375             380             385
gcc acc gag gag aaa ggg aag acc tca gaa gtg ctg aac gct gcc aag      1259
Ala Thr Glu Glu Lys Gly Lys Thr Ser Glu Val Leu Asn Ala Ala Lys
                    390             395             400 gtg ctt ctc att gag aca cag aga tgc aac agc aga tat gtc tat gac      1307
Val Leu Leu Ile Glu Thr Gln Arg Cys Asn Ser Arg Tyr Val Tyr Asp
                405             410             415 aac ctg atc aca cca gcc atg atc tgt gcc ggc ttc ctg cag ggg aac      1355
Asn Leu Ile Thr Pro Ala Met Ile Cys Ala Gly Phe Leu Gln Gly Asn
            420             425             430 gtc gat tct tgc cag ggt gac agt gga ggg cct ctg gtc act tcg aac      1403
Val Asp Ser Cys Gln Gly Asp Ser Gly Gly Pro Leu Val Thr Ser Asn
        435             440             445 aac aat atc tgg tgg ctg ata ggg gat aca agc tgg ggt tct ggc tgt      1451
Asn Asn Ile Trp Trp Leu Ile Gly Asp Thr Ser Trp Gly Ser Gly Cys
450             455             460             465 gcc aaa gct tac aga cca gga gtg tac ggg aat gtg atg gta ttc acg      1499
Ala Lys Ala Tyr Arg Pro Gly Val Tyr Gly Asn Val Met Val Phe Thr
                470             475             480 gac tgg att tat cga caa atg aag gca aac ggc ta atccacatgg            1544
Asp Trp Ile Tyr Arg Gln Met Lys Ala Asn Gly
                485             490 tcttcgtcct tgacgtcgtt ttacaagaaa acaatgggc tggttttgct tccccgtgca     1604
tgatttactc ttagagatga ttcagaggtc acttcatttt tattaaacag tgaacttgtc    1664
tggctttggc actctctgcc atactgtgca ggctgcagtg gctcccctgc ccagcctgct    1724
ctccctaacc ccttgtccgc aagggtgat ggccggctgg ttgtgggcac tggcggtcaa     1784
ttgtggaagg aagagggttg gaggctgccc ccattgagat cttcctgctg agtccttccc    1844
aggggccaat tttggatgag catggagctg tcacttctca gctgctggat gacttgagat    1904
gaaaaaggag agacatggaa agggagacag ccaggtggca cctgcagcgg ctgccctctg    1964
gggccacttg gtagtgtccc cagcctactt cacaagggga ttttgctgat gggttcttag    2024
agccttagca gccctggatg gtggccagaa ataaagggac cagcccttca tgggtggtga    2084
cgtggtagtc acttgtaagg ggaacagaaa cattttttgtt cttatggggt gagaatatag   2144
acagtgccct tggtgcgagg gaagcaattg aaaaggaact tgccctgagc actcctggtg    2204
caggtctcca cctgcacatt gggtggggct cctgggaggg agactcagcc ttcctcctca    2264
tcctccctga ccctgctcct agcaccctgg agagtgaatg cccccttggtc cctggcaggg   2324
cgccaagttt ggcaccatgt cggcctcttc aggcctgata gtcattggaa attgaggtcc    2384
atggggaaa tcaaggatgc tcagtttaag gtacactgtt tccatgttat gtttctacac     2444
attgatggtg gtgaccctga gttcaaagcc atctt                               2479
```

<210> SEQ ID NO 4
<211> LENGTH: 492
<212> TYPE: PRT
<213> ORGANISM: Homo sapiens

<400> SEQUENCE: 4

```
Met Ala Leu Asn Ser Gly Ser Pro Ala Ile Gly Pro Tyr Tyr Glu
1               5                   10                  15

Asn His Gly Tyr Gln Pro Glu Asn Pro Tyr Pro Ala Gln Pro Thr Val
                20              25                  30

Val Pro Thr Val Tyr Glu Val His Pro Ala Gln Tyr Tyr Pro Ser Pro
            35              40                  45
```

```
Val Pro Gln Tyr Ala Pro Arg Val Leu Thr Gln Ala Ser Asn Pro Val
 50                  55                  60

Val Cys Thr Gln Pro Lys Ser Pro Ser Gly Thr Val Cys Thr Ser Lys
 65                  70                  75                  80

Thr Lys Lys Ala Leu Cys Ile Thr Leu Thr Leu Gly Thr Phe Leu Val
                 85                  90                  95

Gly Ala Ala Leu Ala Ala Gly Leu Leu Trp Lys Phe Met Gly Ser Lys
            100                 105                 110

Cys Ser Asn Ser Gly Ile Glu Cys Asp Ser Ser Gly Thr Cys Ile Asn
            115                 120                 125

Pro Ser Asn Trp Cys Asp Gly Val Ser His Cys Pro Gly Gly Glu Asp
            130                 135                 140

Glu Asn Arg Cys Val Arg Leu Tyr Gly Pro Asn Phe Ile Leu Gln Met
145                 150                 155                 160

Tyr Ser Ser Gln Arg Lys Ser Trp His Pro Val Cys Gln Asp Asp Trp
                165                 170                 175

Asn Glu Asn Tyr Gly Arg Ala Ala Cys Arg Asp Met Gly Tyr Lys Asn
                180                 185                 190

Asn Phe Tyr Ser Ser Gln Gly Ile Val Asp Asp Ser Gly Ser Thr Ser
                195                 200                 205

Phe Met Lys Leu Asn Thr Ser Ala Gly Asn Val Asp Ile Tyr Lys Lys
            210                 215                 220

Leu Tyr His Ser Asp Ala Cys Ser Ser Lys Ala Val Val Ser Leu Arg
225                 230                 235                 240

Cys Leu Ala Cys Gly Val Asn Leu Asn Ser Ser Arg Gln Ser Arg Ile
                245                 250                 255

Val Gly Gly Glu Ser Ala Leu Pro Gly Ala Trp Pro Trp Gln Val Ser
            260                 265                 270

Leu His Val Gln Asn Val His Val Cys Gly Gly Ser Ile Ile Thr Pro
            275                 280                 285

Glu Trp Ile Val Thr Ala Ala His Cys Val Glu Lys Pro Leu Asn Asn
290                 295                 300

Pro Trp His Trp Thr Ala Phe Ala Gly Ile Leu Arg Gln Ser Phe Met
305                 310                 315                 320

Phe Tyr Gly Ala Gly Tyr Gln Val Gln Lys Val Ile Ser His Pro Asn
                325                 330                 335

Tyr Asp Ser Lys Thr Lys Asn Asn Asp Ile Ala Leu Met Lys Leu Gln
            340                 345                 350

Lys Pro Leu Thr Phe Asn Asp Leu Val Lys Pro Val Cys Leu Pro Asn
            355                 360                 365

Pro Gly Met Met Leu Gln Pro Glu Gln Leu Cys Trp Ile Ser Gly Trp
            370                 375                 380

Gly Ala Thr Glu Glu Lys Gly Lys Thr Ser Glu Val Leu Asn Ala Ala
385                 390                 395                 400

Lys Val Leu Leu Ile Glu Thr Gln Arg Cys Asn Ser Arg Tyr Val Tyr
                405                 410                 415

Asp Asn Leu Ile Thr Pro Ala Met Ile Cys Ala Gly Phe Leu Gln Gly
            420                 425                 430

Asn Val Asp Ser Cys Gln Gly Asp Ser Gly Gly Pro Leu Val Thr Ser
            435                 440                 445

Asn Asn Asn Ile Trp Trp Leu Ile Gly Asp Thr Ser Trp Gly Ser Gly
            450                 455                 460

Cys Ala Lys Ala Tyr Arg Pro Gly Val Tyr Gly Asn Val Met Val Phe
```

465              470              475              480

Thr Asp Trp Ile Tyr Arg Gln Met Lys Ala Asn Gly
                485              490

<210> SEQ ID NO 5
<211> LENGTH: 388
<212> TYPE: DNA
<213> ORGANISM: Homo Sapiens
<220> FEATURE:
<221> NAME/KEY: misc_feature
<222> LOCATION: (1)...(388)
<223> OTHER INFORMATION: n = A,T,C or G

<400> SEQUENCE: 5
gatcttcctg ctgagtcctt tccaggggcc aattttggat gagcatggag ctgtcacctc    60
tcagctgctg gatgacttga gatgaaaaag gagagacatg gaaagggaga cagccaggtg   120
gcacctgcag cggctgccct ctggggccac ttggtagtgt ccccagccta cctctccaca   180
aggggatttt gctgatgggt tcttanagcc ttagcagccc tggatggtgg ccagaaataa   240
agggaccagc ccttcatggg tggtgacgtg gtantcactt gtaagggaa cagaaacatt    300 tttgttctta tggggtgaga atatagacag tgcccttggt gcgagggaag caattgaaaa   360
ggaacttgcc ctgagcactc ctggtgca                                      388

<210> SEQ ID NO 6
<211> LENGTH: 14
<212> TYPE: DNA
<213> ORGANISM: Artificial Sequence
<220> FEATURE:
<223> OTHER INFORMATION: cDNA Synthesis Primer

<400> SEQUENCE: 6
ttttgtacaa gctt                                                      14

<210> SEQ ID NO 7
<211> LENGTH: 44
<212> TYPE: DNA
<213> ORGANISM: Artificial Sequence
<220> FEATURE:
<223> OTHER INFORMATION: DNA Adaptor 1

<400> SEQUENCE: 7
ctaatacgac tcactatagg gctcgagcgg ccgcccgggc aggt                      44

<210> SEQ ID NO 8
<211> LENGTH: 42
<212> TYPE: DNA
<213> ORGANISM: Artificial Sequence
<220> FEATURE:
<223> OTHER INFORMATION: DNA Adaptor 2

<400> SEQUENCE: 8
gtaatacgac tcactatagg gcagcgtggt cgcggccgag gt                        42

<210> SEQ ID NO 9
<211> LENGTH: 22
<212> TYPE: DNA
<213> ORGANISM: Artificial Sequence
<220> FEATURE:
<223> OTHER INFORMATION: PCR Primer 1

<400> SEQUENCE: 9
ctaatacgac tcactatagg gc                                              22

```
<210> SEQ ID NO 10
<211> LENGTH: 22
<212> TYPE: DNA
<213> ORGANISM: Artificial Sequence
<220> FEATURE:
<223> OTHER INFORMATION: Nester PCR Primer (NP) 1

<400> SEQUENCE: 10
tcgagcggcc gcccgggcag gt                                              22

<210> SEQ ID NO 11
<211> LENGTH: 20
<212> TYPE: DNA
<213> ORGANISM: Artificial Sequence
<220> FEATURE:
<223> OTHER INFORMATION: Nester PCR Primer (NP) 2

<400> SEQUENCE: 11
agcgtggtcg cggccgaggt                                                 20

<210> SEQ ID NO 12
<211> LENGTH: 23
<212> TYPE: DNA
<213> ORGANISM: Artificial Sequence
<220> FEATURE:
<223> OTHER INFORMATION: RT-PCR Primer 1A

<400> SEQUENCE: 12
agtcttcctg ctgagtcctt tcc                                             23

<210> SEQ ID NO 13
<211> LENGTH: 25
<212> TYPE: DNA
<213> ORGANISM: Artificial Sequence
<220> FEATURE:
<223> OTHER INFORMATION: RT-PCR Primer 1B

<400> SEQUENCE: 13
caagggcact gtctatattc tcacc                                           25

<210> SEQ ID NO 14
<211> LENGTH: 10
<212> TYPE: DNA
<213> ORGANISM: Artificial Sequence
<220> FEATURE:
<223> OTHER INFORMATION: DNA Adaptor 1B

<400> SEQUENCE: 14
ggcccgtcca                                                            10

<210> SEQ ID NO 15
<211> LENGTH: 8
<212> TYPE: DNA
<213> ORGANISM: Artificial Sequence
<220> FEATURE:
<223> OTHER INFORMATION: DNA Adaptor 2B

<400> SEQUENCE: 15 cggctcca                                                               8

<210> SEQ ID NO 16
<211> LENGTH: 27
<212> TYPE: DNA
<213> ORGANISM: Artificial Sequence
<220> FEATURE:
<223> OTHER INFORMATION: GST Primer 1
```

```
<400> SEQUENCE: 16
ttgaattcca aaccagtgtg tctgccc                                          27

<210> SEQ ID NO 17
<211> LENGTH: 28
<212> TYPE: DNA
<213> ORGANISM: Artificial Sequence
<220> FEATURE:
<223> OTHER INFORMATION: GST Primer 2

<400> SEQUENCE: 17
aagctcgagt cgtcaccctg gcaagaat                                         28

<210> SEQ ID NO 18
<211> LENGTH: 18
<212> TYPE: DNA
<213> ORGANISM: Artificial Sequence
<220> FEATURE:
<223> OTHER INFORMATION: Mutagenic Primer 1

<400> SEQUENCE: 18
ggccctccag cgtcaccc                                                    18

<210> SEQ ID NO 19
<211> LENGTH: 27
<212> TYPE: DNA
<213> ORGANISM: Artificial Sequence
<220> FEATURE:
<223> OTHER INFORMATION: Mutagenic Primer 2

<400> SEQUENCE: 19
ccgcaggcta cattgtaa agaaacc                                            27

<210> SEQ ID NO 20
<211> LENGTH: 24
<212> TYPE: DNA
<213> ORGANISM: Artificial Sequence
<220> FEATURE:
<223> OTHER INFORMATION: Mutagenic Primer 3

<400> SEQUENCE: 20
tcctgctctg ttggcttgag ttca                                             24

<210> SEQ ID NO 21
<211> LENGTH: 20
<212> TYPE: DNA
<213> ORGANISM: Artificial Sequence
<220> FEATURE:
<223> OTHER INFORMATION: Mutagenic Primer 4

<400> SEQUENCE: 21
cccacaatct ggctctggcg                                                  20

<210> SEQ ID NO 22
<211> LENGTH: 24
<212> TYPE: DNA
<213> ORGANISM: Artificial Sequence
<220> FEATURE:
<223> OTHER INFORMATION: Mutagenic Primer 5

<400> SEQUENCE: 22
cgaattcgca agatggcttt gaac                                             24

<210> SEQ ID NO 23
```

```
<211> LENGTH: 18
<212> TYPE: DNA
<213> ORGANISM: Artificial Sequence
<220> FEATURE:
<223> OTHER INFORMATION: Mutagenic Primer 6

<400> SEQUENCE: 23
gggtgacgct ggagggcc                                          18

<210> SEQ ID NO 24
<211> LENGTH: 27
<212> TYPE: DNA
<213> ORGANISM: Artificial Sequence
<220> FEATURE:
<223> OTHER INFORMATION: Mutagenic Primer 7

<400> SEQUENCE: 24
ggtttcttta caatgtatag cctgcgg                                27

<210> SEQ ID NO 25
<211> LENGTH: 24
<212> TYPE: DNA
<213> ORGANISM: Artificial Sequence
<220> FEATURE:
<223> OTHER INFORMATION: Mutagenic Primer 8

<400> SEQUENCE: 25
tgaactcaag ccaacagagc agga                                   24

<210> SEQ ID NO 26
<211> LENGTH: 20
<212> TYPE: DNA
<213> ORGANISM: Artificial Sequence
<220> FEATURE:
<223> OTHER INFORMATION: Mutagenic Primer 9

<400> SEQUENCE: 26
cgccagagcc agattgtggg                                        20

<210> SEQ ID NO 27
<211> LENGTH: 25
<212> TYPE: DNA
<213> ORGANISM: Artificial Sequence
<220> FEATURE:
<223> OTHER INFORMATION: Mutagenic Primer 10

<400> SEQUENCE: 27
cgtctagatt agccgtctgc cctca                                  25

<210> SEQ ID NO 28
<211> LENGTH: 25
<212> TYPE: DNA
<213> ORGANISM: Artificial Sequence
<220> FEATURE:
<223> OTHER INFORMATION: Actin Primer 1

<400> SEQUENCE: 28
atatcgccgc gctcgtcgtc gacaa                                  25

<210> SEQ ID NO 29
<211> LENGTH: 26
<212> TYPE: DNA
<213> ORGANISM: Artificial Sequence
<220> FEATURE:
<223> OTHER INFORMATION: Actin Primer 2

<400> SEQUENCE: 29
```
agccacacgc agctcattgt agaagg            26

<210> SEQ ID NO 30
<211> LENGTH: 6
<212> TYPE: PRT
<213> ORGANISM: Artificial Sequence
<220> FEATURE:
<223> OTHER INFORMATION: N-myristoylation site

<400> SEQUENCE: 30

Gly Ser Pro Pro Ala Ile
 1               5

<210> SEQ ID NO 31
<211> LENGTH: 6
<212> TYPE: PRT
<213> ORGANISM: Artificial Sequence
<220> FEATURE:
<223> OTHER INFORMATION: N-myristoylation site

<400> SEQUENCE: 31

Gly Thr Val Cys Thr Ser
 1               5

<210> SEQ ID NO 32
<211> LENGTH: 6
<212> TYPE: PRT
<213> ORGANISM: Artificial Sequence
<220> FEATURE:
<223> OTHER INFORMATION: N-myristoylation site

<400> SEQUENCE: 32

Gly Ala Ala Leu Ala Ala
 1               5

<210> SEQ ID NO 33
<211> LENGTH: 6
<212> TYPE: PRT
<213> ORGANISM: Artificial Sequence
<220> FEATURE:
<223> OTHER INFORMATION: N-myristoylation site

<400> SEQUENCE: 33

Gly Ser Lys Cys Ser Asn
 1               5

<210> SEQ ID NO 34
<211> LENGTH: 6
<212> TYPE: PRT
<213> ORGANISM: Artificial Sequence
<220> FEATURE:
<223> OTHER INFORMATION: N-myristoylation site

<400> SEQUENCE: 34

Gly Val Asn Leu Asn Ser
 1               5

<210> SEQ ID NO 35
<211> LENGTH: 6
<212> TYPE: PRT
<213> ORGANISM: Artificial Sequence
<220> FEATURE:
<223> OTHER INFORMATION: N-myristoylation site

<400> SEQUENCE: 35

Gly Gly Glu Ser Ala Leu

```
<210> SEQ ID NO 36
<211> LENGTH: 6
<212> TYPE: PRT
<213> ORGANISM: Artificial Sequence
<220> FEATURE:
<223> OTHER INFORMATION: N-myristoylation site

<400> SEQUENCE: 36

Gly Asn Val Asp Ser Cys
 1               5

<210> SEQ ID NO 37
<211> LENGTH: 6
<212> TYPE: PRT
<213> ORGANISM: Artificial Sequence
<220> FEATURE:
<223> OTHER INFORMATION: N-myristoylation site

<400> SEQUENCE: 37

Gly Ser Gly Cys Ala Lys
 1               5

<210> SEQ ID NO 38
<211> LENGTH: 6
<212> TYPE: PRT
<213> ORGANISM: Artificial Sequence
<220> FEATURE:
<223> OTHER INFORMATION: N-myristoylation site

<400> SEQUENCE: 38

Gly Cys Ala Lys Ala Tyr
 1               5

<210> SEQ ID NO 39
<211> LENGTH: 5
<212> TYPE: PRT
<213> ORGANISM: Artificial Sequence
<220> FEATURE:
<223> OTHER INFORMATION: N-myristoylation site

<400> SEQUENCE: 39

Gly Val Tyr Gly Asn
 1               5

<210> SEQ ID NO 40
<211> LENGTH: 8
<212> TYPE: PRT
<213> ORGANISM: Artificial Sequence
<220> FEATURE:
<223> OTHER INFORMATION: P-loop

<400> SEQUENCE: 40

Ala Thr Glu Glu Lys Gly Lys Thr
 1               5

<210> SEQ ID NO 41
<211> LENGTH: 23
<212> TYPE: PRT
<213> ORGANISM: Artificial Sequence
<220> FEATURE:
<223> OTHER INFORMATION: LDL-receptor class A

<400> SEQUENCE: 41

Cys Ile Asn Pro Ser Asn Trp Cys Asp Gly Val Ser His Cys Pro Gly
 1               5                  10                  15
```

```
Gly Glu Asp Glu Asn Arg Cys
            20

<210> SEQ ID NO 42
<211> LENGTH: 6
<212> TYPE: PRT
<213> ORGANISM: Artificial Sequence
<220> FEATURE:
<223> OTHER INFORMATION: Serine proteases, typsin family, histidine
      active site

<400> SEQUENCE: 42

Val Thr Ala Ala His Cys
 1               5

<210> SEQ ID NO 43
<211> LENGTH: 12
<212> TYPE: PRT
<213> ORGANISM: Artificial Sequence
<220> FEATURE:
<223> OTHER INFORMATION: Serine proteases, typsin family, histidine
      active site

<400> SEQUENCE: 43

Asp Ser Cys Gln Gly Asp Ser Gly Gly Pro Leu Val
 1               5                  10
```

TUMOR ANTIGEN USEFUL IN DIAGNOSIS AND THERAPY OF PROSTATE AND COLON CANCER

CROSS-REFERENCE TO RELATED APPLICATIONS

This application is a continuation-in-part application of U.S. Ser. No. 09/323,597 filed Jun. 1, 1999 which claims the benefit of U.S. provisional patent application Ser. Nos. 60/087,598, filed Jun. 1, 1998, now lapsed, 60/091,474 filed Jun. 29, 1998, now lapsed and 60/129,521, filed Apr. 14, 1999, now lapsed. The entire contents of these provisional and non-provisional patent applications are incorporated by reference into this application.

BACKGROUND OF THE INVENTION

Prostate cancer is the most frequently diagnosed cancer and second leading cause of cancer death in men. Some 45,000 men die annually of this disease. Only lung cancer has a higher mortality. The chance of a man developing invasive prostate cancer during his lifetime is 1 in 6. At the age of 50, a man has a greater than 40% chance of developing prostate cancer and nearly a 3% chance of dying from this disease. While some advances in the treatment of locally confined tumors have been achieved, prostate cancer is incurable once it has metastasized. Patients with metastatic prostate cancer are treated by hormonal ablation therapy, but with only short-term success. Eventually, these patients develop an androgen-refractory state leading to disease progression and death.

A continuing and fundamental problem in the management of prostate cancer is the absence of reliable diagnostic and prognostic markers capable of accurately detecting early-stage localized tumors and/or predicting disease susceptibility and progression. Early detection and diagnosis of prostate cancer currently relies on digital rectal examination (DRE), prostate specific antigen (PSA) measurements, transrectal ultrasonography (TRUS), and transrectal needle biopsy (TRNB). Serum PSA measurements in combination with DRE represent the leading diagnostic approach at present. However, this approach has major limitations which have fueled intensive research into finding better diagnostic markers of this disease. A number of markers have been identified, and at least one, PSA, is in widespread clinical use. However, ideal prostate tumor markers have been extremely elusive and no marker has yet proven reliable for predicting progression of the disease. Thus, there is a need for more reliable and informative diagnostic and prognostic methods in the management of prostate cancer.

In addition, there is also great interest in identifying prostate-specific proteins that could be appropriate as therapeutic targets, as there is no effective treatment for patients who develop recurrent disease or who have been diagnosed with metastatic disease. Although hormone ablation therapy can palliate these patients, the majority inevitably progress to develop incurable, androgen-independent disease (Lalani et al., 1997, Cancer Metastasis Rev. 16: 29–66).

PSA is the most widely used tumor marker for screening, diagnosis, and monitoring prostate cancer today. In particular, several immunoassays for the detection of serum PSA are in widespread clinical use. Recently, a reverse transcriptase-polymerase chain reaction (RT-PCR) assay for PSA mRNA in serum has been developed. However, PSA is not a disease-specific marker, as elevated levels of PSA are detectable in a large percentage of patients with BPH and prostatitis (25–86%)(Gao et al., 1997, Prostate 31: 264–281), as well as in other nonmalignant disorders and in some normal men, a factor which significantly limits the diagnostic specificity of this marker. For example, elevations in serum PSA of between 4 to 10 ng/ml are observed in BPH, and even higher values are observed in prostatitis, particularly acute prostatitis. BPH is an extremely common condition in men. Further confusing the situation is the fact that serum PSA elevations may be observed without any indication of disease from DRE, and vice-versa. Moreover, it is now recognized that PSA is not prostate-specific and has a variety of complex biological activities (See e.g. Fortier et al., J. Natl. Cancer Inst. 1999, 91(19):1635–40).

Various methods designed to improve the specificity of PSA-based detection have been described, such as measuring PSA density and the ratio of free vs. complexed PSA. However, none of these methodologies have been able to reproducibly distinguish benign from malignant prostate disease. In addition, PSA diagnostics have sensitivities of between 57–79% (Cupp & Osterling, 1993, Mayo Clin Proc 68:297–306), and thus miss identifying prostate cancer in a significant population of men with the disease.

Prostate-Specific Membrane Antigen (PSMA) is a recently described cell surface marker of prostate cancer which has been the subject of various studies evaluating its use as a diagnostic and therapeutic marker. PSMA expression is largely restricted to prostate tissues, but detectable levels of PSMA mRNA have been observed in brain, salivary gland, small intestine, and renal cell carcinoma (Israeli et al., 1993, Cancer Res 53: 227–230). PSMA protein is highly expressed in most primary and metastatic prostate cancers, but is also expressed in most intraepithelial neoplasia specimens (Gao et al., supra). Preliminary results using an Indium-111 labeled, anti-PSMA monoclonal antibody to image recurrent prostate cancer show some promise (Sodee et al., 1996, Clin Nuc Med 21: 759–766). PSMA is a hormone dependent antigen requiring the presence of functional androgen receptor. Since not all prostate cancer cells express androgen receptor, the clinical utility of PSMA as a therapeutic target may be inherently limited. Clinical trials designed to examine the effectiveness of PSMA immunotherapy are also underway.

Prostate Stem Cell Antigen (PSCA) is another recently described cell surface marker of prostate cancer (Reiter et al., 1998, Proc. Natl. Acad. Sci. USA 95: 1735–1740). PSCA expression has been shown to be predominantly prostate specific and widely over-expressed across all stages of prostate cancer, including high grade prostatic intraepithelial neoplasia (PIN), androgen-dependent and androgen-independent prostate tumors. The PSCA gene has been mapped to chromosome 8q24.2, a region of allelic gain in more than 80% of prostate cancers. PSCA shows promise as a diagnostic and therapeutic target in view of its cell surface location, prostate specificity, and greatly unregulated expression in prostate cancer cells.

Progress in the identification of specific markers has been slow due to a lack of experimental animal model systems that recapitulate clinical disease. Attempted solutions to this problem have included the generation of prostate cancer cell lines (Horoszewicz et al., 1983, Cancer Res. 43, 1809) and prostate cancer xenografts (Pretlow et al., 1991, Cancer Res. 51, 3814; van Weerden et al., 1996, Am. J. Pathol. 149, 1055; Klein et al., 1997, Nature Med. 3, 402). However, these approaches have met with limited success. For example, xenografts have generally produced low long-term survival rates. In addition, none of the most widely used human prostate cancer cell lines—PC-3, DU-145, and LNCaP—have been shown to reproducibly give rise to osteoblastic lesions typical of prostate cancer. A further limitation of the DU-145 and PC-3 cell lines is that these cells do not express prostate specific antigen (PSA) or androgen receptor (AR) (Kaighn et al., 1979, Invest. Urol. 17: 16–23; Gleave et al., 1992, Cancer Res. 52: 1598–1605), questioning their relevance to clinical prostate cancer. The LNCaP cell line is androgen responsive and expresses PSA, but contains a mutation in the androgen receptor which alters ligand specificity.

Recently, however, a series of prostate cancer xenografts (derived from patient tumors) demonstrating genetic and phenotypic characteristics closely paralleling the human clinical situation have been described (Klein et al., 1997, Nature Med. 3: 402). These LAPC (Los Angeles Prostate Cancer) xenografts have survived passage in severe combined immune deficient (SCID) mice for longer than one year. The LAPC-4 xenograft model systems has the capacity to mimic the transition from androgen dependence to androgen independence and the development of metastatic lesions (Klein et al., 1997, supra). LAPC-4 tumors regress in male mice after castration, but re-grow within 2–3 months as androgen independent tumors. Both androgen dependent (AD) and androgen independent (AI) LAPC-4 xenograft tumors express equal levels of the prostate specific markers PSA, PSMA and PSCA (prostate stem cell antigen), which was identified using representational difference analysis of cDNAs derived from the AD and AI variants of the LAPC-4 xenograft.

SUMMARY OF THE INVENTION

The present invention relates to methods and compositions for the diagnosis and therapy of prostate and colon cancer, derived from or based on a novel prostate-specific, androgen-regulated, serine protease termed 20P1F12/TMPRSS2 and extensively described herein. A full length cDNA comprising the entire coding sequence of the 20P1F12/TMPRSS2 gene (also designated 20P1F12-GTC1 herein) is provided (FIG. 1). This cDNA encodes a protein which is highly related to, but structurally distinct from, the recently published TMPRSS2 (Paoloni-Giacobino et al., 1997, Genomics 44: 309–320). The 20P1F12/TMPRSS2 gene also shows a very different expression pattern relative to the expression profile of TMPRSS2.

More specifically, the invention provides polynucleotides corresponding or complementary to all or part of the 20P1F12/TMPRSS2 gene, mRNA, and/or coding sequence, preferably in isolated form, including polynucleotides encoding 20P1F12/TMPRSS2 proteins and fragments thereof, DNA, RNA, DNA/RNA hybrid, and related molecules, polynucleotides or oligonucleotides complementary to the 20P1F12/TMPRSS2-encoding polynucleotides. Also provided are means for isolating cDNAs and the genes encoding 20P1F12/TMPRSS2. Recombinant DNA molecules containing 20P1F12/TMPRSS2 polynucleotides, cells transformed or transduced with such molecules, and host-vector systems for the expression of 20P1F12/TMPRSS2 gene products are also provided. The invention further provides 20P1F12/TMPRSS2 proteins and polypeptide fragments thereof.

Methods for detecting the presence of 20P1F12/TMPRSS2 polynucleotides and proteins in various biological samples, as well as methods for identifying cells that express 20P1F12/TMPRSS2 are provided. The invention further provides prognostic and diagnostic method of examining a biological sample for evidence of disregulated cellular growth by comparing the status of 20P1F12/TMPRSS2 in the biological sample to the status of 20P1F12/TMPRSS2 in a corresponding normal sample, wherein alterations in the status of 20P1F12/TMPRSS2 in the biological sample are associated with disregulated cellular growth. Diagnostic imaging methods for the management of prostate and colon cancers are also provided.

The invention further provides various therapeutic compositions and strategies for treating prostate cancer, including particularly, 20P1F12/TMPRSS2 polypeptide and anti-20P1F12/TMPRSS2 antibody therapy methods and compositions, cancer vaccines, and small molecule therapy.

The invention provides antibodies that bind to 20P1F12/TMPRSS2 proteins and polypeptide fragments thereof, including polyclonal and monoclonal antibodies, murine and other mammalian antibodies, chimeric antibodies, humanized and fully human antibodies, and antibodies labeled with a detectable marker or toxin or therapeutic composition. Several monoclonal antibodies specifically reactive with 20P1F12/TMPRSS2 are also described herein. These and other 20P1F12/TMPRSS2 antibodies are useful in molecular diagnostic assays and diagnostic imaging methods for detecting, localizing and characterizing carcinomas of the prostate and colon and metastases thereof. Cancer vaccines are also provided.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIG. 1. Nucleotide (SEQ ID NO: 1) and deduced amino acid (SEQ ID NO: 2) sequences of cDNA clone 20P1F12-GTC1 (Example 3)(as deposited with the ATCC; Accession No. 207097).

FIG. 2. Nucleotide (SEQ ID NO: 3) and deduced amino acid (SEQ ID NO: 4) sequences of TMPRSS2 gene sequence as published in Paoloni-Giacobino et al., 1997, Genomics 44: 309–320.

FIGS. 3A–B. FIG. 3A shows an amino acid sequence alignment comparing 20P1F12-GTC1 cDNA (Example 3) with the previously published sequence of TMPRSS2 (Paoloni-Giacobino et al., 1997, Genomics 44: 309–320). Amino acid differences are shown in bold type. FIG. 3B shows a schematic representation of the domain structure of 20P1F12/TMPRSS2.

FIG. 4. Nucleotide sequence of initially isolated SSH clone 20P1F12 (SEQ ID NO: 5).

FIG. 8. Characterization of Monoclonal antibodies directed against 20P1F12/TMPRSS2. Monoclonal antibodies towards 20P1F12/TMPRSS2 were generated using a purified GST-20P1F12/TMPRSS2 fusion protein as described in Example 5. Monoclonal antibodies were screened by western blotting against lysates derived from 293T cells transfected with a PcDNA 3.1 vector encoding myc His-20P1F12/TMPRSS2. (A) Six mAbs: 1F9 (IgG1, K), 2D10 (IgG1, K), 2F8, (IgG1, K) 6B11 (IgG1, K), 8C6 (IgG1, K) and 9G8 (IgG2a, K) that specifically recognize 20P1F12/TMPRSS2 were used to probe western blots from cell lysates derived from 293T cells transfected with either 20P1F12/TMPRSS2 (lane 1) or neo (as a control, lane 2) (B) Cell lysates from 293T cells transfected with 20P1F12/TMPRSS2 (lane 1) or neo (as a control, lane 2), LAPC-9 AD and LNCaP were probed with 1F9 anti-TMPRSS2 mAb. Molecular weight standards are indicated on the side in kilodaltons (KD).

FIG. 9. Biotinylation of 20P1F12/TMPRSS2. (A) His-tagged 20P1F12/TMPRSS2 or neo (as a control) were transfected in 293T cells. Intact cells were incubated with biotin to biotinylate cell proteins. Cell lysates were either analyzed by western blotting directly (lanes 1 and 2, or they were incubated with streptavidin to affinity purify all labeled cellular proteins). Streptavidin purified cell proteins were analyzed by western blotting using anti-His antibodies (lanes 3 and 4). Biotinylated protein was only detected in 20P1F12/TMPRSS2 transfected cells. (B) Biotinylated PC-3 (lane 2) and LNCaP (Lane 4), and unlabelled PC-3 (lane 1) and LNCaP (lane 3) were incubated with streptavidin gel and then analyzed by western blotting using 1F9 mAb. 20P1F12/TMPRSS2 was only detected in biotinylated samples. Molecular weight standards are indicated on the side in kilodaltons (KD).

FIG. 13. Effect of 20P1F12/TMPRSS2 expression in NIH 3T3 cells. NIH 3T3 cells were infected with retrovirus encoding either neo (as a control) or 20P1F12/TMPRSS2. Forty-eight hours after infection the cells were analyzed by light microscopy. Cells that appeared to accumulate high numbers of vacuoles are indicated with arrows.

FIG. 23. Expression of the 32 kD cleavage fragment of 20P1F12/TMPRSS2 and a novel 103 kD 20P1F12/TMPRSS2 immunoreactive complex in prostate and colon cancer patients and LNCaP tumor-bearing SCID mouse serum samples. 100 µl of sera from either a naïve or a LNCaP tumor-bearing SCID mouse (A) of 1 ml of the indicated human clinical serum samples (B) were immunoprecipitated with covalently coupled 1F9 anti-TMPRSS2 monoclonal antibody/protein G agarose beads as follows. SCID mouse sera and human sera were adjusted to 1 ml and 2 mls respectively with RIPA buffer (25 mM TRIS, pH 7.5, 150 mM NaCl, 1% Triton-X-100, 0.5% sodium deoxycholate, 0.1% SDS, 0.5 mM EDTA) and precleared with protein G agarose beads for 3 hours at 4° C. 1F9 anti-TMPRSS2 mAb was covalently coupled to protein G beads using the homobifunctional crosslinking reagent dimethyl pimelimidate (DMP) as described in "Using Antibodies, a Laboratory Manual", Harlow and Lane, 1999, pg. 323. Then 50 μl of a 50% slurry of 1F9/protein G beads (~50 μg mAb) was added to each sample and incubated overnight at 4° C. Immunoprecipitates were washed 4 times in RIPA buffer and immune complexes were dissociated by the addition of 40 μl of 3X SDS-PAGE sample buffer and heating. 25 μl/lane of the indicated volumes of whole tissue lysate from the prostate of a normal 28 year old male accident victim were separated by SDS-PAGE, transferred to nitrocellulose, and subjected to anti-TMPRSS2 Western analysis with 1F9 mAb as described in FIG. 19. Arrows indicate the 32 kD 20P1F12/TMPRSS2 cleavage fragment and the novel 103 kD anti-TMPRSS2 immunoreactive band. A darker exposure of the lower portion of panel A is presented to better visualize the 32 kD fragment in LNCaP tumor-bearing mouse serum.

FIG. 24. Expression of the 32 kD cleavage fragment of 20P1F12/TMPRSS2 and a novel 90 kD 20P1F12/TMPRSS2 immunoreactive complex in normal seminal plasma. A. Tissue lysates of LAPC4 and LAPC9 SCID mouse xenografts and LNCaP and LAPC4 cell line cultures of normal seminal plasma were subjected to Western analysis with anti-TMPRSS2 mAb 1F9. B. Normal seminal plasma or cell lysates and conditioned supernatants of LNCaP cells incubated for 4 days in charcoal/dextran-stripped 2% FBS and then incubated in the presence (+) or absence (−) of 10 nM mibolerone for 48 hours were subjected to immunoprecipitation and Western analysis with 1F9 mAb. Arrows indicate the 32 kD cleavage fragment, 70 kD full length 20P1F12/TMPRSS2 protein, and the novel 103 kD and 90 kD 20P1F12/TMPRSS2 immunoreactive complexes present in conditioned LNCaP supernatant and seminal plasma, respectively.

FIGS. 27A–C. Parental PC3 cells and PC3 cells stably expressing 20P1F12/TMPRSS2 were assayed for their invasive potential using a Transwell Insert System (Becton Dickinson). The cells were loaded with a fluorescent dye, namely calcein, and plated in the top well of the transwell insert. Invasion was determined by measuring the fluorescence of cells in the lower chamber relative to the fluorescence of the entire cell population. The assay was performed in triplicate.

DETAILED DESCRIPTION OF THE INVENTION

Figure 5:
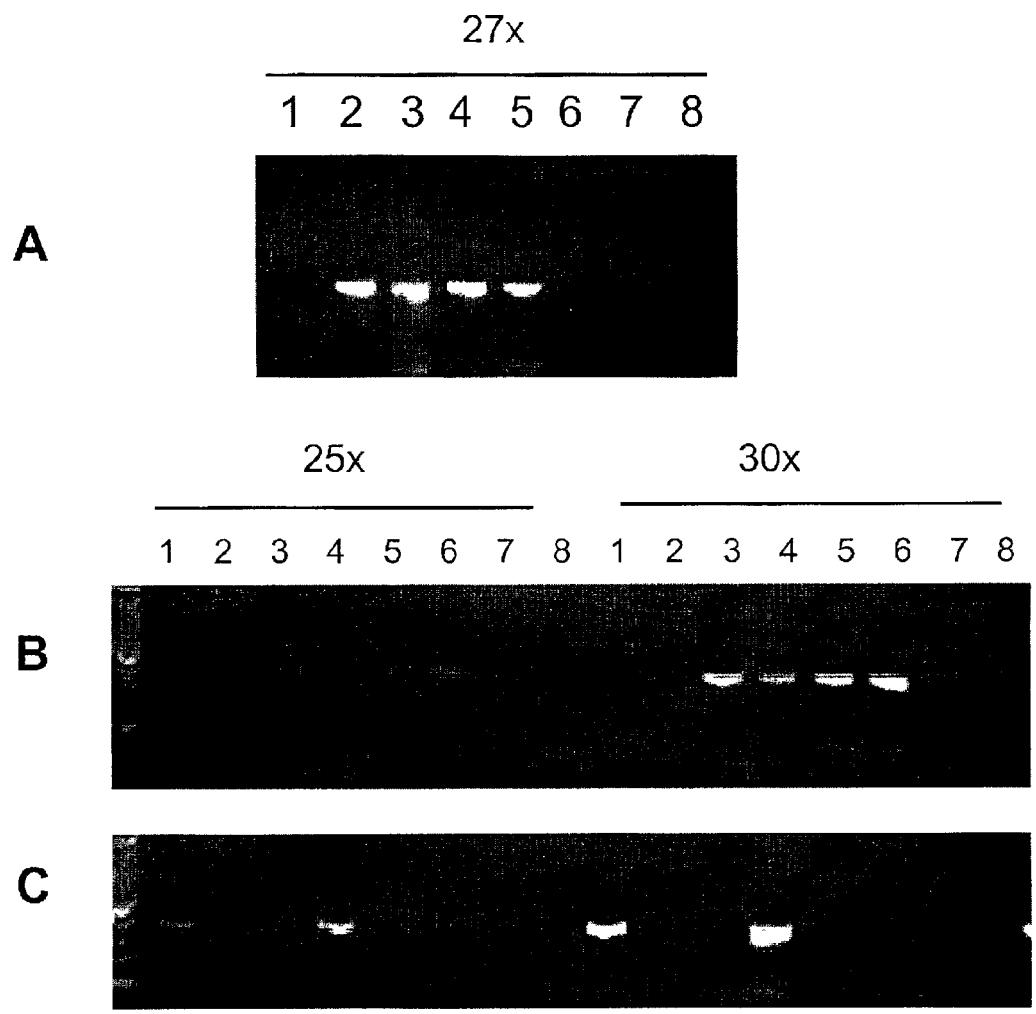
FIGS. 5A–D. RT-PCR analysis of 20P1F12/TMPRSS2 gene expression in prostate cancer xenografts, normal prostate, and other tissues and cell lines, showing approximately equal levels of expression in normal prostate and three prostate cancer xenografts (FIG. 5A); and showing largely prostate specific expression in normal human tissues, with significantly lower expression levels detectable in colon, pancreas, kidney and lung (FIGS. 5B and C). 20P1F12/TMPRSS2 is also shown to be expressed in bladder cancer tissues (FIG. 5D).

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., 1989, Molecular Cloning: A Laboratory Manual, 2d ed., Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA.

Figure 8:
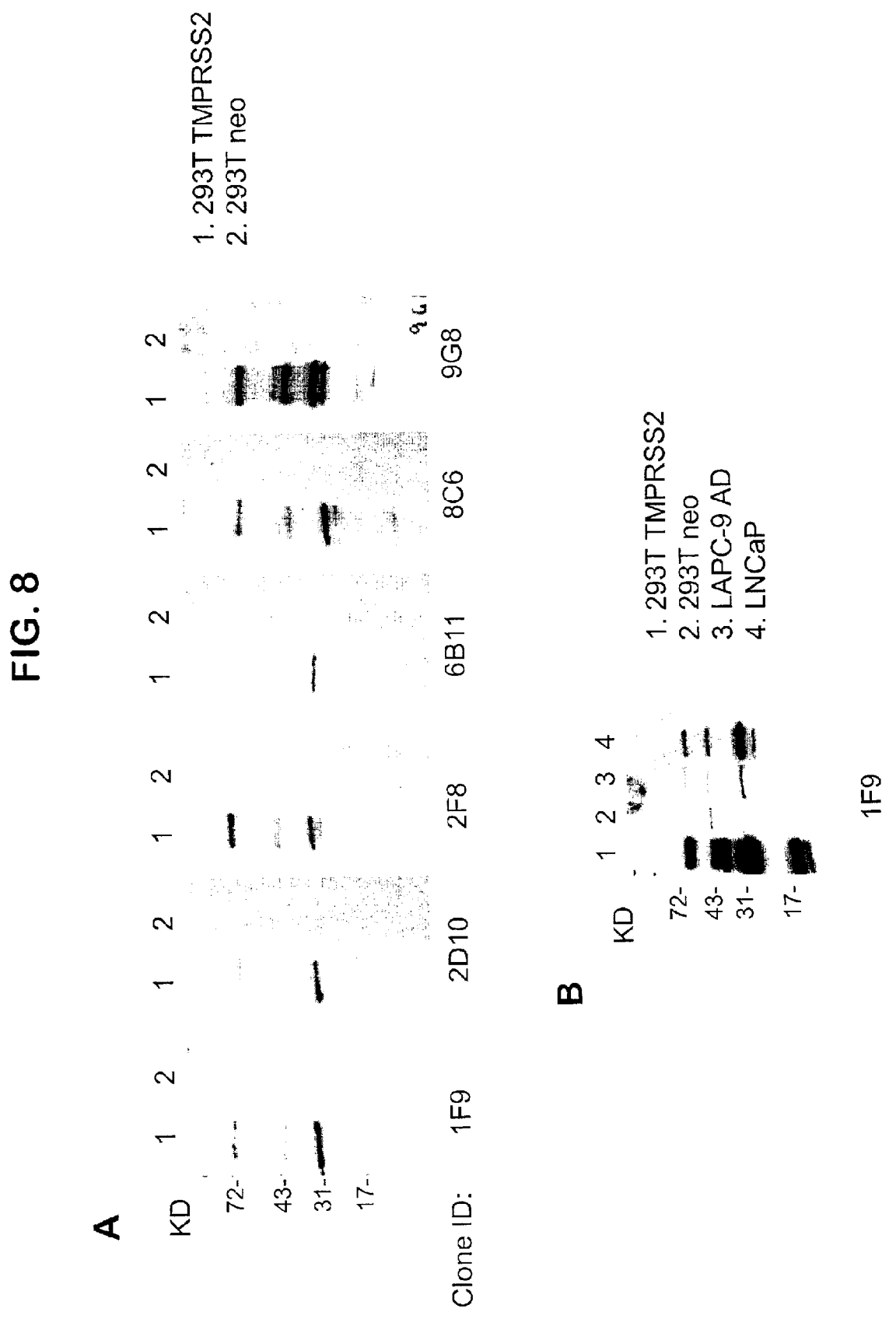

As used herein, the term "polypeptide" means a polymer of at least 6 amino acids. Throughout the specification, standard three letter or single letters designations for amino acids are used. In this context a "20P1F12/TMPRSS2 polypeptide" includes for example, a protein having the 492 amino acid sequence protein shown in FIG. 1 as well as the 32 kD protease domain containing fragment that is shown for example in FIG. 8.

As used herein, the terms "hybridize", "hybridizing", "hybridizes" and the like, used in the context of polynucleotides, are meant to refer to conventional hybridization conditions, preferably such as hybridization in 50% formamide/6XSSC/0.1% SDS/100 μg/ml ssDNA, in which temperatures for hybridization are above 37 degrees C and temperatures for washing in 0.1X SSC/0.1% SDS are above 55 degrees C., and most preferably to stringent hybridization conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publications, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization and denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C.

"Moderately stringent conditions" may be identified as described by Sambrook et al., 1989, Molecular Cloning: A Laboratory Manual, New York: Cold Spring Harbor Press, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

In the context of amino acid sequence comparisons, the term "identity" is used to express the percentage of amino acid residues at the same relative positions that are the same. Also in this context, the term "homology" is used to express the percentage of amino acid residues at the same relative positions that are either identical or are similar, using the conserved amino acid criteria of BLAST analysis, as is generally understood in the art. For example, % identity values may be generated by WU-BLAST-2 (Altschul et al., 1996, Methods in Enzymology 266:460–480; available at http address "blast.wustl/edu/blast/README.html"). Further details regarding amino acid substitutions, which are considered conservative under such criteria, are provided below.

Additional definitions are provided throughout the subsections that follow.

Figure 5D:
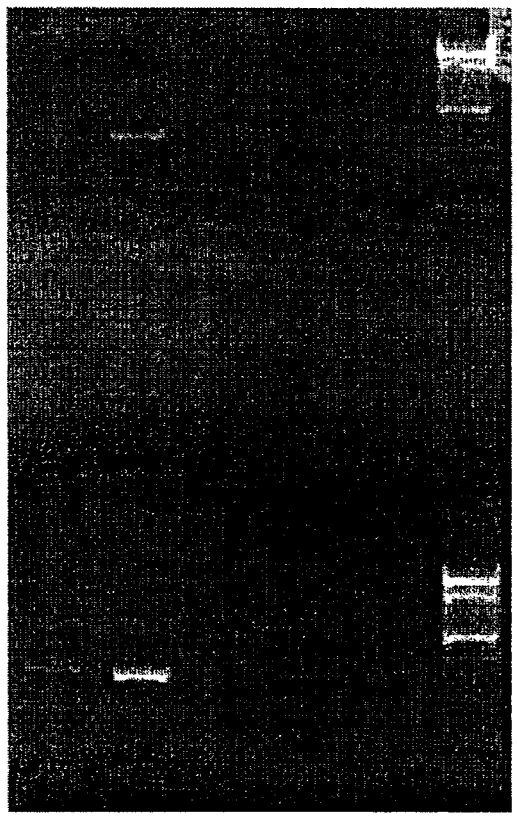

The present invention relates to methods and compositions for the diagnosis and therapy of certain cancers using isolated polynucleotides corresponding to the 20P1F12/ TMPRSS2 gene, proteins encoded by the 20P1F12/ TMPRSS2 gene and fragments thereof, and antibodies capable of specifically recognizing and binding to 20P1F12/ TMPRSS2 proteins. Throughout the Application, the methods and compositions are typically described for use in the context of prostate and colon cancers. As the data presented herein shows that 20P1F12/TMPRSS2 is expressed in tumors arising from other cell lineages however (see e.g. FIG. 5D showing 20P1F12/TMPRSS2 expression in bladder cancers), the skilled artisan that the diagnostic and therapeutic disclosures are applicable to cancers of these lineages as well.

The 20P1F12/TMPRSS2 gene encodes a predicted 492 amino acid protein containing multiple domains including a serine protease domain, a scavenger receptor cysteine-rich domain, an LDL receptor class A domain, and a predicted transmembrane domain as has been described for TMPRSS2 (Paoloni-Giacobino et al., 1997, Genomics 44: 309–320). Paoloni-Giacobino et al. found that the TMPRSS2 gene is expressed strongly in small intestine and only weakly in several other tissues and have also mapped the TMPRSS2 gene to chromosome 21. The physiological role of TMPRSS2 is unknown. Applicants have cloned a full length cDNA comprising the entire coding region of the 20P1F12/

TMPRSS2 gene, but it contains several nucleotide sequence differences relative to the published sequence of TMPRSS2. Six of these sequence differences result in amino acid differences. The specific nature and significance of these changes are presently unknown. However, a number of the amino acid differences between the protein described by Paoloni-Giacobino et al. and the 20P1F12/TMPRSS2 protein described herein are nonconservative changes falling within the protein's protease domain (see e.g. FIG. 3). Consequently, a protein having the sequence described in Paoloni-Giacobino et al. may have a significantly different functional activity from the protein described herein. Moreover, it is known in the art that genes possess a certain amount of variability and that this variability can effect various aspects of cell physiology, including those associated with oncogenesis (see e.g. Rebbeck et al., J. Natl. Cancer Inst. 90(16): 1225–1229 (1998) and Tonin et al., Semin. Surg. Oncol. 18(4): 281–286 (2000)). In addition, applicants novel 20P1F12/TMPRSS2 has a completely different expression pattern in comparison to what has been known for the previously reported TMPRSS2.

Because 20P1F12/TMPRSS2 is predominantly expressed in prostate and colon cancer cells and contains a protease domain, it is possible that it functions in the development, invasion and/or progression of prostate and colon cancer, particularly in the development of metastatic disease. In this regard, proteases are known to be involved in invasion and metastasis of cancer cells (Henriet et al., 1999, APMIS 107(1):111–9; Rochefort et al., 1999, APMIS 107(1):86–95; Webber et al., 1995, Clin Cancer Res 1(10):1089–94; Duffy, 1996, Clin Cancer Res 2(4):613–8; Webber and Waghray, 1995 Clin Cancer Res 1(7):755–61). For instance, urokinase-type plasminogen activator (u-PA), cathepsin D and PSA are though to modulate the ability of prostate cancer cells to metastasize (see e.g. Fortier et al., J. Nat. Cancer Inst. 91(19): 1635–1640(1999)). The potential involvement of 20P1F12/TMPRSS2 function in prostate and colon cancer, and particularly in metastasis, may be evaluated as described in the Examples below.

Figure 21:
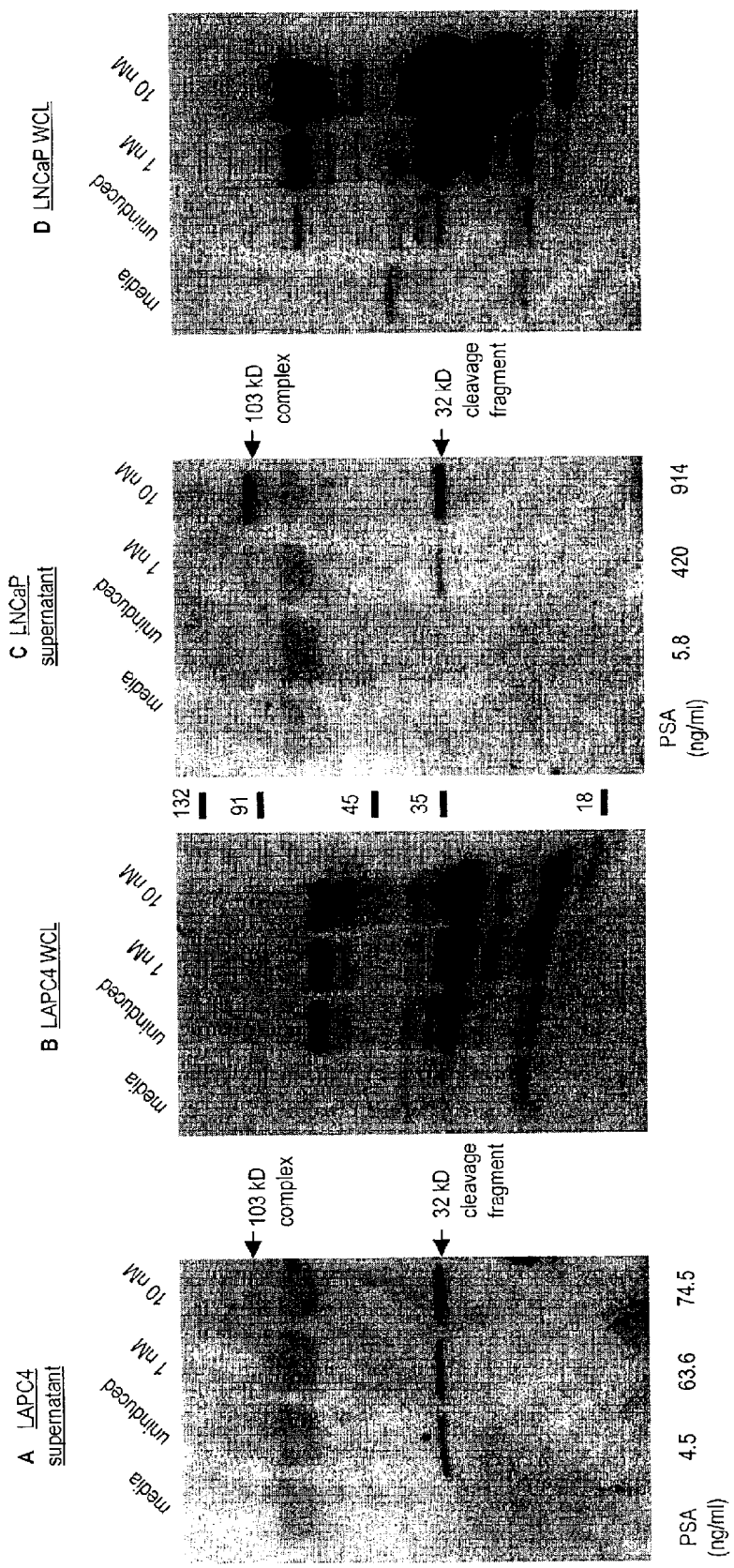
FIG. 21. Androgen induction and release of the 32 kD auto-proteolytic fragment into the supernatants of LAPC4 and LNCaP cells and appearance of a novel 103 kD anti-TMPRSS2 immunoreactive protein complex. LAPC4 and LNCaP cells (70% confluent 10 cm dishes) were starved of androgen by incubation in RPMI media containing 2% CD-FBS for 5 days. Media was aspirated and replaced with 4 mls of fresh RPMI+2% CD-FBS media with or without either 1 or 10 nM mibolerone and further incubated for 48 hours. Whole cell lysates ("WCL", 25 µg/lane) or conditioned tissue culture supernatants (25 µl, 0.22 µM sterile filtered) were then subjected to SDS-PAGE and anti-TMPRSS2 Western analysis with 1F9 mAb as described in FIG. 19. Arrows indicate the 32 kD auto-proteolytic fragment and 103 kD anti-TMPRSS2 immunoreactive complex in conditioned media. PSA concentrations of supernatants, determined by a commercially available ELISA (Anogen), are indicated for comparison to a known androgen-induced secreted protein.

Interestingly, the 20P1F12/TMPRSS2 and TMPRSS2 primary structure contains protein-protein interaction domains and a protease domain and is found to form a protein complex (see e.g. FIG. 21). The function of 20P1F12/TMPRSS2 and TMPRSS2 is unclear. The function of 20P1F12/TMPRSS2 and TMPRSS2 may involve binding to substrate proteins in the extracellular milieu through its SRCR and/or LDLA domains. Examples of proteins that exhibit SRCR domains include: CD6, an adhesion molecule that binds to ALCAM (activated leukocyte cell adhesion molecule) and mediates thymocyte-thymic epithelium cell binding (Whitney et al., 1995, J. Biol Chem 270:18187); CD5 (Ly-1) a T-cell protein that binds CD72 on B-cells and may be involved in T-B cell communication (Luo et al., 1992, J Immunol 148:1630); BSSP-3, a brain-specific serine protease with a kringle-like structure and three scavenger receptor cysteine-rich motifs (Yamamura et al., 1997, Biochem Biophys Res Commun 239:386). LDLR domains have been implicated in the binding and recycling of protease-inhibitor complexes such as uPA plasminogen activator-1 (PAI-1) complexes (see e.g. Strickl et al., FASEB J. 9: 890–898 (1995); Moestrup Biochim. Biophys. Acta 1197: 337–360 (1994)).

Prostate tissue expresses a number of androgen regulated proteases, including PSA, human glandular kallikrein (hK2) and prostase/KLK-L1 (Wolf et al., 1992, Mol Endocrinol 6:753–762; Nelson et al., 1999 PNAS 96:3114–3119; Yousef et al., 1999, Cancer Res 59:4252–4256). 20P1F12/TMPRSS2 is unique among these proteases due to its structural features. It is a putative type II transmembrane protease with a scavenger receptor cysteine rich domain (SRCR) and a low density lipoprotein receptor A (LDLA) domain (Paoloni-Giacobino et al., 1997). The protease domain is located at the carboxyl-terminus, which is secreted as described herein. These features provided evidence that 20P1F12/TMPRSS2 protein can be expressed at the cell membrane and could function as a receptor for other proteins or small molecules. The 20P1F12/TMPRSS2 protease domain is most homologous to hepsin, also a type II transmembrane protease (Leytus et al., 1988, Biochemistry 27:1067) that is up-regulated in ovarian cancer (Yan et al., 1997, Cancer Res 57:2884). Sub-cellular fractionation studies localized Hepsin to the membraneous fraction of cultured HepG2 cells (Tsuji et al., 1991, J. Biol. Chem. 266:16948–16953). The studies provided herein show that in prostate and colon cancers, the majority of 20P1F12/TMPRSS2 protein is proteolytically cleaved and secreted. The remaining regions, including the LDLA and the SRCR domains, are likely still membrane associated and could function as receptors for intracellular components independent of the protease domain which could be involved, for example in the scavenging binding and recycling of protease-inhibitor complexes (see e.g. Takeuchi et al., PNAS: 96: 11054–11061 (1999)).

Mutational inactivation of the 20P1F12/TMPRSS2 protease shows that the cleavage and release of the protease domain is a consequence of its own catalytic activity, demonstrating that 20P1F12/TMPRSS2 is its own substrate (see e.g. Example 10). Similar auto-catalytic cleavage has also been observed for hepsin (Thien-Khai et al., 1997, J. Biol. Chem. 272(50):31315–31320). The auto-cleavage of 20P1F12/TMPRSS2 occurs at Arg 255 and results in the release of the protease domain. Tissue staining studies using anti-20P1F12/TMPRSS2 Mab provide evidence that the protein is concentrated in vesicular structures and is secreted into the glandular lumen of normal and cancerous prostate tissue. Analysis of cell culture media and sera from tumor bearing mice confirmed that 20P1F12/TMPRSS2 protease is secreted by prostate cancer cells. These data provide evidence that released 20P1F12/TMPRSS2 protease may be useful as a potential serum diagnostic or prognostic marker for prostate and possibly colon cancer and that the cleavage of the protease domain is involved in tumor growth and invasion. Proliferation and metastasis of cancer cells, as well as destruction of the normal tissue architecture may, like PSA, cause a rise in serum 20P1F12/TMPRSS2 levels that would signify the presence of cancer cells.

Secreted 20P1F12/TMPRSS2 protease may be involved in processing and possibly activating growth modulation factors present in the extracellular space. Recent work with PSA and hK2 have shown that they may play a role in activating growth modulation factors important in the osteoblastic response of bone metastasized prostate cancer (Koeneman et al., 1999, Prostate 39:246–261). One of these factors, parathyroid hormone-related protein (PTHrP), has been shown to increase the rate of prostate tumor growth in vivo and protect LNCaP cells from apoptosis (Dougherty et al., 1999, Cancer Res. 59:6015–6022). It remains to be seen whether 20P1F12/TMPRSS2 is capable of activating PTHrP and/or other factors that could influence prostate cancer and/or colon cancer growth. The expression pattern and localization of 20P1F12/TMPRSS2 makes it a previously un-appreciated target for therapy in cancers of the prostate and colon.

The invention is based, in part, upon the isolation of a cDNA fragment corresponding to the 20P1F12/TMPRSS2 gene by Suppression Subtraction Hybridization cloning and upon the detailed molecular and biochemical characterization studies described in the Examples. The initially isolated cDNA fragment, clone 20P1F12, showed identity in an overlapping part of the 3' untranslated sequence of the recently described full length cDNA encoding TMPRSS2. Primers designed to specifically amplify the gene corresponding to 20P1F12 were then used to characterize 20P1F12/TMPRSS2 expression in prostate cancer xenografts, normal prostate, and a variety of other normal and cancerous tissues. Full length cDNAs comprising the complete 20P1F12/TMPRSS2 gene were independently isolated from separate libraries and the entire coding sequence identified from these clones is provided herein (see e.g. FIG. 1).

The nucleotide and deduced amino acid sequences of the novel 20P1F12/TMPRSS2 gene (also designated 20P1F12-GTC1 herein) are shown in FIG. 1. There are significant differences in the amino acid sequences encoded by the 20P1F12-GRC1/TMPRSS2 gene compared to the previously reported sequence of TMPRSS2 (see amino acid alignment in FIG. 3). For example, four of the amino acid differences are in the protease domain, three of which are non-conservative amino acid differences and which could affect protease function and/or specificity. Applicants' novel 20P1F12/TMPRSS2 protein has been extensively characterized as further described in the Examples sections herein. The 20P1F12/TMPRSS2 protein is a glycosylated type II transmembrane protein with an secreted C-terminal protease domain.

The 20P1F12/TMPRSS2 gene is androgen-regulated. Interestingly, in prostate cancer, androgen regulation and the development of an androgen-refractory state is a significant aspect of the neoplastic progression and androgen independent growth is associated with metastatic disease. In addition, androgen receptor gene amplification is known to increase tissue PSA protein expression in hormone-refractory prostate carcinomas (see e.g. Koivisto et. al., J. Patholo. 189(2): 219–223 (1999); Koivisto et al., Am. J. Pathol. 152(1): 1–9 (1998)). The 20P1F12/TMPRSS2 protein is detectable at the cell surface. Expression of 20P1F12/TMPRSS2 is also observed in prostate cancer, including high level expression in advanced and metastatic disease. In addition, 20P1F12 appears to be over-expressed in colon cancer and may also be expressed in other cancers (see e.g. FIG. 5D).

Figure 6:
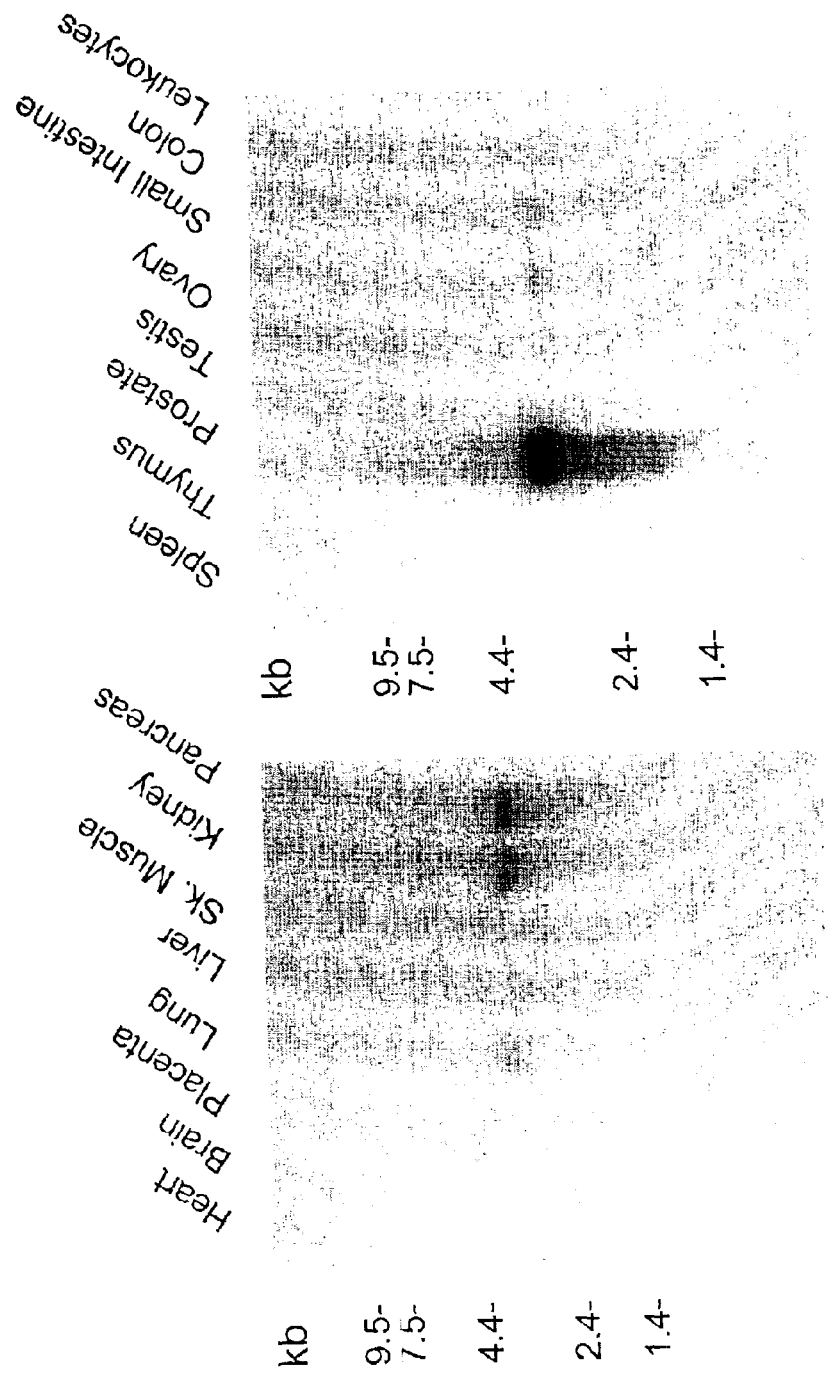
FIG. 6. Northern blot analysis of 20P1F12/TMPRSS2 gene expression in normal human tissues and prostate cancer xenografts using labeled clone 20P1F12 cDNA probe. Expression in 16 normal tissues largely restricted to prostate; with kidney, pancreas and lung showing 10- to 20-fold lower expression levels.

In addition to the differences in structure between applicants' the 20P1F12-GTC1/TMPRSS2 gene (FIG. 1) and the previously reported sequence (FIG. 2), the results of applicants expression analysis are contrary to those reported by Paoloni-Giacobino et al. In particular, applicants analysis of 20P1F12/TMPRSS2 gene expression by RT-PCR in 16 normal tissues shows the highest level expression in prostate, with substantially lower levels detected in colon, pancreas, kidney, liver and lung and no detectable expression in small intestine (FIG. 5, Panels B and C). Similar results were obtained on Northern blot analysis, although the expression level detected in prostate by Northern blot is extremely high relative to these other tissues in which only very low level expression is detected (FIG. 6). Moreover, as shown in Table 1, immunohistochemical analysis shows 20P1F12/TMPRSS2 protein expression in prostate and pancreas. In addition, the expression pattern of 20P1F12/TMPRSS2 (such as the data presented in FIG. 6) has been corroborated by other researchers (see e.g. Lin et al., Cancer Res. 1999, 59(17): 4180–4184).

Figure 7:
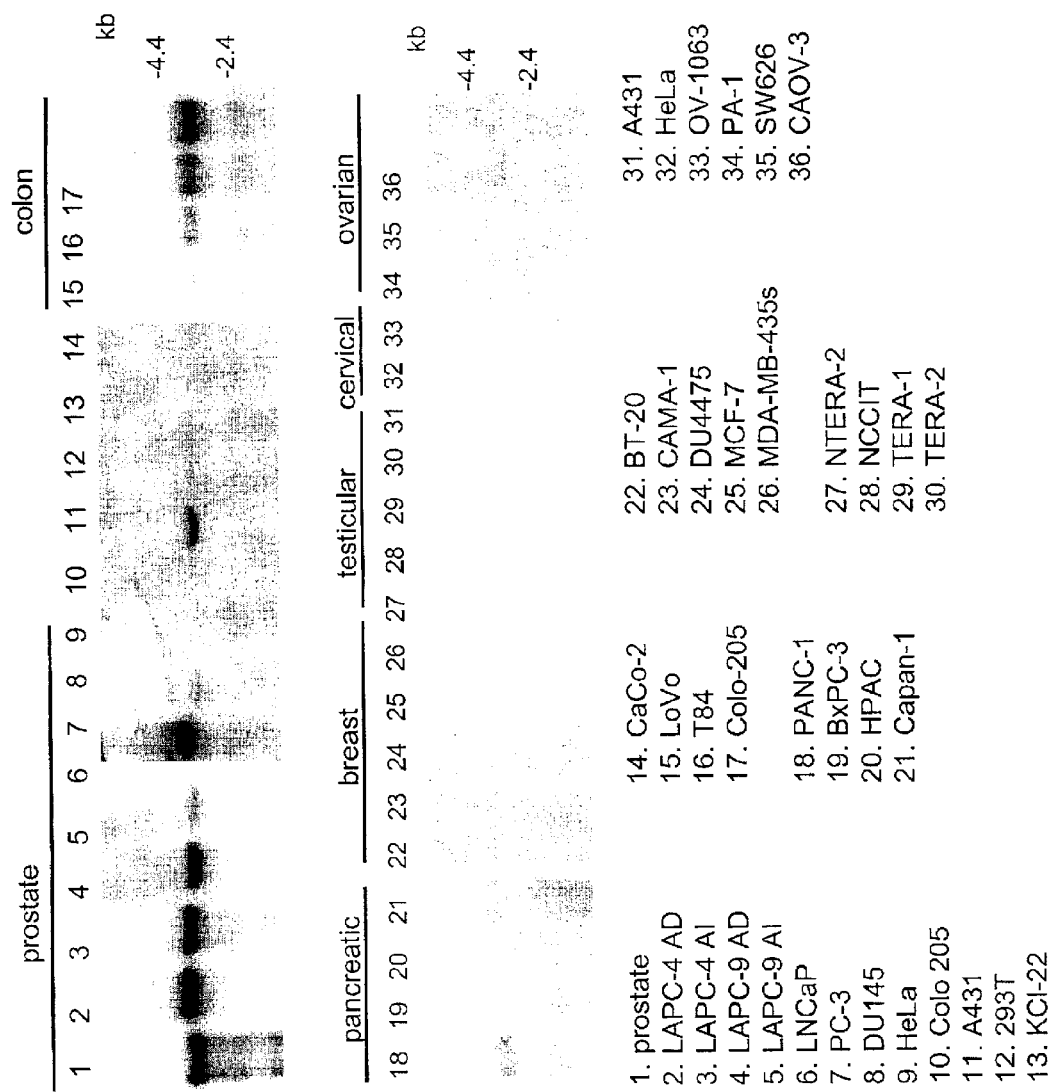
FIG. 7. Expression of 20P1F12/TMPRSS2 in prostate and colon cancer cell lines. Xenograft and cell line filters were prepared with 10 μg of total RNA per lane. The blots were analyzed using a 20P1F12/TMPRSS2 derived gene fragment probe. All RNA samples were normalized by ethidium bromide staining. Kilobases=kb. Except for LAPC-9 AI, expression of 20P1F12/TMPRSS2 in the xenografts was comparable to levels observed in normal prostate samples. In addition, lower level expression in the epidermoid carcinoma line A431 was observed.

Expression analysis also shows high level expression of 20P1F12/TMPRSS2 in all prostate cancer xenografts tested, at approximately the same levels seen in normal prostate (FIG. 5, Panel A). Northern blot analysis shows similar results, with somewhat lower level expression detected in the LAPC-9 xenograft relative to the LAPC-4 xenografts and normal prostate; expression is also detected in some of the prostate cancer cell lines analyzed (FIG. 7). The 20P1F12/TMPRSS2 gene is also expressed in a number of prostate cancer cell lines (FIG. 7). These results indicate that the 20P1F12/TMPRSS2 gene is a predominantly prostate specific gene which may be involved in the development and/or progression of prostate cancer. Moreover, high level expression of 20P1F12/TMPRSS2 was detected by Northern blot in a number of colon carcinoma cell lines (FIG. 7). In addition, high level expression of 20P1F12/TMPRSS2 was detected by immunohistochemical analysis in a number of prostate and colon cancer samples (see e.g. FIG. 17 and Table 1). Table 1 further shows that an anti-20P1F12/TMPRSS2 can be used to identify differences in the predominant staining localization of 20P1F12/TMPRSS2 in cancerous and non-cancerous tissues. This data in Table 1 is consistent with other data presented herein that indicates that 20P1F12/TMPRSS2 is a secreted molecule having a physiological role in invasion and metastases. Consequently, this data provides evidence that the expression of 20P1F12/TMPRSS2 in prostate and colon cancers can provide a molecular basis for detecting, diagnosing, prognosing and/or treating these cancers.

Thus, the invention provides a unique and useful 20P1F12/TMPRSS2 gene (and protein), having the nucleotide and encoded amino acid sequences as shown in FIG. 1. Nucleotide probes corresponding to all or part of the 20P1F12/TMPRSS2 cDNA sequences disclosed herein are provided and may be used to isolate or identify other cDNAs encoding all or part of the 20P1F12/TMPRSS2 gene sequence. The invention further provided primers capable of specifically amplifying the 20P1F12/TMPRSS2 gene or its RNA transcripts. The invention further provides isolated polynucleotides containing coding sequences of the 20P1F12/TMPRSS2 gene product(s). Such polynucleotides may be used to express 20P1F12/TMPRSS2 encoded proteins and peptides having a number of further uses. 20P1F12/TMPRSS2 gene probes and primers may also be used to detect the presence or absence of 20P1F12/TMPRSS2 mRNA in various biological samples, for detecting prostate cancer cells and other cells expressing 20P1F12/TMPRSS2, for generating tumor vaccines, and in molecular diagnostic and prognostic assays for prostate cancer. Polynucleotides corresponding or complementary to the 20P1F12/TMPRSS2 gene may be useful in methods for treating prostate cancer, such as, for example, in modulating 20P1F12/TMPRSS2 biological activity.

More specifically, a 20P1F12/TMPRSS2 polynucleotide useful in the practice of the invention may comprise a polynucleotide having the nucleotide sequence of human 20P1F12/TMPRSS2 as shown in FIG. 1 (SEQ ID NO: 1) or the nucleotide sequence of the previously reported TMPRSS2 as shown in FIG. 2 (SEQ ID NO: 3), a sequence complementary to either of the foregoing, or a polynucleotide fragment of any of the foregoing. Another embodiment comprises a polynucleotide which encodes the 20P1F12/TMPRSS2 protein amino acid sequence as shown in FIG. 1 (SEQ ID NO: 2), a sequence complementary thereto, or a polynucleotide fragment thereof. Another embodiment comprises a polynucleotide which capable of hybridizing under stringent hybridization conditions to the 20P1F12/TMPRSS2 cDNA shown in FIG. 1 (SEQ ID NO: 1) or to a polynucleotide fragment thereof.

A typical embodiment of a 20P1F12/TMPRSS2 polynucleotide is a 20P1F12/TMPRSS2 polynucleotide having the sequence shown in FIG. 1. A 20P1F12/TMPRSS2 polynucleotide may comprise a polynucleotide having the nucleotide sequence of human 20P1F12/TMPRSS2 as shown in FIG. 1, wherein T can also be U; a polynucleotide that encodes all or part of the 20P1F12/TMPRSS2 protein; a sequence complementary to the foregoing; or a polynucleotide fragment of any of the foregoing. Another embodiment comprises a polynucleotide having the sequence as shown in FIG. 1, from nucleotide residue number 114 through nucleotide residue number 1589, wherein T can also be U. Another embodiment comprises a polynucleotide encoding a 20P1F12/TMPRSS2 polypeptide whose sequence is encoded by the cDNA contained in the plasmid as deposited with American Type Culture Collection accorded ATCC Designation Number 207097.

Typical embodiments of the invention disclosed herein include 20P1F12/TMPRSS2 polynucleotides containing specific portions of the 20P1F12/TMPRSS2 mRNA sequence (and those which are complementary to such sequences) such as those that encode the protein and fragments thereof. For example, representative embodiments of the invention disclosed herein include: polynucleotides encoding about amino acid 1 to about amino acid 10 of the 20P1F12/TMPRSS2 protein shown in FIG. 1, polynucleotides encoding about amino acid 20 to about amino acid 30 of the 20P1F12/TMPRSS2 protein shown in FIG. 1, polynucleotides encoding about amino acid 30 to about amino acid 40 of the 20P1F12/TMPRSS2 protein shown in FIG. 1, polynucleotides encoding about amino 40 to about amino acid 50 of the 20P1F12/TMPRSS2 protein shown in FIG. 1, polynucleotides encoding about amino acid 50 to about amino acid 60 of the 20P1F12/TMPRSS2 protein shown in FIG. 1, polynucleotides encoding about amino acid 60 to about amino acid 70 of the 20P1F12/TMPRSS2 protein shown in FIG. 1, polynucleotides encoding about amino acid 70 to about amino acid 80 of the 20P1F12/TMPRSS2 protein shown in FIG. 1, polynucleotides encoding about amino acid 80 to about amino acid 90 of the 20P1F12/TMPRSS2 protein shown in FIG. 1 and polynucleotides encoding about amino acid 90 to about amino acid 100 of the 20P1F12/TMPRSS2 protein shown in FIG. 1, etc. Following this scheme, polynucleotides encoding portions of the amino acid sequence of amino acids 100–492 of the 20P1F12/TMPRSS2 protein are typical embodiments of the invention. Polynucleotides encoding larger portions of the 20P1F12/TMPRSS2 protein are also contemplated. For example polynucleotides encoding from about amino acid 1 (or 20 or 30 or 40 etc.) to about amino acid 20, (or 30, or 40 or 50 etc.) of the 20P1F12/TMPRSS2 protein shown in FIG. 1 may be generated by a variety of techniques well known in the art.

Additional illustrative embodiments of 20P1F12/TMPRSS2 polynucleotides include embodiments consisting of a polynucleotide having the sequence as shown in FIG. 1 from about nucleotide residue number 1 through about nucleotide residue number 500, from about nucleotide residue number 500 through about nucleotide residue number 1000, from about nucleotide residue number 1000 through about nucleotide residue number 1500, from about nucleotide residue number 1500 through about nucleotide residue number 1740. Additional illustrative embodiments of the invention disclosed herein include 20P1F12/TMPRSS2 polynucleotide fragments encoding one or more of the biological motifs contained within the 20P1F12/TMPRSS2 protein sequence and discussed below.

In addition to the detection of disregulated cell growth, the polynucleotides of the preceding paragraphs have a number of different specific uses. For example, because the human 20P1F12/TMPRSS2 gene maps to chromosome 21q22, polynucleotides encoding different regions of the 20P1F12/TMPRSS2 protein can be used to characterize cytogenetic abnormalities on chromosome 21, band q22 that have been identified as being associated with various cancers. In particular, a variety of chromosomal abnormalities in 21q22 including rearrangements have been identified as frequent cytogenetic abnormalities in a number of different cancers (see, e.g., Simpson et al., 1997, Oncogene, 14(18): 2149–2157; Desmaze et al., 1997, Cancer Genet. Cytogenet. 97(1): 12–19). Consequently, polynucleotides encoding specific regions of the 20P1F12/TMPRSS2 protein provide new tools that can be used to delineate with a greater precision than previously possible, the specific nature of the cytogenetic abnormalities in this region of chromosome 21 that may contribute to the malignant phenotype. In this context, these polynucleotides satisfy a need in the art for expanding the sensitivity of chromosomal screening in order to identify more subtle and less common chromosomal abnormalities (see, e.g., Evans et al., 1994, Am. J. Obstet. Gynecol. 171(4):1055–1057).

Included within the scope of this aspect of the invention are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the 20P1F12/TMPRSS2 polynucleotides and polynucleotide sequences disclosed herein. For example, antisense technology entails the administration of exogenous oligonucleotides that bind to a target polynucleotide located within the cells. The term "antisense" refers to the fact that such oligonucleotides are complementary to their intracellular targets, e.g., 20P1F12/TMPRSS2. See for example, Jack Cohen, 1988, OLIGODEOXYNUCLEOTIDES, Antisense Inhibitors of Gene Expression, CRC Press; and Synthesis 1:1–5 (1988). The 20P1F12/TMPRSS2 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorthioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide, which is a sulfur transfer reagent. See Iyer, R. P. et al, 1990, J. Org. Chem. 55:4693–4698; and Iyer, R. P. et al., 1990, J. Am. Chem. Soc. 112:1253–1254, the disclosures of which are fully incorporated by reference herein. As described in Example 14 and shown in FIGS. 30 and 31, additional 20P1F12/TMPRSS2 antisense oligonucleotides of the present invention include morpholino antisense oligonucleotides known in the art (see e.g. Partridge et al., 1996, Antisense & Nucleic Acid Drug Development 6: 169–175).

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a 20P1F12/TMPRSS2 polynucleotide in a sample and as a means for detecting a cell expressing a 20P1F12/TMPRSS2 protein. An example of such a probe is a polynucleotide comprising all or part of the human 20P1F12/TMPRSS2 cDNA sequence shown in FIG. 1 (SEQ ID NO: 1). Examples of primer pairs capable of specifically amplifying 20P1F12/TMPRSS2 mRNAs are also described in the Examples which follow. As will be understood by the skilled artisan, a great many different primers and probes may be prepared based on the sequences provided in herein and used effectively to amplify, clone and/or detect a 20P1F12/TMPRSS2 mRNA.

The 20P1F12/TMPRSS2 polynucleotides of the invention are useful for a variety of purposes, including but not limited to their use as probes and primers for the amplification and/or detection of the 20P1F12/TMPRSS2 gene, mRNA, or fragments thereof; as reagents for the diagnosis and/or prognosis of prostate and colon cancer; as coding sequences capable of directing the expression of 20P1F12/TMPRSS2 polypeptides; as tools for modulating or inhibiting the expression of the 20P1F12/TMPRSS2 gene and/or translation of the 20P1F12/TMPRSS2 transcript; and as therapeutic agents.

The invention also provides 20P1F12/TMPRSS2 proteins and polypeptides which may be used, for example, to generate antibodies to various portions of 20P1F12/TMPRSS2 such as the membrane associated and secreted fragments. The invention also provides 20P1F12/TMPRSS2 proteins and polypeptides which may be used, for example, as cancer vaccines. Those skilled in the art understand that antibodies that recognize proteins bind to epitopes of varying size, and a grouping of the order of about six amino acids, contiguous or not, is regarded as a typical number of amino acids in a minimal epitope. See e.g. Hebbes et al., Mol Immunol 1989 September; 26(9):865–73; Schwartz et al., J Immunol 1985 October; 135(4):2598–608. Scanning along the polypeptide sequence as shown in FIG. 1, illustrative polypeptides that can be used to generate antibodies to any portion of the 20P1F12/TMPRSS2 proteins including, for example: a polypeptide containing at least about 6 amino acids of the 20P1F12/TMPRSS2 sequence shown in FIG. 1.

Polypeptides that can be used in the practice of the present invention (e.g. as immunogens or as modulators of invasion) typically consist of a polypeptide containing at least about 6 amino acids of the 20P1F12/TMPRSS2 sequence shown in FIG. 1, including the valine at position 165; a polypeptide containing at least about 6 amino acids of the 20P1F12/TMPRSS2 sequence shown in FIG. 1 including the isoleucine at position 242; a polypeptide containing at least about 6 amino acids of the 20P1F12/TMPRSS2 sequence shown in FIG. 1 including the glutamic acid at position 329; a polypeptide containing at least about 6 amino acids of the 20P1F12/TMPRSS2 sequence shown in FIG. 1 including the lysine at position 449; a polypeptide containing at least about 6 amino acids of the 20P1F12/TMPRSS2 sequence shown in FIG. 1 including the arginine at position 489; and/or a polypeptide containing at least about 6 amino acids of the 20P1F12/TMPRSS2 sequence shown in FIG. 1 including the aspartic acid at position 491. Optionally, such illustrative polypeptide embodiments include any one of the other amino acids shown in FIG. 1, for example, the methionine at position 1.

Additional closely related embodiments include: an isolated polynucleotide encoding at least about 6 amino acids of the 20P1F12/TMPSS2 sequence shown in FIG. 1 including the valine at position 165; a polynucleotide encoding at least about 6 amino acids of the 20P1F12/TMPRSS2 sequence shown in FIG. 1 including the isoleucine at position 242; a polynucleotide encoding at least about 6 amino acids of the 20P1F12/TMPRSS2 sequence shown in FIG. 1 including the glutamic acid at position 329; a polynucleotide encoding at least about 6 amino acids of the 20P1F12/TMPRSS2 sequence shown in FIG. 1 including the lysine at position 449; a polynucleotide encoding at least about 6 amino acids of the 20P1F12/TMPRSS2 sequence shown in FIG. 1 including the arginine at position 489 and/or a polynucleotide encoding at least about 6 amino acids of the 20P1F12/TMPSS2 sequence shown in FIG. 1 including the aspartic acid at position 491. Optionally, such illustrative polynucleotide embodiments encode any one of the other amino acids shown in FIG. 1, for example, the methionine at position 1.

Embodiments of the invention disclosed herein include a wide variety of art accepted variants of 20P1F12/TMPRSS2 proteins such as polypeptides having amino acid insertions, deletions and substitutions. 20P1F12/TMPRSS2 variants can be made using methods known in the art such as site-directed mutagenesis, alanine scanning, and PCR mutagenesis. Site-directed mutagenesis (Carter et al., 1986, Nucl. Acids Res. 13:4331; Zoller et al., 1987, Nucl. Acids Res. 10:6487), cassette mutagenesis (Wells et al., 1985, Gene 34:315), restriction selection mutagenesis (Wells et al., 1986, Philos. Trans. R. Soc. London Ser. A, 317:415) or other known techniques can be performed on the cloned DNA to produce the 20P1F12/TMPRSS2 variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, The Proteins, (W. H. Freeman & Co., N.Y.); Chothia, 1976, J. Mol. Biol., 150:1). If alanine substitution does not yield adequate amounts of variant, an isosteric amino acid can be used.

As discussed above, embodiments of the claimed invention include polypeptides containing less than the 492 amino acid sequence of the 20P1F12/TMPRSS2 protein shown in FIG. 1 (and the polynucleotides encoding such polypeptides). For example, representative embodiments of the invention disclosed herein include polypeptides consisting of about amino acid 1 to about amino acid 10 of the 20P1F12/TMPRSS2 protein shown in FIG. 1, polypeptides consisting of about amino acid 20 to about amino acid 30 of the 20P1F12/TMPRSS2 protein shown in FIG. 1, polypeptides consisting of about amino acid 30 to about amino acid 40 of the 20P1F12/TMPRSS2 protein shown in FIG. 1, polypeptides consisting of about amino acid 40 to about amino acid 50 of the 20P1F12/TMPRSS2 protein shown in FIG. 1, polypeptides consisting of about amino acid 50 to about amino acid 60 of the 20P1F12/TMPRSS2 protein shown in FIG. 1, polypeptides consisting of about amino acid 60 to about amino acid 70 of the 20P1F12/TMPRSS2 protein shown in FIG. 1, polypeptides consisting of about amino acid 70 to about amino acid 80 of the 20P1F12/

TMPRSS2 protein shown in FIG. 1, polypeptides consisting of about amino acid 80 to about amino acid 90 of the 20P1F12/TMPRSS2 protein shown in FIG. 1 and polypeptides consisting of about amino acid 90 to about amino acid 100 of the 20P1F12/TMPRSS2 protein shown in FIG. 1, etc. Following this scheme, polypeptides consisting of portions of the amino acid sequence of amino acids 100–492 of the 20P1F12/TMPRSS2 protein are typical embodiments of the invention. Polypeptides consisting of larger portions of the 20P1F12/TMPRSS2 protein are also contemplated. For example, polypeptides consisting of about amino acid 1 (or 20 or 30 or 40 etc.) to about amino acid 20, (or 30, or 40 or 50 etc.) of the 20P1F12/TMPRSS2 protein in FIG. 1 may be generated by a variety of techniques well known in the art.

Additional illustrative embodiments of the invention disclosed herein include 20P1F12/TMPRSS2 polypeptides containing the amino acid residues of one or more of the domains contained within the 20P1F12/TMPRSS2 polypeptide sequence as shown for example in FIG. 3B (and the polynucleotides encoding these polypeptides). In one embodiment, typical polypeptides of the invention can contain the cytoplasmic domain, about amino acid 1 to about amino acid 84. In another embodiment, typical polypeptides of the invention can contain the transmembrane domain, about amino acid 84 to about amino acid 106. In another embodiment, typical polypeptides of the invention can contain the LDLRA domain, about amino acid 113 to about amino acid 148. In another embodiment, typical polypeptides of the invention can contain the SRCR domain, about amino acid 149 to about amino acid 242. In another embodiment, typical polypeptides of the invention can contain the protease domain, about amino acid 255 to about amino acid 492.

Additional illustrative embodiments of the invention disclosed herein include 20P1F12/TMPRSS2 polypeptides containing the amino acid residues of one or more of the biological motifs contained within the 20P1F12/TMPRSS2 polypeptide sequence as shown in FIG. 1 (and the polynucleotides encoding these polypeptides). In one embodiment, typical polypeptides of the invention can contain one or more of the 20P1F12/TMPRSS2 N-glycosylation sites such as NTSA at residues 213–216 and/or NSSR at residues 249–252. In another embodiment, typical polypeptides of the invention can contain one or more of the 20P1F12/TMPRSS2 Protein Kinase C phosphorylation sites such as TSK at residues 78–80, TSK at residues 447–449, TKK at residues 81–83, SQR at residues 163–165, SSK at residues 232–234, SLR at residues 238–240, SSR at residues 250–252, and/or TQR at residues 407–409. In another embodiment, typical polypeptides of the invention can contain one or more of the 20P1F12/TMPRSS2 casein kinase II phosphorylation sites such as TVYE at residues 35–38, SGIE at residues 116–119 and/or TFND at residues 356–359. In another embodiment, typical polypeptides of the invention can contain one or more of the N-myristoylation sites such as GSPPAI (SEQ ID NO: 30) at residues 6–11, GTVCTS (SEQ ID NO:31) at residues 74–79, GAALAA (SEQ ID NO: 32) at residues 97–102, GSKCSN (SEQ ID NO: 33) at residues 110–115, GVNLNS (SEQ ID NO: 34) at residues 245–250, GGESAL (SEQ ID NO: 35) at residues 258–263, GNVDSC (SEQ ID NO: 36) at residues 432–437, GSGCAK (SEQ ID NO: 37) at residues 462–467, GCAKAY (SEQ ID NO: 38) at residues 464–469 and/or GVYGN (SEQ ID NO: 39) at residues 472–477. In another embodiment, typical polypeptides of the invention can contain the ATP/GTP-containing site motif A (P-loop), ATEEKGKT (SEQ ID NO: 40) at residues 386–393. In another embodiment, typical polypeptides of the invention can contain the LDL-receptor class A (LDLRA) domain signature CINPSNWCDGVSHCPGGEDENRC (SEQ ID NO: 41) at residues 126–148. In another embodiment, typical polypeptides of the invention can contain the Serine proteases, trypsin family, histidine active site VTAAHC (SEQ ID NO: 42) at residues 292–297. In another embodiment, typical polypeptides of the invention can contain the Serine proteases, trypsin family, serine active site DSCQGDSGGPLV (SEQ ID NO: 43) at residues 435–446. Related embodiments of these inventions include polypeptides containing combinations of the different motifs discussed above with preferable embodiments being those which contain no insertions, deletions or substitutions either within the motifs or the intervening sequences of these polypeptides.

Antibodies capable of specifically binding to and identifying 20P1F12/TMPRSS2 proteins or polypeptides may be used to detect the presence of secreted 20P1F12/TMPRSS2 and/or 20P1F12/TMPRSS2 expressing cells in any biological sample, to determine its subcellular location, detect and image prostate cancer cells and prostate tumors, and modulate or inhibit 20P1F12/TMPRSS2 biological activity. Antibodies may also used therapeutically as described further below. Methods for the generation of polyclonal and monoclonal antibodies are well known in the art.

The invention also provides recombinant DNA or RNA molecules containing a 20P1F12/TMPRSS2 polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook et al, 1989, supra).

The invention further provides a host-vector system comprising a recombinant DNA molecule containing a 20P1F12/TMPRSS2 polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 cell). Examples of suitable mammalian cells include various prostate cancer cell lines such as LnCaP, PC-3, DU145, LAPC-4, TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of a 20P1F12/TMPRSS2 may be used to generate 20P1F12/TMPRSS2 proteins or fragments thereof using any number of host-vector systems routinely used and widely known in the art.

A wide range of host-vector systems suitable for the expression of 20P1F12/TMPRSS2 proteins or fragments thereof are available, see for example, Sambrook et al., 1989, Current Protocols in Molecular Biology, 1995, supra. Preferred vectors for mammalian expression include but are not limited to pcDNA 3.1 myc-His-tag (Invitrogen), the retroviral vector pSRαtkneo (Muller et al., 1991, MCB 11:1785) and/or the Tag5 vector (GenHunter Corporation, Nashville, Tenn.). The Tag5 vector is a preferred vector and provides an IgGK secretion signal that can be used to facilitate the production of a secreted 20P1F12/TMPRSS2 protein in transfected cells. Using these expression vectors, 20P1F12/TMPRSS2 may be preferably expressed in several prostate and non-prostate cancer cell lines, including for example 3T3, 293, 293TPC-3, LNCaP and TsuPr1. The host-vector systems of the invention are useful for the production of a 20P1F12/TMPRSS2 protein or fragment thereof. Such host-vector systems may be employed to study the functional properties of 20P1F12/TMPRSS2 and 20P1F12/TMPRSS2 mutations.

Redundancy in the genetic code permits variation in 20P1F12/TMPRSS2 gene sequences. In particular, one skilled in the art will recognize specific codon preferences by a specific host species and can adapt the disclosed sequence as preferred for a desired host. For example, preferred codon sequences typically have rare codons (i.e., codons having a usage frequency of less than about 20% in known sequences of the desired host) replaced with higher frequency codons. Codon preferences for a specific organism may be calculated, for example, by utilizing codon usage tables available on the Internet at the following address: "www.dna.affrc.go.jp/~nakamura/codon.html." Nucleotide sequences that have been optimized for a particular host species by replacing any codons having a usage frequency of less than about 20% are referred to herein as "codon optimized sequences."

In addition to the detection of disregulated cell growth, proteins encoded by the 20P1F12/TMPRSS2 genes, or by fragments thereof, will have a variety of uses, including but not limited to generating antibodies and in methods for identifying ligands and other agents and cellular constituents that bind to a 20P1F12/TMPRSS2 gene product. Such proteins may also be used as cancer vaccines. Antibodies raised against a 20P1F12/TMPRSS2 protein or fragment thereof may be useful in diagnostic and prognostic assays, imaging methodologies (including, particularly, cancer imaging), and therapeutic methods in the management of human cancers characterized by expression of a 20P1F12/TMPRSS2 protein, such as prostate and colon cancers. Various immunological assays useful for the detection of 20P1F12/TMPRSS2 proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting prostate cells (e.g., in radioscintigraphic imaging methods).

In a specific embodiment, a novel 20P1F12/TMPRSS2 protein having the amino acid sequence of human 20P1F12/TMPRSS2 is provided in FIG. 1 (SEQ ID NO: 2). Fusion proteins which combine all or part of 20P1F12/TMPRSS2 with a heterologous polypeptide are also contemplated and a representative embodiment where the heterologous polypeptide is glutathione-s-synthetase transferase is provided in Example 5. In another typical embodiment, the chimeric molecule may comprise a fusion of the 20P1F12/TMPRSS2 with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 20P1F12/TMPRSS2 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jul. 27, 1995. A variety of fusion polypeptides are well known in the art and typical embodiments are described in Current Protocols In Molecular Biology, Units 9 and 16, Frederick M. Ausubul et al. eds., 1995.

The 20P1F12/TMPRSS2 protein of the invention may be embodied in many forms, preferably in isolated form. As used herein, the protein is said to be "isolated" when physical, mechanical or chemical methods are employed to remove the 20P1F12/TMPRSS2 protein from cellular constituents that are normally associated with the protein. A skilled artisan can readily employ standard purification methods to obtain an isolated 20P1F12/TMPRSS2 protein. A purified 20P1F12/TMPRSS2 protein molecule will be substantially free of other proteins or molecules which impair the binding of 20P1F12/TMPRSS2 to antibody or other ligand. The nature and degree of isolation and purification will depend on the intended use. Embodiments of a 20P1F12/TMPRSS2 protein include a purified 20P1F12/TMPRSS2 protein and a functional, soluble 20P1F12/TMPRSS2 protein. In one form, such functional, soluble 20P1F12/TMPRSS2 proteins or fragments thereof retain the ability to bind antibody, ligand binding partner and/or substrate (e.g. a proteolytic target).

Nucleic acids that encode 20P1F12/TMPRSS2 or its modified forms can also be used to generate either transgenic animals or "knock out" animals (or cell lines) which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding 20P1F12/TMPRSS2 can be used to clone genomic DNA encoding 20P1F12/TMPRSS2 in accordance with established techniques and the genomic sequences used to generate transgenic animals that contain cells that express DNA encoding 20P1F12/TMPRSS2. Methods for generating transgenic animals, particularly animals such as mice or rats, have become conventional in the art and are described, for example, in U.S. Pat. Nos. 4,736,866 and 4,870,009. Typically, particular cells would be targeted for 20P1F12/TMPRSS2 transgene incorporation with tissue-specific enhancers. Transgenic animals that include a copy of a transgene encoding 20P1F12/TMPRSS2 introduced into the germ line of the animal at an embryonic stage can be used to examine the effect of increased expression of DNA encoding 20P1F12/TMPRSS2. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of 20P1F12/TMPRSS2 can be used to construct a 20P1F12/TMPRSS2 "knock out" animal that has a defective or altered gene encoding 20P1F12/TMPRSS2 as a result of homologous recombination between the endogenous gene encoding 20P1F12/TMPRSS2 and altered genomic DNA encoding 20P1F12/TMPRSS2 introduced into an embryonic cell of the animal. For example, cDNA encoding 20P1F12/TMPRSS2 can be used to clone genomic DNA encoding 20P1F12/TMPRSS2 in accordance with established techniques. A portion of the genomic DNA encoding 20P1F12/TMPRSS2 can be deleted or replaced with another gene, such as a gene encoding a selectable marker that can be used to monitor integration. Typically, several kilobases of unaltered flanking DNA (both at the 5' and 3' ends) are included in the vector (see e.g., Thomas and Capecchi, 1987, Cell 51:503, for a description of homologous recombination vectors). The vector is introduced into an embryonic stem cell line (e.g., by electroporation) and cells in which the introduced DNA has homologously recombined with the endogenous DNA are selected (see e.g., Li et al., 1992, Cell 69:915). The selected cells are then injected into a blastocyst of an animal (e.g., a mouse or rat) to form aggregation chimeras (see e.g., Bradley, in Robertson, ed., 1987, Teratocarcinomas and Embryonic Stem Cells: A Practical Approach, (IRL, Oxford), pp. 113–152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the 20P1F12/TMPRSS2 polypeptide.

Recombinant methods can be used to generate nucleic acid molecules that encode the 20P1F12/TMPRSS2 protein. In this regard, 20P1F12/TMPRSS2-encoding nucleic acid molecules described herein provide means for generating defined fragments of the 20P1F12/TMPRSS2 protein. Such 20P1F12/TMPRSS2 polypeptides are particularly useful in generating domain specific antibodies (e.g., antibodies recognizing a predominantly secreted or predominantly membrane associated epitope of the 20P1F12/TMPRSS2 protein), identifying agents or cellular factors that bind to a particular 20P1F12/TMPRSS2 domain, and in various therapeutic contexts, including but not limited to cancer vaccines. 20P1F12/TMPRSS2 polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity.

Another aspect of the invention provides antibodies that immunospecifically bind to the 20P1F12/TMPRSS2 protein and polypeptide fragments thereof. The most preferred antibodies will selectively bind to a 20P1F12/TMPRSS2 protein and will not bind (or will bind weakly) to non-20P1F12/TMPRSS2 proteins and polypeptides. Anti-20P1F12/TMPRSS2 antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule which binds to its target, i.e., the antigen binding region.

For some applications, it may be desirable to generate antibodies which specifically react with a particular 20P1F12/TMPRSS2 protein and/or an epitope within a particular structural domain. For example, preferred antibodies useful for cancer diagnostic imaging purposes are those which react with an epitope in an membrane associated region of the 20P1F12/TMPRSS2 protein as expressed in cancer cells. Such antibodies may be generated by using the 20P1F12/TMPRSS2 protein, or using peptides derived from secreted or other domains of 20P1F12/TMPRSS2, and used as an immunogen.

The 20P1F12/TMPRSS2 antibodies of the invention may be particularly useful in prostate and colon cancer diagnostic and prognostic assays, imaging methodologies, and therapeutic strategies. The invention provides various immunological assays useful for the detection and quantification of 20P1F12/TMPRSS2. Such assays generally comprise one or more 20P1F12/TMPRSS2 antibodies capable of recognizing and binding a 20P1F12/TMPRSS2, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting prostate cancer are also provided by the invention, including but limited to radioscintigraphic imaging methods using labeled 20P1F12/TMPRSS2 antibodies. Such assays may be clinically useful in the detection, monitoring, and prognosis of prostate cancer, particularly advanced prostate cancer.

20P1F12/TMPRSS2 antibodies may also be used in methods for purifying 20P1F12/TMPRSS2 proteins and polypeptides and for isolating 20P1F12/TMPRSS2 homologues and related molecules. For example, in one embodiment, the method of purifying a 20P1F12/TMPRSS2 protein comprises incubating a 20P1F12/TMPRSS2 antibody, which has been coupled to a solid matrix, with a lysate or other solution containing 20P1F12/TMPRSS2 under conditions which permit the 20P1F12/TMPRSS2 antibody to bind to 20P1F12/TMPRSS2; washing the solid matrix to eliminate impurities; and eluting the 20P1F12/TMPRSS2 from the coupled antibody. Other uses of the 20P1F12/TMPRSS2 antibodies of the invention include generating anti-idiotypic antibodies that mimic the 20P1F12/TMPRSS2 protein.

20P1F12/TMPRSS2 antibodies may also be used to for example, modulate or inhibit the biological activity of a 20P1F12/TMPRSS2 protein or target and destroy cells (such as prostate or colon cancer cells) expressing a 20P1F12/TMPRSS2 protein. Antibody therapy of prostate and colon cancer is described in further detail below. A typical embodiment of the invention in this context consists of a method of inhibiting the growth of a precancerous or cancerous cell that expresses 20P1F12/TMPRSS2 comprising contacting the 20P1F12/TMPRSS2 expressed by the neoplastic cell with an effective amount of an anti-20P1F12/TMPRSS2 antibody so that the growth of the neoplastic cell is inhibited. Preferably an antibody used in this method recognizes a 20P1F12/TMPRSS2 epitope that is predominantly cell surface associated. Methods for antibody mediated inhibition and cell lysis are well known in the art and include, for example, complement-mediated or antibody-dependent cell cytotoxicity (ADCC). An alternative embodiment of the invention in this context consists of a method of modulating the biological activity of secreted 20P1F12/TMPRSS2 comprising contacting the secreted 20P1F12/TMPRSS2 an effective amount of an anti-20P1F12/TMPRSS2 antibody so that activity of secreted 20P1F12/TMPRSS2 is modulated. Preferably an antibody used in this method recognizes a 20P1F12/TMPRSS2 epitope that is predominantly secreted.

Various methods for the preparation of antibodies are well known in the art. For example, antibodies may be prepared by immunizing a suitable mammalian host using a 20P1F12/TMPRSS2 protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of 20P1F12/TMPRSS2 may also be used, such as a 20P1F12/TMPRSS2 GST-fusion protein. In a particular embodiment, a GST fusion protein comprising all or most of the open reading frame amino acid sequence of FIG. 1 may be produced and used as an immunogen to generate appropriate antibodies. As described in Example 5, such a GST fusion was used to generate several monoclonal antibodies which immunospecifically react with 20P1F12/TMPRSS2. Cells expressing or overexpressing 20P1F12/TMPRSS2 may also be used for immunizations. Similarly, any cell engineered to express 20P1F12/TMPRSS2 may be used. This strategy may result in the production of monoclonal antibodies with enhanced capacities for recognizing endogenous 20P1F12/TMPRSS2. Additional strategies for generating 20P1F12/TMPRSS2 antibodies are described in Example 5 herein.

The amino acid sequence of 20P1F12/TMPRSS2 as shown in FIG. 1 (SEQ ID NO: 2) may be used to select specific regions of the 20P1F12/TMPRSS2 protein for generating immunogens. For example, hydrophobicity and hydrophilicity analyses of the 20P1F12/TMPRSS2 amino acid sequence may be used to identify hydrophilic regions in the 20P1F12/TMPRSS2 structure. Regions of the 20P1F12/TMPRSS2 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. For example, antibodies that preferentially target a specific 20P1F12/TMPRSS2 species (such as the 32 kD secreted species containing the protease domain or a membrane associated species, see e.g. FIGS. 17 and 22) can be generated by methods discussed below.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a 20P1F12/TMPRSS2 immunogen is conducted generally by injection over a suitable time period and with use of a suitable adjuvant, as is generally understood in the art. During the immunization schedule, titers of antibodies can be taken to determine adequacy of antibody formation.

Anti-20P1F12/TMPRSS2 monoclonal antibodies are preferred and may be produced by various means well known in the art. For example, immortalized cell lines which secrete a desired monoclonal antibody may be prepared using the standard method of Kohler and Milstein or modifications which effect immortalization of lymphocytes or spleen cells, as is generally known. The immortalized cell lines secreting the desired antibodies are screened by immunoassay in which the antigen is the 20P1F12/TMPRSS2 protein or 20P1F12/TMPRSS2 fragment. When the appropriate immortalized cell culture secreting the desired antibody is identified, the cells may be expanded and antibodies produced either from in vitro cultures or from ascites fluid.

The antibodies or fragments may also be produced, using current technology, by recombinant means. Regions that bind specifically to the desired regions of the 20P1F12/TMPRSS2 protein can also be produced in the context of chimeric or CDR grafted antibodies of multiple species origin. Humanized or human 20P1F12/TMPRSS2 antibodies may also be produced and are preferred. Various approaches for producing such humanized antibodies are known, and include chimeric and CDR grafting methods; methods for producing fully human monoclonal antibodies include phage display and transgenic methods (for review, see Vaughan et al., 1998, Nature Biotechnology 16: 535–539).

Fully human 20P1F12/TMPRSS2 monoclonal antibodies may be generated using cloning technologies employing large human Ig gene combinatorial libraries (i.e., phage display)(Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45–64 (1993); Burton and Barbas, Human Antibodies from combinatorial libraries. Id., pp 65–82). Fully human 20P1F12/TMPRSS2 monoclonal antibodies may also be produced using transgenic mice engineered to contain human immunoglobulin gene loci as described in PCT Patent Application WO98/24893 to Kucherlapati et al., published Dec. 3, 1997 (see also Jakobovitis, 1998, Exp. Opin. Invest. Drugs 7(4): 607–614). This method avoids the in vitro manipulation required with phage display technology and efficiently produces high affinity authentic human antibodies.

Reactivity of 20P1F12/TMPRSS2 antibodies with a 20P1F12/TMPRSS2 protein may be established by a number of well known means, including Western blot, immunoprecipitation, ELISA, and FACS anlayses using, as appropriate, 20P1F12/TMPRSS2 proteins, peptides, 20P1F12/TMPRSS2-expressing cells or extracts thereof.

A 20P1F12/TMPRSS2 antibody or fragment thereof of the invention may be labeled with a detectable marker or conjugated to a second molecule, such as a cytotoxic or therapeutic agent, and used for targeting a 20P1F12/TMPRSS2 positive cell (Vitetta, E. S. et al., 1993, Immunotoxin therapy, in DeVita, Jr., V. T. et al., eds, Cancer: Principles and Practice of Oncology, 4th ed., J. B. Lippincott Co., Philadelphia, 2624–2636). A variety of suitable diagnostic and therapeutic conjugates are well known in the art and include, but are not limited to, a radioisotope such as an α-emitter, a-fluorescent compound, a bioluminescent compound, chemiluminescent compound, a metal chelator or a polypeptide such as an enzyme. Typical conjugates are described for example in Current Protocols In Molecular Biology, Units 11 and 17, Frederick M. Ausubul et al. eds., 1995. In preferable embodiments of the invention, the diagnostic and therapeutic conjugates are coupled to an antibody which recognizes a 20P1F12/TMPRSS2 epitope that is predominantly cell-surface associated.

Typical specific embodiments of the antibodies of the invention are described in Example 5 below. As discussed in Example 5, using the methods described herein hybridomas were generated which produce the monoclonal antibodies designated 1F9 (IgG1, K), 2D10 (IgG1, K), 2F8 (IgG1, K), 6B11 (IgG1, K), 3G3 (IgG1, K), 8C6 (IgG1, K) and 9G8 (IgG2a, K). Therefore specific antibody embodiments of the invention include a monoclonal antibody, the epitope combining site of which competitively inhibits essentially all of the epitope binding of monoclonal antibody 1F9, 2D10, 2F8, 6B11, 3G3, 8C6 and/or 9G8. Related specific embodiments of the invention include an immunoconjugate comprising a molecule containing the antigen-binding region of the 1F9, 2D10, 2F8, 6B11, 3G3, 8C6 and/or 9G8 monoclonal antibody joined to a diagnostic or therapeutic agent.

Additional specific embodiments of the invention which utilize the monoclonal antibodies designated 1F9, 2D10, 2F8, 6B11, 3G3, 8C6 and 9G8 include methods for detecting dysregulated cell growth such as cancer by determining the presence of 20P1F12/TMPRSS2 epitope present in a sample from a mammal comprising using a monoclonal antibody to react with 20P1F12/TMPRSS2 epitope present in the sample, the antibody characterized by immunoglobulin to a 20P1F12/TMPRSS2 epitope, said antibody having an antigen combining site which competitively inhibits the immunospecific binding of an antibody designated 1F9, 2D10, 2F8, 6B11, 3G3, 8C6 and/or 9G8 to its target antigen. Other specific embodiments of the invention which utilize the monoclonal antibodies designated 1F9, 2D10, 2F8, 6B11, 3G3, 8C6 and 9G8 include methods for inhibiting the progression of dysregulated cell growth such as a cancer comprising contacting a 20P1F12/TMPRSS2 epitope with a monoclonal antibody or antigen-binding fragment so that the progression of the cancer is inhibited.

Additional specific embodiments of the invention which utilize the monoclonal antibodies designated 1F9, 2D10, 2F8, 6B11, 3G3, 8C6 and 9G8 include methods for determining the presence of dysregulated cell growth such as a cancer in a biological sample comprising contacting a specimen of said sample with a monoclonal antibody or antigen-binding fragment thereof that specifically binds to a 20P1F12/TMPRSS2 epitope, and detecting the binding of said antibody or fragment to said biological sample.

As discussed in detail below, additional specific embodiments of the invention which utilize the monoclonal antibodies designated 1F9, 2D10, 2F8, 6B11, 3G3, 8C6 and 9G8 include methods for inhibiting dysregulated cell growth such as a cancer in a biological sample comprising contacting a specimen of said sample with a monoclonal antibody or antigen-binding fragment thereof that specifically binds to a 20P1F12/TMPRSS2 epitope, so that dysregulated cell growth is inhibited.

Additional illustrative therapeutic and disgnostic methods of the invention are provided below. These methods merely represent typical embodiments of the invention described herein and do not limit the invention in any way.

ILLUSTRATIVE THERAPEUTIC METHODS OF THE INVENTION

The 20P1F12/TMPRSS2 protein is a serine protease that can be found in both secreted and cell surface associated forms and may be involved in invasion and metastasis of prostate and colon cancer. Accordingly, 20P1F12/TMPRSS2 may be ideal target for therapeutic intervention. As noted herein, 20P1F12/TMPRSS2 is found to occur in a variety of forms or species including secreted and cell associated species. Its secreted protease species are, for example, a potential drug and antibody targets, while membrane associated species are, for example, therapeutic antibody targets. Therefore, the invention provides various immunotherapeutic compositions and methods for treating prostate and colon cancer, including antibody therapy, in vivo vaccines, and ex vivo immunotherapy approaches, which utilize polynucleotides and polypeptides corresponding to 20P1F12/TMPRSS2 and anti-20P1F12/TMPRSS2 antibodies. A typical embodiment of the invention in this context consists of a method of inhibiting the growth of a neoplastic cell that expresses 20P1F12/TMPRSS2 comprising contacting the 20P1F12/TMPRSS2 expressed by the neoplastic cell with an effective amount of an anti-20P1F12/TMPRSS2 antibody so that the growth of the neoplastic cell is inhibited.

In one approach, anti-20P1F12/TMPRSS2 antibodies may be used to treat cancers such as prostate and colon cancer. For example, anti-20P1F12/TMPRSS2 antibody may be introduced into a patient such that the antibody binds to free 20P1F12/TMPRSS2 and modulates its biological activity, thereby leading to the inhibition of invasion of the tumor. Alternatively, anti-20P1F12/TMPRSS2 antibody may be introduced into a patient such that the antibody binds to 20P1F12/TMPRSS2 on prostate or color cancer cells and mediates the destruction of the cells and the tumor. The therapeutic mechanism of action may include complement-mediated cytolysis, antibody-dependent cellular cytotoxicity, altering the physiologic function of 20P1F12/TMPRSS2, and/or the inhibition of ligand binding or signal transduction pathways. Anti-20P1F12/TMPRSS2 antibodies conjugated to toxic agents such as ricin, or to therapeutic agents, may also be used therapeutically to deliver the toxic or therapeutic agent directly to 20P1F12/TMPRSS2-bearing prostate tumor cells and thereby destroy the tumor.

Prostate cancer immunotherapy using anti-20P1F12/TMPRSS2 antibodies may follow the teachings generated from various approaches which have been successfully employed with respect to other types of cancer, including but not limited to colon cancer (Arlen et al., 1998, Crit Rev Immunol 18: 133–138), multiple myeloma (Ozaki et al., 1997, Blood 90: 3179–3186; Tsunenari et al., 1997, Blood 90: 2437–2444), gastric cancer (Kasprzyk et al., 1992, Cancer Res 52: 2771–2776), B-cell lymphoma (Funakoshi et al., 1996, J Immunther Emphasis Tumor Immunol. 19: 93–101), leukemia (Zhong et al., 1996, Leuk Res 20: 581–589), colorectal cancer (Moun et al., 1994, Cancer Res 54: 6160–6166); Velders et al., 1995, Cancer Res 55: 4398–4403), and breast cancer (Shepard et al., 1991, J Clin Immunol 11: 117–121).

20P1F12/TMPRSS2 antibodies may be introduced into a patient such that the antibody binds to 20P1F12/TMPRSS2 on the cancer cells and mediates the destruction of the cells and the tumor and/or inhibits the growth of the cells or the tumor. Mechanisms by which such antibodies exert a therapeutic effect may include complement-mediated cytolysis, antibody dependent cellular cytotoxicity, modulating the physiologic function of 20P1F12/TMPRSS2, including ligand binding or signal transduction pathways, modulating tumor cell differentiation, altering tumor angiogenesis factor profiles, and/or by inducing apoptosis. 20P1F12/TMPRSS2 antibodies conjugated to toxic or therapeutic agents may also be used therapeutically to deliver the toxic or therapeutic agent directly to 20P1F12/TMPRSS2-bearing tumor cells.

Although 20P1F12/TMPRSS2 antibody therapy may be useful for all stages of the foregoing cancers, antibody therapy may be particularly appropriate in advanced or metastatic prostate and colon cancers. Combining the antibody therapy method of the invention with a chemotherapeutic or hormone therapy regimen may be preferred in patients who have not received chemotherapeutic treatment, whereas treatment with the antibody therapy of the invention may be indicated for patients who have received one or more chemotherapeutic treatments. Additionally, antibody therapy may also enable the use of reduced dosages of concomitant hormone or chemotherapy, particularly in patients that do not tolerate the toxicity of the chemotherapeutic agent very well.

It may be desirable for patients to be evaluated for the presence and level of 20P1F12/TMPRSS2, preferably using immunohistochemical assessments of tumor tissue, quantitative 20P1F12/TMPRSS2 imaging, or other techniques capable of reliably indicating the presence and degree of expression. Immunohistochemical analysis of tumor biopsies or surgical specimens may be preferred for this purpose. Methods for immunohistochemical analysis of tumor tissues are well known in the art.

Anti-20P1F12/TMPRSS2 antibodies useful in treating prostate, colon and other cancers include those which are capable of initiating a potent immune response against the tumor and those which are capable of direct cytotoxicity. In this regard, anti-20P1F12/TMPRSS2 mAbs such as those discussed in Example 5 may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, anti-20P1F12/TMPRSS2 mAbs which exert a direct biological effect on tumor growth are useful in the practice of the invention. Potential mechanisms by which such directly cytotoxic mAbs may act include inhibition of cell growth, modulation of cellular differentiation, modulation of tumor angiogenesis factor profiles, and the induction of apoptosis. The mechanism by which a particular anti-20P1F12/TMPRSS2 mAbs exerts an anti-tumor effect may be evaluated using any number of in vitro assays designed to determine ADCC and complement-mediated cell lysis, as well as growth inhibition, modulation of apoptosis and inhibition of differentiation, and/or inhibition of angiogenesis, as is generally known in the art.

Figure 25:
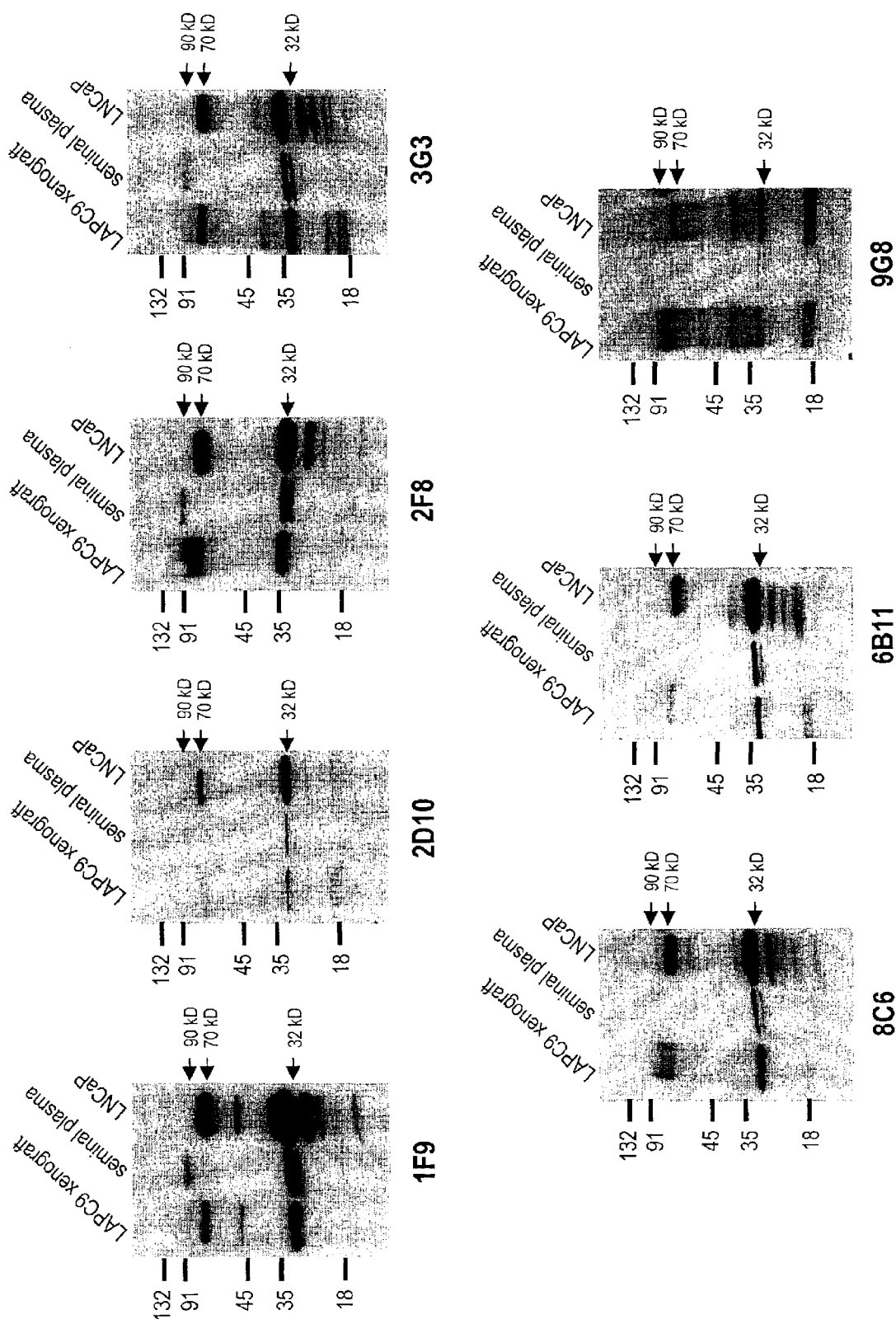
FIG. 25. Detection of 20P1F12/TMPRSS2 protein expression in LAPC9 prostate cancer xenograft, LNCaP prostate cancer cell line, and normal seminal fluid by 7 anti-TMPRSS2 monoclonal antibodies. Tissue lysates of LAPC9 SCID mouse xenograft, mibolerone-stimulated LNCaP cells (10 nM for 48 hours), and normal human seminal plasma were separated by 10–20% SDS-PAGE gradient gel, transferred to nitrocellulose, and subjected to Western analysis with conditioned serum free tissue culture supernatants of 7 anti-TMPRSS2 monoclonal antibody hybridomas as follows. Blots were first blocked for 2 hours at room temperature with TBS (25 mM Tris pH 7.5, 150 mM NaCl)+3% non-fat milk. Blots were then incubated overnight at 4° C. with a 1 to 6 dilution of conditioned serum free hybridoma supernatants in high salt TBS (hTBS; 25 mM Tris pH 7.5, 500 mM NaCl) containing 0.15% Tween 20 (hTBS-T) and 1% non-fat milk. Blots were washed 3X with hTBS-T and then incubated with a 1:4,000 dilution of goat anti-mouse IgG-HRP conjugate in hTBS-T+1% milk for 1 hour at RT. Blots were then washed 3X with hTBS-T. Anti-TMPRSS2 immunoreactive bands were then visualized by enhanced chemiluminescence and exposure to autoradiographic film. Arrows indicate the full length 70 kD 20P1F12/TMPRSS2 protein, the 32 kD auto-catalytic cleavage fragment, and the 90 kD seminal plasma band.

An additional potential mechanism by which antibodies such as 1F9, 2D10, 2F8, 6B11, 3G3, 8C6 and 9G8 may inhibit the progression of cancers such as prostate and colon cancers is by modulating the protease activity of, for example, the 32 kD 20P1F12/TMPRSS2 species found in the sera of individuals suffering from prostate and colon cancer (see e.g. FIGS. 23 and 25). This finding that a secreted form of 20P1F12/TMPRSS2 is found in the sera of individuals suffering from prostate and colon cancer provides evidence that this molecule can be targeted by extracellular therapeutics. In this context, the use of antibodies to inhibit protease function associated with oncogenic processes has been shown to inhibit oncogenic processes such as metastases (see e.g. Mueller et al., P.N.A.S. 89(24): 11832–11836 (1992); Waghray et al., Clin. Cancer Res. 1(7): 747–753 (1995)). In addition to antibodies, small molecules which modulate protease activity can also inhibit the progression of oncogenic processes and may be useful for, for example, anti-metastatic therapy in patients with various cancers (see e.g. McMillan et al., Int. J. Cancer 67(4): 523–531 (1996); Morikawa et al., Nippon Ika Daigaku Zasshi 62(4): 320–328 (1995)). The rational design of protease inhibitors is known in the art (see e.g. Wagner et al., J. Med. Chem. 41(19): 3664–3674 (1998); LaLonde et al., J. Med. Chem. 41(23): 4567–4576 (1998)). In addition, the observed auto-catalytic cleavage (see Example 10 below) may be exploited to identify small molecules that inhibit 20P1F12/TMPRSS2 activity. Specifically, cells may be grown in the presence or absence of small molecule inhibitors to specifically look for inhibition of cleavage. Moreover, the identification of molecules which may interact with 20P1F12/TMPRSS2 is discussed in detail below.

The anti-tumor activity of a particular anti-20P1F12/TMPRSS2 antibody, small molecule, or combination of such molecules, may be evaluated in vivo using a suitable animal model. For example, xenogenic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3: 402–408). For Example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastatses characteristic of late stage disease. Efficacy may be predicted using inhibition of tumor formation, tumor regression, metastasis, and the like.

It should be noted that the use of murine or other non-human monoclonal antibodies, human/mouse chimeric mAbs may induce moderate to strong immune responses in some patients. In the most severe cases, such an immune response may lead to the extensive formation of immune complexes which, potentially, can cause renal failure. Accordingly, preferred monoclonal antibodies used in the practice of the therapeutic methods of the invention are those which are either fully human or humanized and which bind specifically to the target 20P1F12/TMPRSS2 antigen with high affinity but exhibit low or no antigenicity in the patient.

The method of the invention contemplates the administration of single anti-20P1F12/TMPRSS2 mAbs as well as combinations, or "cocktails", of different mAbs. Such mAb cocktails may have certain advantages inasmuch as they contain mAbs which exploit different epitope specificity, different effector mechanisms, or combine directly cytotoxic mAbs with mAbs that rely on immune effector functionality. Such mAbs in combination may exhibit synergistic therapeutic effects. In addition, the administration of anti-20P1F12/TMPRSS2 mAbs may be combined with other therapeutic agents or radiation therapy, including but not limited to various chemotherapeutic agents, androgen-blockers, and immune modulators (e.g., IL-2, GM-CSF). The anti-20P1F12/TMPRSS2 mAbs may be administered in their "naked" or unconjugated form, or may have therapeutic or toxic agents conjugated to them.

The anti-20P1F12/TMPRSS2 monoclonal antibodies used in the practice of the method of the invention may be formulated into pharmaceutical compositions comprising a carrier suitable for the desired delivery method. Suitable carriers include any material which when combined with the anti-20P1F12/TMPRSS2 mAbs retains the specificity and anti-tumor function of the antibody and is non-reactive with the subject's immune systems. Examples include, but are not limited to, any of a number of standard pharmaceutical carriers such as sterile phosphate buffered saline solutions, bacteriostatic water, and the like.

The anti-20P1F12/TMPRSS2 antibody formulations may be administered via any route capable of delivering the antibodies to the tumor site. Potentially effective routes of administration include, but are not limited to, intravenous, intraperitoneal, intramuscular, intratumor, intradermal, and the like. The preferred route of administration is by intravenous injection. A preferred formulation for intravenous injection comprises the anti-20P1F12/TMPRSS2 mAbs in a solution of preserved bacteriostatic water, sterile, unpreserved water, and/or diluted in polyvinylchloride or polyethylene bags containing 0.9% sterile Sodium Chloride for Injection, USP. The anti-20P1F12/TMPRSS2 mAb preparation may be lyophilized and stored as a sterile powder, preferably under vacuum, and then reconstituted in bacteriostatic water containing, for example, benzyl alcohol preservative, or in sterile water prior to injection.

Treatment will generally involve the repeated administration of the anti-20P1F12/TMPRSS2 antibody preparation via an acceptable route of administration such as intravenous injection (IV), typically at a dose in the range of about 0.1 to about 10 mg/kg body weight. Doses in the range of 10–500 mg mAb per week may be effective and well tolerated. Based on clinical experience with the Herceptin mAb in the treatment of metastatic breast cancer, an initial loading dose of approximately 4 mg/kg patient body weight IV followed by weekly doses of about 2 mg/kg IV of the anti-20P1F12/TMPRSS2 mAb preparation may represent an acceptable dosing regimen. Preferably, the initial loading dose is administered as a 90 minute or longer infusion. The periodic maintenance dose may be administered as a 30 minute or longer infusion, provided the initial dose was well tolerated. However, as one of skill in the art will understand, various factors will influence the ideal dose regiment in a particular case. Such factors may include, for example, the binding affinity and half life of the mAb or mAbs used, the degree of 20P1F12/TMPRSS2 overexpression in the patient, the extent of circulating shed 20P1F12/TMPRSS2 antigen, the desired steady-state antibody concentration level, frequency of treatment, and the influence of chemotherapeutic agents used in combination with the treatment method of the invention.

Optimally, patients should be evaluated for the level of circulating shed 20P1F12/TMPRSS2 antigen in serum in order to assist in the determination of the most effective dosing regimen and related factors. Such evaluations may also be used for monitoring purposes throughout therapy, and may be useful to gauge therapeutic success in combination with evaluating other parameters (such as serum PSA levels in prostate cancer therapy).

The invention further provides prostate and colon cancer vaccines comprising a 20P1F12/TMPRSS2 protein or fragment thereof. The use of a tumor antigen in a vaccine for generating humoral and cell-mediated immunity for use in anti-cancer therapy is well known in the art and has been employed in prostate cancer using human PSMA and rodent PAP immunogens (Hodge et al., 1995, Int. J. Cancer 63: 231–237; Fong et al., 1997, J. Immunol. 159, 3113–3117). Such methods can be readily practiced by employing a 20P1F12/TMPRSS2 protein, or fragment thereof, or a 20P1F12/TMPRSS2 encoding nucleic acid molecule and recombinant vectors capable of expressing and appropriately presenting the 20P1F12/TMPRSS2 immunogen. In this context, a variety of 20P1F12/TMPRSS2 polypeptides can be used as immunogens including those targeting a specific domain (such as the protease domain in the 32 kD secreted 20P1F12/TMPRSS2 species) or one the biological motifs discussed above. As shown in Example 5 and Table 2, 20P1F12/TMPRSS2 immunogens can generate an immune response to a variety of 20P1F12/TMPRSS2 epitopes.

Viral gene delivery systems may be used to deliver a 20P1F12/TMPRSS2 encoding nucleic acid molecule. Various viral gene delivery systems which can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658–663). Non-viral delivery systems may also be employed by using naked DNA encoding a 20P1F12/TMPRSS2 protein or fragment thereof introduced into the patient (e.g., intramuscularly) to induce an anti-tumor response. In one embodiment, the full-length human 20P1F12/TMPRSS2 cDNA may be employed. In another embodiment, 20P1F12/TMPRSS2 nucleic acid molecules encoding specific cytotoxic T lymphocyte (CTL) epitopes may be employed. CTL epitopes can be determined using specific algorithms (e.g., Epimer, Brown University) to identify peptides within a 20P1F12/TMPRSS2 protein which are capable of optimally binding to specified HLA alleles.

Various ex vivo strategies may also be employed. One approach involves the use of dendritic cells to present 20P1F12/TMPRSS2 antigen to a patient's immune system. Dendritic cells express MHC class I and II, B7 costimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patient's immune systems (Tjoa et al., 1996, Prostate 28: 65–69; Murphy et al., 1996, Prostate 29: 371–380). Dendritic cells can be used to present 20P1F12/TMPRSS2 peptides to T cells in the context of MHC class I and II molecules. In one embodiment, autologous dendritic cells are pulsed with 20P1F12/TMPRSS2 peptides capable of binding to MHC molecules. In another embodiment, dendritic cells are pulsed with the complete 20P1F12/TMPRSS2 protein. Yet another embodiment involves engineering the overexpression of the 20P1F12/TMPRSS2 gene in dendritic cells using various implementing vectors known in the art, such as adenovirus (Arthur et al., 1997, Cancer Gene Ther. 4: 17–25), retrovirus (Henderson et al., 1996, Cancer Res. 56: 3763–3770), lentivirus, adeno-associated virus, DNA transfection (Ribas et al., 1997, Cancer Res. 57: 2865–2869), and tumor-derived RNA transfection (Ashley et al., 1997, J. Exp. Med. 186: 1177–1182).

Anti-idiotypic anti-20P1F12/TMPRSS2 antibodies can also be used in anti-cancer therapy as a vaccine for inducing an immune response to cells expressing a 20P1F12/TMPRSS2 protein. Specifically, the generation of anti-idiotypic antibodies is well known in the art and can readily be adapted to generate anti-idiotypic anti-20P1F12/TMPRSS2 antibodies that mimic an eptiope on a 20P1F12/TMPRSS2 protein (see, for example, Wagner et al., 1997, Hybridoma 16: 33–40; Foon et al., 1995, J. Clin Invest 96: 334–342; Herlyn et al., 1996, Cancer Immunol Immunother 43: 65–76). Such an anti-idiotypic antibody can be used in anti-idiotypic therapy as presently practiced with other anti-idiotypic antibodies directed against tumor antigens.

Genetic immunization methods may be employed to generate prophylactic or therapeutic humoral and cellular immune responses directed against cancer cells expressing 20P1F12/TMPRSS2, particularly colon and prostate cancer cells. Constructs comprising DNA endcoding a 20P1F12/TMPRSS2 protein/immunogen and appropriate regulatory sequences may be injected directly into muscle or skin of an individual, such that the cells of the muscle or skin take-up the construct and express the encoded 20P1F12/TMPRSS2 protein/immunogen. The 20P1F12/TMPRSS2 protein/immunogen may be expressed as a cell surface protein or be screened. Expression of the 20P1F12/TMPRSS2 protein/immunogen results in the generation of prophylactic or therapeutic humoral and cellular immunity against prostate cancer. Various prophylactic and therapeutic genetic immunization techniques known in the art may be used (for review, see information and references published at internet address www.genweb.com).

Typical embodiments of this aspect of the invention consist of a vaccine composition for the treatment of a cancer expressing 20P1F12/TMPRSS2 comprising an immunogenic portion of a 20P1F12/TMPRSS2 polypeptide and a physiologically acceptable carrier. A related aspect of this invention consists of method of modulating the growth of a cell expresising 20P1F12/TMPRSS2 in a patient, comprising administering to the patient an effective amount of the vaccine.

The invention further includes various methods and compositions for inhibiting the binding of 20P1F12/TMPRSS2 to its binding partner or ligand, or its association with other protein(s) as well as methods for inhibiting 20P1F12/TMPRSS2 function. In one approach, recombinant vectors encoding single chain antibodies that specifically bind to 20P1F12/TMPRSS2 may be introduced into 20P1F12/TMPRSS2 expressing cells via gene transfer technologies, wherein the encoded single chain anti-20P1F12/TMPRSS2 antibody is expressed intracellularly, binds to 20P1F12/TMPRSS2 protein, and thereby inhibits its function. Methods for engineering such intracellular single chain antibodies are well known. Such intracellular antibodies, also known as "intrabodies", may be specifically targeted to a particular compartment within the cell, providing control over where the inhibitory activity of the treatment will be focused. This technology has been successfully applied in the art (for review, see Richardson and Marasco, 1995, TIBTECH vol. 13). Intrabodies have been shown to virtually eliminate the expression of otherwise abundant cell surface receptors. See, for example, Richardson et al., 1995, Proc. Natl. Acad. Sci. USA 92: 3137–3141; Beerli et al., 1994, J. Biol. Chem. 289: 23931–23936; Deshane et al., 1994, Gene Ther. 1: 332–337.

Single chain antibodies comprise the variable domains of the heavy and light chain joined by a flexible linker polypeptide, and are expressed as a single polypeptide. Optionally, single chain antibodies may be expressed as a single chain variable region fragment joined to the light chain constan region. Well known intracellular trafficking signals may be engineered into recombinant polynucleotide vectors encoding such single chain antibodies in order to precisely target the expressed intrabody to the desired intracellular compartment. For example, intrabodies targeted to the endoplasmic reticulum (ER) may be engineered to incorporate a leader peptide and, optionally, a C-terminal ER retention signal, such as the KDEL amino acid motif. Intrabodies intended to exert activity in the nucleus may be engineered to include a nuclear localization signal. Lipid moieties may be joined to intrabodies in order to tether the intrabody to the cytosolic side of the plasma membrane. Intrabodies may also be targeted to exert function in the cytosol. For example, cytosolic intrabodies may be used to sequester factors within the cytosol, thereby preventing them from being transported to their natural cellular destination.

In one emboidment, intrabodies may be used to capture 20P1F12/TMPRSS2 in the nucleus, thereby preventing its activity within the nucleus. Nuclear targeting signals may be engineered into such 20P1F12/TMPRSS2 intrabodies in order to achieve the desired targeting. Such 20P1F12/TMPRSS2 intrabodies may be designed to bind specifically to a particular 20P1F12/TMPRSS2 domain. In another embodiment, cystosolic intrabodies that specifically bind to the 20P1F12/TMPRSS2 protein may be used to prevent 20P1F12/TMPRSS2 from gaining access to the nucleus, thereby preventing it from exerting any biological activity within the nucleus (e.g., preventing 20P1F12/TMPRSS2 from forming transcription complexes with other factors).

In order to specifically direct the expression of such intrabodies to particular tumor cells, the transcription of the intrabody may be placed under the regulatory control of an appropriate tumor-specific promoter and/or enhancer. In order to target intrabody expression specifically to prostate, for example, the PSA promoter and/or promoter/enhancer may be utilized (See, for example, U.S. Pat. No. 5,919,652).

In another approach, recombinant molecules that are capable of binding to 20P1F12/TMPRSS2 thereby preventing 20P1F12/TMPRSS2 from accessing/binding to its binding partner(s) or associating with other protein(s) are used to inhibit 20P1F12/TMPRSS2 function. Such recombinant molecules may, for example, contain the reactive part(s) of a 20P1F12/TMPRSS2 specific antibody molecule. In a particular embodiment, the 20P1F12/TMPRSS2 binding domain of a 20P1F12/TMPRSS2 binding partner may be engineered into a dimeric fusion protein comprising two 20P1F12/TMPRSS2 ligand binding domains linked to the Fc portion of a human IgG, such as human IgG1. Such IgG portion may contain, for example, the $C_H2$ and $C_H3$ domains and the hinge region, but not the $C_H1$ domain. Such dimeric fusion proteins may be administered in soluble form to patients suffering from a cancer associated with the expression of 20P1F12/TMPRSS2, including but not limited to prostate and colon cancers, where the dimeric fusion protein specifically binds to 20P1F12/TMPRSS2 thereby blocking 20P1F12/TMPRSS2 interaction with a binding partner. Such dimeric fusion proteins may be further combined into multimeric proteins using known antibody linking technologies.

Within another class of therapeutic approaches, the invention provides various methods and compositions for inhibiting the transcription of the 20P1F12/TMPRSS2 gene. Similarly, the invention also provides methods and compositions for inhibiting the translation of 20P1F12/TMPRSS2 mRNA into protein.

In one approach, a method of inhibiting the transcription of the 20P1F12/TMPRSS2 gene comprises contacting the 20P1F12/TMPRSS2 gene with a 20P1F12/TMPRSS2 antisense polynucleotide as illustrated in Example 14. In another approach, a method of inhibiting 20P1F12/TMPRSS2 mRNA translation comprises contacting the 20P1F12/TMPRSS2 mRNA with an antisense polynucleotide. In another approach, a 20P1F12/TMPRSS2 specific ribozyme may be used to cleave the 20P1F12/TMPRSS2 message, thereby inhibiting translation. Such antisense and ribozyme based methods may also be directed to the regulatory regions of the 20P1F12/TMPRSS2 gene, such as the 20P1F12/TMPRSS2 promoter and/or enhancer elements. Similarly, proteins capable of inhibiting a 20P1F12/TMPRSS2 gene transcription factor may be used to inhibit 20P1F12/TMPRSS2 mRNA transcription. The various polynucleotides and compositions useful in the aforementioned methods have been described above. The use of antisense and ribozyme molecule to inhibit transcription and translation is well known in the art.

Other factors that inhibit the transcription of 20P1F12/TMPRSS2 through interfering with 20P1F12/TMPRSS2 transcriptional activation may also be useful for the treatment of cancers expressing 20P1F12/TMPRSS2. Similarly, factors that are capable of interfering with 20P1F12/TMPRSS2 processing may be useful for the treatment of cancers expressing 20P1F12/TMPRSS2. Cancer treatment methods utilizing such factors are also within the scope of the invention.

Gene transfer and gene therapy technologies may be used for delivering therapeutic polynucleotide molecules to tumor cells synthesizing 20P1F12/TMPRSS2 (i.e., antisense, ribozyme, polynucleotides encoding intrabodies and other 20P1F12/TMPRSS2 inhibitory molecules). A number of gene therapy approaches are known in the art. Recombinant vectors encoding 20P1F12/TMPRSS2 antisense polynucleotides, ribozymes, factors capable of interfering with 20P1F12/TMPRSS2 transcription, and so forth, may be delivered to target tumor cells using such gene therapy approaches.

The above therapeutic approaches may be combined with any one of a wide variety of chemotherapy or radiation therapy regimens. These therapeutic approaches may also enable the use of reduced dosages of chemotherapy and/or less frequent administration, particularly in patients that do not tolerate the toxicity of the chemotherapeutic agent well.

The anti-tumor activity of a particular composition (e.g., antisense, ribozyme, intrabody), or a combination of such compositions, may be evaluated using various in vitro and in vivo assay systems. In vitro assays for evaluating therapeutic potential include cell growth assays, soft agar assays, invasion and angiogenesis assays and other assays indicative of tumor promoting activity, binding assays capable of determining the extent to which a therapeutic composition will inhibit the binding of 20P1F12/TMPRSS2 to a binding partner, etc.

In vivo, the effect of a 20P1F12/TMPRSS2 therapeutic composition may be evaluated in a suitable animal model. For example, xenogenic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3:402–408). For example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy may be predicted using assays that measure inhibition of tumor formation, tumor regression or metastasis, and the like. See, also, the Examples below.

In vivo assays that qualify the promotion of apoptosis may also be useful in evaluating potential therapeutic compositions. In one embodiment, xenografts from bearing mice treated with the therapeutic compositions may be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods may be formulated into pharmaceutical compositions comprising a carrier suitable for the desired delivery method. Suitable carriers include any material that when combined with the therapeutic composition retains the anti-tumor function of the therapeutic composition and is non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Ed., A. Osal, Ed., 1980).

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations may be lyophilized and stored as sterile powders, preferably under vacuum, and then reconstituted in bacteriostatic water containing, for example, benzyl alcohol preservative, or in sterile water prior to injection.

Dosages and administration protocols for the treatment of cancers using the foregoing methods will vary with the method and the target cancer and will generally depend on a number of other factors appreciated in the art.

MODULATION OF INVASION BY 20P1F12/TMPRSS2

As noted above, PSA and 20P1F12/TMPRSS2 share a number of related characteristics, a finding which provides evidence that these two molecules may have similar physiological roles in vivo. In this corner, observations on the biology of PSA can provide insight in to the biology of 20P1F12/TMPRSS2. Interestingly, while the measurement of serum levels of PSA is widely used as a screening tool for prostate cancer, with the exception of data indicating a potential role as an IGFBP-3 protease (Cohen et al., J. Endocrinol. 142: 407–415 (1994)), surprisingly little is known about the role of PSA in cancer.

Recently, a study which systematically evaluated the effects of PSA on endothelial cell proliferation, migration, and invasion found that PSA has anti-invasive/anti-angiogenic properties in vivo (Fortier et al., J. Nat. Cancer Inst. 91(19): 1635–1640(1999)). These findings are consistent with earlier studies which showed that the anti-angiogenic drugs thalidomide and TNP470 induce statistically significant increases in PSA production by prostate cell lines in vitro (Horti et al., Br. J. Cancer 79: 1588–1593 (1999) and that patients with breast tumors and high levels of PSA had a better prognosis than those patients whose tumors had lower PSA levels (Yu et al., Clin. Cancer Research, 4: 1489–1497 (1998)). The anti-tumor effects of PSA described in Fortier et al. may result from its actions as a serine protease, since ACT blocked both its enzymatic activity and its anti-angiogenic activity in vitro. Moreover, these findings are supported by observations that PSA is able to convert Lys-plasminogen to biologically active angiostatin like fragments, and that these fragments inhibited proliferation and tubular formation of human umbilical vein endothelial cells with the same efficacy as angiostatin (Heidtmann et al., Br. J. Cancer 81(8): 1269–1273 (1999)). As a whole, these data provide evidence that elevations of PSA in a variety of malignancies are part of a normal homeostatic process to fight cancer progression and that the administration of PSA as a drug to augment endogenous concentrations could provide a rational therapeutic approach in the treatment of cancer. In addition, 20P1F12/TMPRSS2 data shown in the Figures and presented in the Examples below as well as these studies on PSA demonstrates that 20P1F12/TMPRSS2 also exhibits such anti-invasive activity.

In cancer, the growth of the tumor is dependent on the angiogenic growth of new blood vessels. Angiogenesis is a tightly regulated process, modulated by the dynamic interplay between angiogenic stimulators and inhibitors that control endothelial cell proliferation, migration, and invasion. This concept is reinforced by the earlier discovery of endogenous stimulators of angiogenesis, such as fibroblast growth factors (FGF) and vascular endothelial growth factors (VEGF), and, more recently, by the discovery of endogenous inhibitors of angiogenesis, including the Angiostatin® and Endostatin™ proteins (O'Reilly et al., Cell, 79: 315–328 (1994); O'Reilly et al., Cell, 88: 277–285 (1997); Sim, Angiogenesis, 2: 37–48 (1998)). Preliminary results indicate that increased concentrations of the anti-angiogenic Endostatin™ protein may occur in animals and patients with growing tumors, which may indicate that angiogenesis is taking place (Paciotti et al., Proc. Am. Assoc. Cancer Res.

40: 66 (1999)). These findings as well as the observations with PSA prompted the studies disclosed in Example 13 which provide evidence that increasing 20P1F12/TMPRSS2 concentrations may not be a harbinger of bad news and prostate and colon cancer progression but, rather, may indicate that the body is attempting to fight cancer by producing its own anti-angiogenic proteins.

Figure 27C:
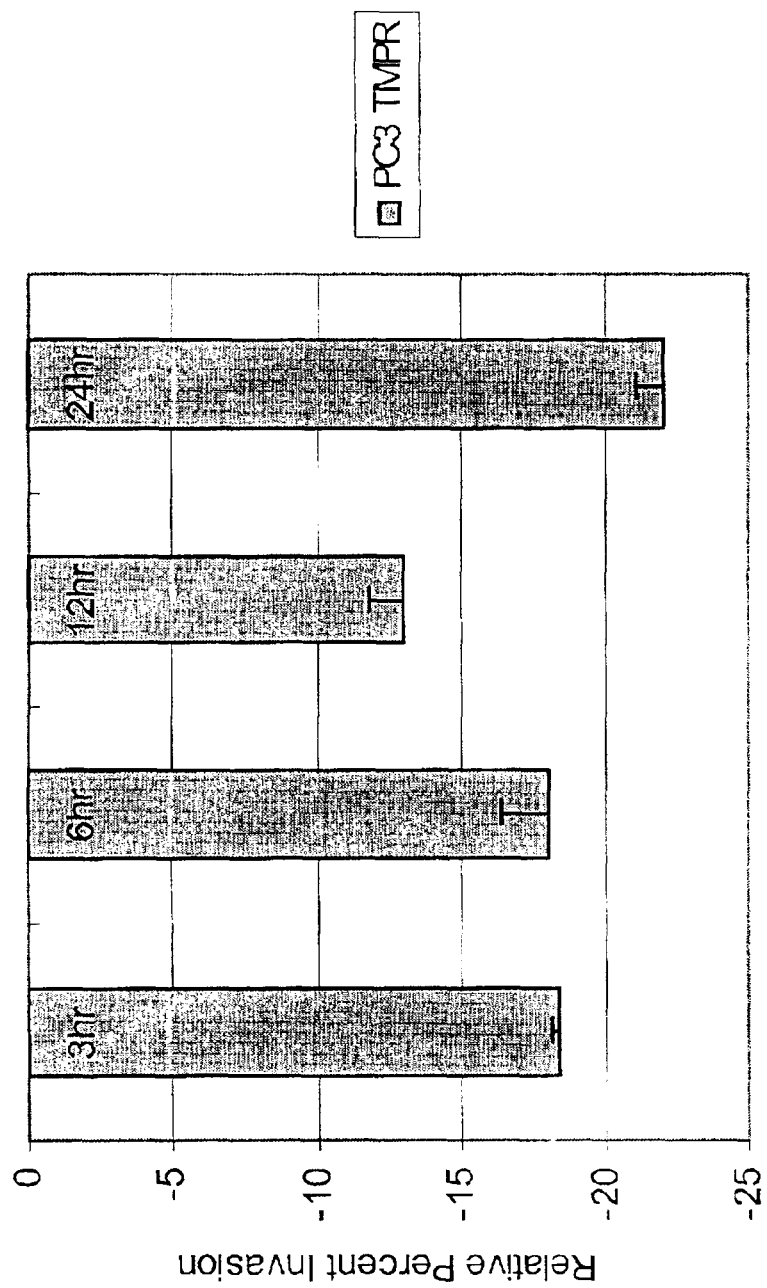
Figure 28:
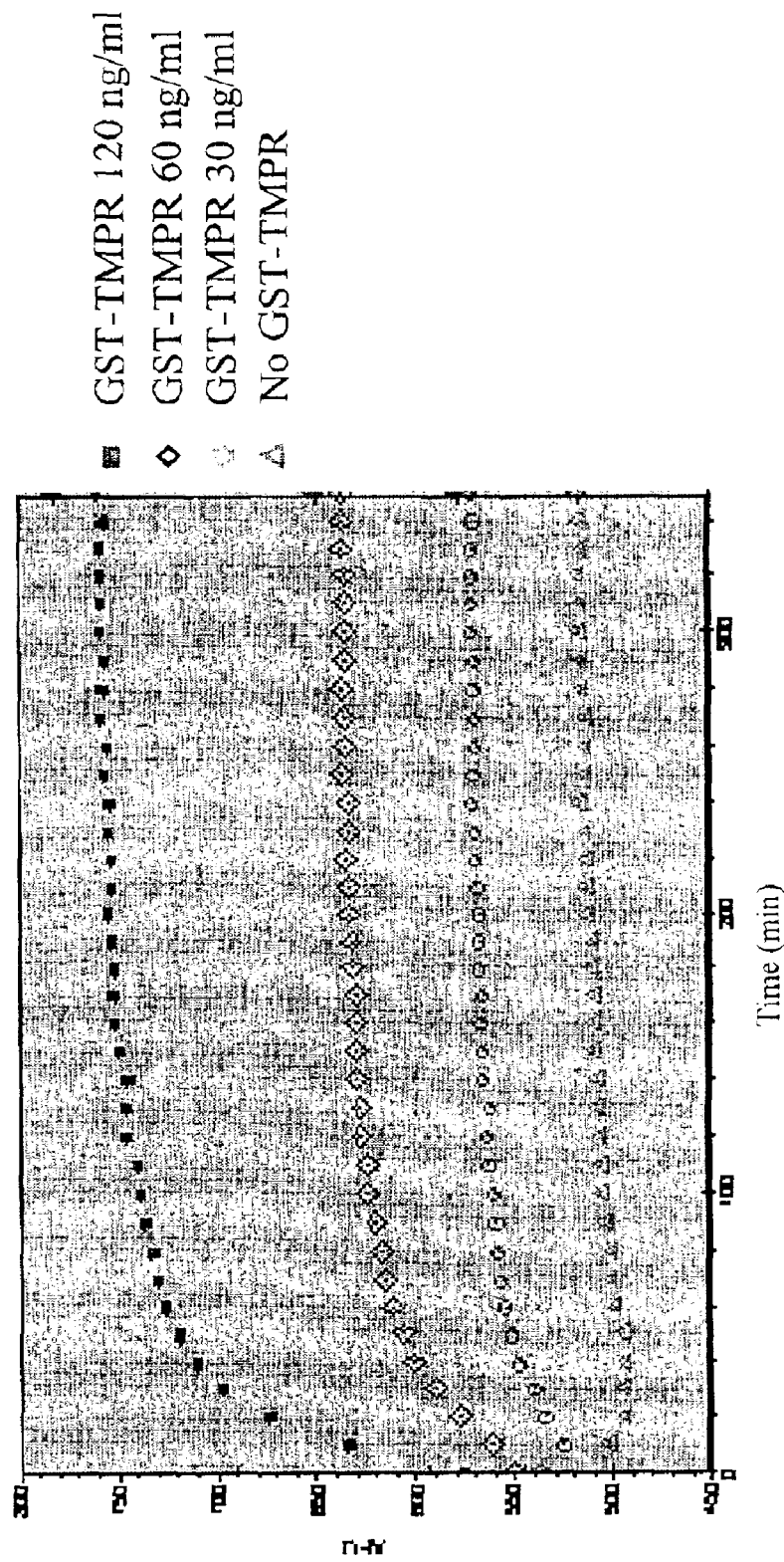
FIG. 28. Protease activity of 20P1F12/TMPRSS2. Purified recombinant GST-20P1F12/TMPRSS2 (aa255-492) was assayed for protease activity using fluorescein thiocarbamoyl-labeled (FTC) casein as a substrate (Molecular Probes). Different doses of GST-20P1F12/TMPRSS2 were incubated at 37° C. with FTC-casein for a total period of 6 hours. Fluorescence was read at 10 minute intervals using a fluorometer. Cleavage of casein by 20P1F12/TMPRSS2 is detected by increased fluorescence. The assay was performed in triplicate.
Figure 29:
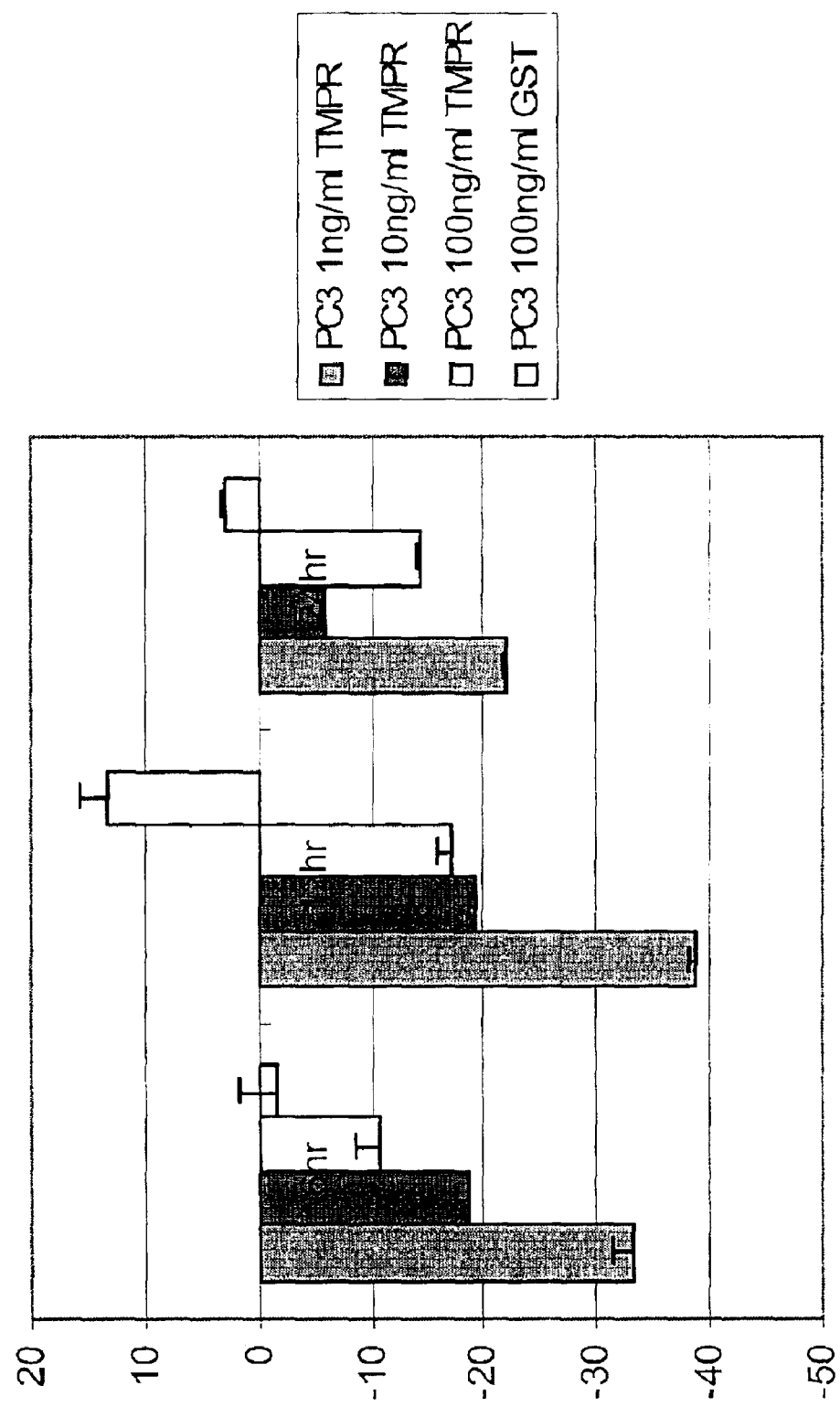
FIG. 29. Effects of purified recombinant 20P1F12/TMPRSS2 fusion protein on invasion. Calcein-loaded PC3 cells were plated in invasion chamber in media alone or in the presence of purified recombinant fusion protein containing the 20P1F12/TMPRSS2 protease domain, i.e. GST-TMPRSS2 (aa 255-492). Purified GST was used as a control. Invasion was determined by measuring the fluorescence of cells in the lower chamber relative to the fluorescence of the entire cell population. The assay was performed in triplicate.
Figure 30:
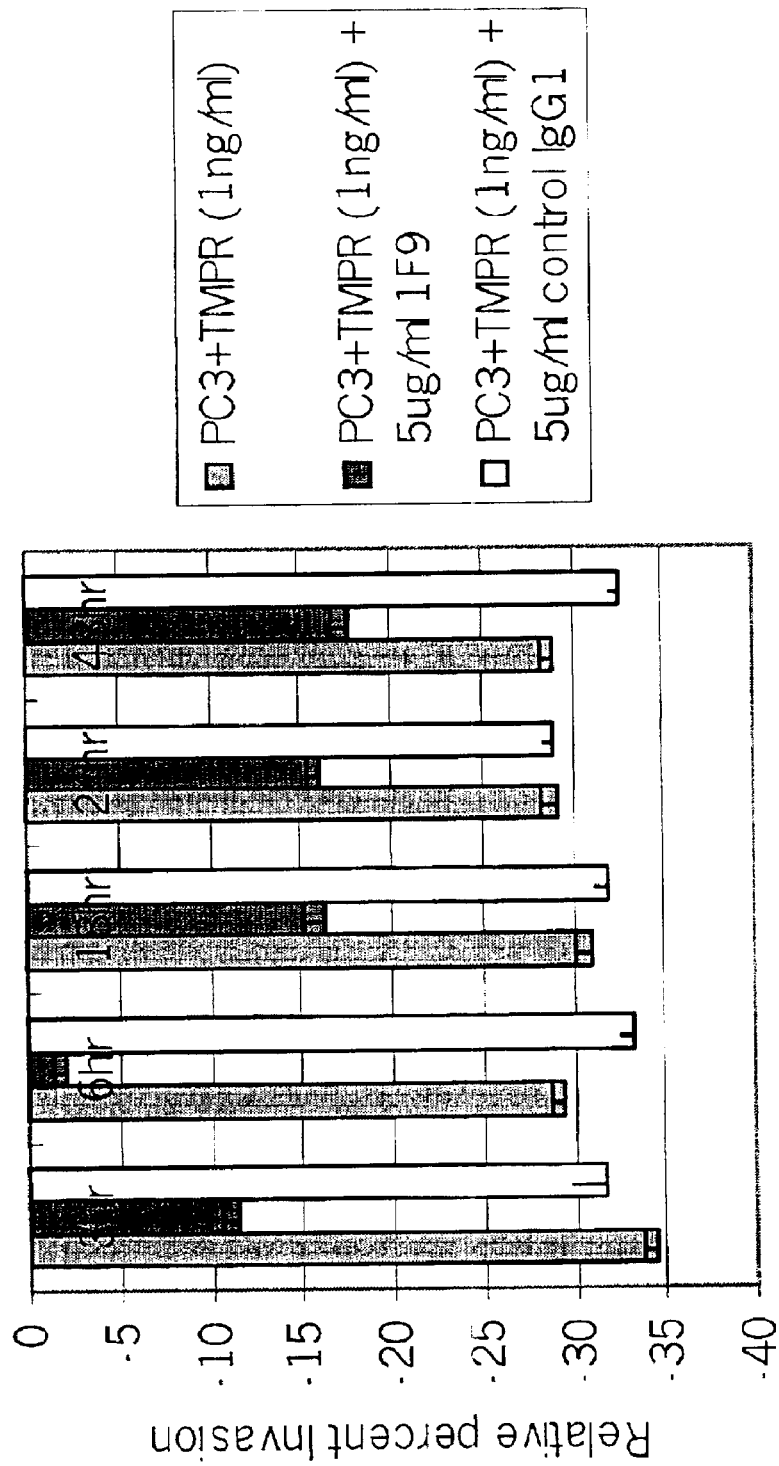
FIG. 30. Calcein-loaded PC3 were plated in invasion chamber in media alone or in the presence of 1 ng/ml purified recombinant 20P1F12/TMPRSS2 fusion protein, i.e. GST-TMPRSS2 (aa 255-492). Control or anti-TMPRSS2 (1F9) mAb were added to the indicated samples. Invasion was determined by measuring the fluorescence of cells in the lower chamber relative to the fluorescence of the entire cell population. The assay was performed in triplicate.

As shown in FIGS. 27–30, like PSA, 20P1F12/TMPRSS2 is a protease which is able to modulate tumor growth and invasion. FIGS. 27A–27C show the differences in the invasive potential of PC3 cells as compared to PC3 cells stably transfected with 20P1F12/TMPRSS2. The data in FIGS. 27A–27C show that cells expressing 20P1F12/TMPRSS2 have reduced invasive capabilities and provides evidence that 20P1F12/TMPRSS2 expression inhibits the invasion of tumors in vivo. In addition, these figures provide comparative data with urokinase-plasminogen activator (see e.g. Rabbani et al., In Vivo. 1998 Jan.–Feb.; 12(1):135–42 Evans et al., Cancer Res. 1997 August 15;57(16):3594–9 and Wilson et al., Anat. Rec. 1997 September;249(1):63–73). FIG. 28 shows the proteolytic activity of 20P1F12/TMPRSS2. Specifically, FIG. 28 illustrates the ability of a 20P1F12/TMPRSS2 fragment (GST-20P1F12/TMPRSS2 (aa255-492)) to cleave casein. FIG. 29 shows the effects of a purified 20P1F12/TMPRSS2 protease fragment on PC3 invasion. The data in FIG. 29 demonstrates how the 20P1F12/TMPRSS2 protease fragment reduces the invasion of PC3 cells through the Matrigel™ basement membrane matrix and provides evidence that the protease domain of 20P1F12/TMPRSS2 can inhibit the invasion of tumors in vivo. FIG. 30 shows how the effects of a purified 20P1F12/TMPRSS2 protease fragment on PC3 invasion are modulated by the anti-20P1F12/TMPRSS2 MAb 1F9. The data in FIG. 30 demonstrates how an anti-20P1F12/TMPRSS2 antibody can abrogate the invasion inhibiting activity of 20P1F12/TMPRSS2 and provides confirmatory evidence that this molecule can inhibit the invasion of tumors in an in vitro model known to correlate with in vivo processes.

The data provided in FIGS. 27–30 show that the 20P1F12/TMPRSS2 is a protease and that this protease reduces the invasion of PC3 cells through the extracellular matrix and that antibodies to the protease domain enhance tumor invasion. Thus this data provides evidence that 20P1F12/TMPRSS2 is a protease that is involved in the modulation of growth of primary tumors as well as metastatic formation. Without being bound by a specific scientific theory, the data presented herein provides evidence that 20P1F12/TMPRSS2 can induce proteolysis of a factor involved with tumor growth, invasion or angiogenesis or can act directly on the tumor or on its environment (e.g. endothelial cells).

The data presented herein provide evidence that like PSA, 20P1F12/TMPRSS2 can serve as both an indicator of cancers such as prostate cancer, as well as a modulator of tumor growth and invasion. Moreover, as invasion is one of the initial steps in metastases formation, this data further provides evidence that 20P1F12/TMPRSS2 can affect angiogenesis. Consequently, methods utilizing 20P1F12/TMPRSS2 may be used to inhibit tumor growth and invasion. In this context, the physiological effect of 20P1F12/TMPRSS2 may be dependent on its status, e.g. whether it is free or complexed with one or more of its binding partners such as those observed in the immunoreactive complexes shown for example in FIG. 24.

A variety of methodologies for using and evaluating the activity of molecules which modulate the invasive and/or angiogenic activity of cells are well known in the art. For example U.S. Pat. No. 6,060,449 discloses an inhibitor of angiogenesis induced by growth of the vascular endothelial cells that comprises Tissue Factor Pathway Inhibitor (TFPI) as an active ingredient. U.S. Pat. No. 6,057,122 discloses mammalian kringle 5 fragments and kringle 5 fusion proteins are disclosed as compound for treating angiogenic diseases. U.S. Pat. No. 6,025,331 discloses pharmaceutical compositions containing therapeutically effective amounts of troponin C, I, or T, subunits, fragments, or analogs for the treatment of diseases or disorders involving abnormal angiogenesis. U.S. Pat. No. 6,024,688 discloses methods for using fragments of an endothelial cell proliferation inhibitor derived from plasminogen, specifically an angiostatin fragment. In addition, U.S. Pat. No. 5,981,484 disclose various peptides that inhibit angiogenesis and are useful in the treatment of disease states such as cancer, arthritis, macular degeneration and diabetic retinopathy in which angiogenesis plays a role. The disclosures of U.S. Pat. Nos. 6,060,449, 6,057,122, 6,025,331, 6,024,688 and 5,981,484 are incorporated herein by reference.

The 20P1F12/TMPRSS2 polypeptides of the invention may be further characterized as producing an inhibitory effect of invasion angiogenesis, on tumor metastasis or on inflammatory reactions. The 20P1F12/TMPRSS2 polypeptides are especially useful for inhibiting invasion in a mammalian host, preferably human, harboring a tumor. The term "invasion" is used according to its art accepted meaning as the physiological process by which a cell such as a tumor cell moves through an extracellular matrix or basement membrane. Invasion is observed in a variety of specific contexts such as in vivo diaphragm invasion assays using SCID mice as well as in vitro assays using reconstituted basement membranes specifically designed to mimic the extracellular matrix that tumor cells disseminate through during metastasis (see e.g. Stearns et al., Cancer Res. 1992, 52(13): 3776–3781 and Knox et al., Prostate 1998, 35(4): 248–254). In addition, invasion can be quantified by a variety of methods known in the art such as those using the Transwell Insert System (Becton Dickinson) described in Example 13.

The foregoing anti-invasive and/or anti-angiogenic compositions and treatment methods are useful for inhibiting cell migration and invasion or migration-induced cell proliferation in a subject having a disease or condition associated with undesired cell invasion, migration-induced proliferation, angiogenesis or metastasis. Such diseases or conditions may include primary growth or solid tumors or leukemias and lymphomas, metastasis, invasion and/or growth of tumor metastases, atherosclerosis, myocardial angiogenesis, post-balloon angioplasty vascular restenosis, neointima formation following vascular trauma, vascular graft restenosis, coronary collateral formation, deep venous thrombosis, ischemic limb angiogenesis, telangiectasia, pyogenic granuloma, corneal diseases, rubeosis, neovascular glaucoma, diabetic and other retinopathy, retrolental fibroplasia, diabetic neovascularization, macular degeneration, endometriosis, arthritis, fibrosis associated with chronic inflammatory conditions including psoriasis scleroderma, lung fibrosis, chemotherapy-induced fibrosis, wound healing with scarring and fibrosis; peptic ulcers, fractures, keloids, and disorders of vasculogenesis, hematopoiesis, ovulation, menstruation, pregnancy and placentation, or any other disease or condition in which invasion or angiogenesis is pathogenic.

Accordingly, this specific aspect of the invention includes methods for inhibiting cellular invasion, chiefly by tumor cells, or angiogenesis, primarily induced by tumor cells in a subject. By inhibiting invasion by cells or angiogenesis, the method results in inhibition of tumor metastasis. In this method, a vertebrate subject, preferably a mammal, more preferably a human, is administered an amount of a 20P1F12/TMPRSS2 molecule that typically comprises a polypeptide having the amino acid sequence set forth in SEQ ID NO:2 or is a biologically active fragment thereof. The 20P1F12/TMPRSS2 polypeptide is preferably administered in the form of a pharmaceutical composition as described above.

Doses of the 20P1F12/TMPRSS2 molecules preferably include pharmaceutical dosage units comprising an effective amount of a 20P1F12/TMPRSS2 polypeptide. By an effective amount is meant an amount sufficient to achieve a steady state concentration in vivo which results in a measurable reduction in any relevant parameter of disease and may include invasion and/or growth of primary or metastatic tumors, any accepted index of inflammatory reactivity, or a measurable prolongation of disease-free interval or of survival. For example, a reduction in tumor growth in 20% of patients is considered efficacious (Frei III, E., Cancer Journal 3:127–136 (1997)). However, an effect of this magnitude is not considered to be a minimal requirement for the dose to be effective in accordance with this invention. Effective does and optimal dose ranges may be determined using the methods known in the art including those described herein.

Alternatively the wide variety of gene transfer and gene therapy technologies known in the art may be used for delivering therapeutic polynucleotide molecules to cells (e.g., a 20P1F12/TMPRSS2 polynucleotide encoding the amino acid sequence set forth in SEQ ID NO:2 or anti-proliferative fragments thereof). A number of gene therapy approaches are known in the art and are described for example in U.S. Pat. Nos.: 5,830,880, 6,071,890 and 5,792,453. Using such well known methods, recombinant vectors encoding such 20P1F12/TMPRSS2 molecules may be delivered to target cells (e.g. tumor and endothelial cells) which will subsequently express 20P1F12/TMPRSS2 as a means of modulating cellular growth, invasion and/or metastasis.

A number of representative methods of using 20P1F12/TMPRSS2 to modulate cellular growth, invasion and/or metastasis are provided herein. In these methods the 20P1F12/TMPRSS2 molecule typically comprises a polypeptide having the amino acid sequence set forth in SEQ ID NO:2 is a biologically active fragment thereof. Typical embodiments of the invention include a method of inhibiting cellular invasion in a mammal comprising administering to the mammal an cellular invasion inhibiting amount of a 20P1F12/TMPRSS2 molecule that the has anti-invasive activity in vivo. Another related embodiment of the invention consists of a method of inhibiting cellular invasion and/or angiogenesis in a mammal comprising administering to the mammal an invasive inhibiting amount of a 20P1F12/TMPRSS2 molecule that has anti-invasive activity, wherein said fragment contains amino acid substitutions and/or deletion, and/or additions of the sequence set forth in SEQ ID NO:2, but retains anti-invasive activity (e.g. a GST fragment comprising amino acid 255–492 of the sequence set forth in SEQ ID NO:2).

A typical embodiment of the invention consists of a method for inhibiting invasion by a tumor cell comprising introducing into the cell's environment a polypeptide comprising the amino acid sequence set forth in SEQ ID NO:2 or anti-invasive fragments thereof, whereby invasion is inhibited. By introducing into the cell's environment it is meant that the polypeptide is placed into the cell's milieu so that it can effect a physiological process of that cell either directly or indirectly. A variety of methods for introducing therapeutics such as polypeptides into a cell's environment are well known in the art with typical methods including intravenous or site specific injection.

Typically the anti-invasive fragment of the 20P1F12/TMPRSS2 polypeptide comprises the protease domain of the 32 KD protease fragment shown for example in FIG. 23. Another illustrative embodiment of such a fragment is the polypeptide comprising amino acids 255–492 of the sequence set forth in SEQ ID NO:2 which is utilized in the anti-invasive assays described in Example 13. In preferred embodiments of this method, the polypeptide is introduced into the cell's environmental parenterally. In typical embodiments, the polypeptide is introduced into the cell's environment by intravenous injection.

One specific embodiment of the invention consists of a method for inhibiting basement membrane invasion by a tumor cell comprising introducing into the cell's environment a polypeptide of SEQ ID NO: 2, whereby basement membrane invasion is inhibited. Preferably the tumor cells in this methods exhibit increased expression or secretion of 20P1F12/TMPRSS2. A related specific embodiment of the invention consists of a method for inhibiting tumor cell invasion wherein said tumor cells exhibiting increased synthesis or secretion of 20P1F12/TMPRSS2, comprising administering a polypeptide of SEQ ID NO: 2, whereby tumor cell invasion is inhibited. In preferred embodiments of these methods, the polypeptide of SEQ ID NO: 2 consists of the 32 kD fragment which contains the 20P1F12/TMPRSS2 protease domain.

Related embodiments of the invention consists of methods of inhibiting tumor cell expansion in a mammal comprising administering to the mammal a sufficient amount of a 20P1F12/TMPRSS2 molecule to inhibit tumor cell expansion such as the expansion of prostate and color tumors, wherein the 20P1F12/TMPRSS2 molecule has an amino acid sequence comprising the amino acid sequence set forth in SEQ ID NO: 2 or anti-proliferative fragments thereof. In a specific embodiment the 20P1F12/TMPRSS2 molecule contains the protease domain or an anti-proliferative fragment thereof.

The skilled artisan understands that the modification of polypeptides can facilitate their use in various contexts. Consequently, in addition to modifications with heterologous polypeptides (see e.g. the immunoglobulin fusion polypeptides discussed above), the present invention further provides 20P1F12/TMPRSS2 variants covalently attached (hereinafter "conjugated") to one or more chemical groups. Such variants can be particularly useful for uses in vivo. Chemical groups suitable for use in an 20P1F12/TMPRSS2 variant conjugate of the present invention are preferably not significantly toxic or immunogenic, i.e., any toxicity or immunogenicity observed with an 20P1F12/TMPRSS2 variant conjugate is not significantly (i.e., less than 50%) greater than any toxicity or immunogenicity observed with the corresponding unmodified 20P1F12/TMPRSS2 variant. Typically, a chemical group is selected that reduces toxicity and/or immunogenicity associated with the unmodified 20P1F12/TMPRSS2 variant. In addition, the chemical group is conveniently selected to produce an 20P1F12/TMPRSS2 variant conjugate that can be stored and used under conditions suitable for storage and use of the unmodified 20P1F12/TMPRSS2 variant. Exemplary chemical groups include carbohydrates, such as, for example, those carbohydrates that occur naturally on glycoproteins, and non-proteinaceous polymers, such as polyols.

A polyol, for example, can be conjugated to an 20P1F12/TMPRSS2 variant molecule at one or more amino acid residues, including lysine residues, as disclosed in WO 93/00109. The polyol employed can be any water-soluble poly(alkylene oxide) polymer and can have a linear or branched chain. Suitable polyols include those substituted at one or more hydroxyl positions with a chemical group, such as an alkyl group having between one and four carbons. Typically, the polyol is a poly(alkylene glycol), such as poly(ethylene glycol) (PET), and thus, for ease of description, the remainder of the discussion relates to an exemplary embodiment wherein the polyol employed is PEG and the process of conjugating the polyol to an 20P1F12/TMPRSS2 variant is termed "pegylation." However, those skilled in the art recognize that other polyols, such as, for example, poly(propylene glycol) and polyethylene-polypropylene glycol copolymers, can be employed using the techniques for conjugation described herein for PEG. The degree of pegylation of an 20P1F12/TMPRSS2 variant of the present invention can be adjusted to provide a desirably increased in vivo half-life (hereinafter "half-life"), compared to the corresponding non-pegylated protein.

A variety of methods for pegylating proteins have been described. See, e.g., U.S. Pat. No. 4,179,337 (issued to Davis et al.), disclosing the conjugation of a number of hormones and enzymes to PEG and polypropylene glycol to produce physiologically active non-immunogenic compositions. Generally, a PEG having at least one terminal hydroxy group is reacted with a coupling agent to form an activated PEG having a terminal reactive group. This reactive group can then react with the α- and ε-amines of proteins to form a covalent bond. Conveniently, the other end of the PEG molecule can be "blocked" with a non-reactive chemical group, such as a methoxy group, to reduce the formation of PEG-crosslinked complexes of protein molecules.

ILLUSTRATIVE DIAGNOSTIC METHODS OF THE INVENTION

As noted above, assays that evaluate the status of 20P1F12/TMPRSS2 (e.g. the status of the 20P1F12/TMPRSS2 gene and gene products such as mRNAs and proteins) in an individual can be used to provide information on the growth or oncogenic potential of cells from the individual. In particular, the finding that 20P1F12/TMPRSS2 mRNA is so highly expressed in prostate and colon cancer lines identifies this gene and its products as targets that the skilled artisan can use to evaluate biological samples from individuals suspected of having a disease associated with alterations in the status of 20P1F12/TMPRSS2.

Because 20P1F12/TMPRSS2 is expressed in various prostate cancer xenograft tissues and cell lines, and is also expressed in some colon cancer cell lines, the expression status of 20P1F12/TMPRSS2 can provide information useful for determining information including the presence, stage and location of displastic, precancerous and cancerous cells, predicting susceptibility to various stages of disease, and/or for gauging tumor aggressiveness. Moreover, the expression profile and cell surface localization of 20P1F12/TMPRSS2 makes it a potential imaging reagent for metastasized disease. Consequently, an important aspect of the invention is directed to the various molecular prognostic and diagnostic methods for examining the status of 20P1F12/TMPRSS2 in biological samples such as those from individuals suffering from, or suspected of suffering from a pathology characterized by disregulated cellular growth such as cancer. Oncogenesis is known to be a multistep process where cellular growth becomes progressively disregulated and cells progress from a normal physiological state to precancerous and then cancerous states (see e.g. Alers et al., Lab Invest. 77(5): 437–438 (1997) and Isaacs et al., Cancer Surv. 23: 19–32 (1995)). In this context, examining a biological sample for evidence of disregulated cell growth (such as aberrant 20P1F12/TMPRSS2 expression in prostate and colon cancers) can allow the early detection of such aberrant cellular physiology before a pathology such as cancer has progressed to a stage at which therapeutic options are more limited. In such examinations, the status of 20P1F12/TMPRSS2 in a biological sample of interest (such as one suspected of having disregulated cell growth) can be compared, for example, to the status of 20P1F12/TMPRSS2 in a corresponding normal sample (e.g. a sample from that individual (or alternatively another individual) that is not effected by a pathology, for example one not suspected of having disregulated cell growth) with alterations in the status of 20P1F12/TMPRSS2 in the biological sample of interest (as compared to the normal sample) providing evidence of disregulated cellular growth. In addition to using a biological sample that is not effected by a pathology as a normal sample, one can also use a predetermined normative value such as a predetermined normal level of mRNA expression (see e.g. Grever et al., J. Comp. Neurol. 1996 December 9;376(2):306–14 and U.S. Pat. No. 5,837,501) to compare 20P1F12/TMPRSS2 in normal versus suspect samples.

Figure 17:
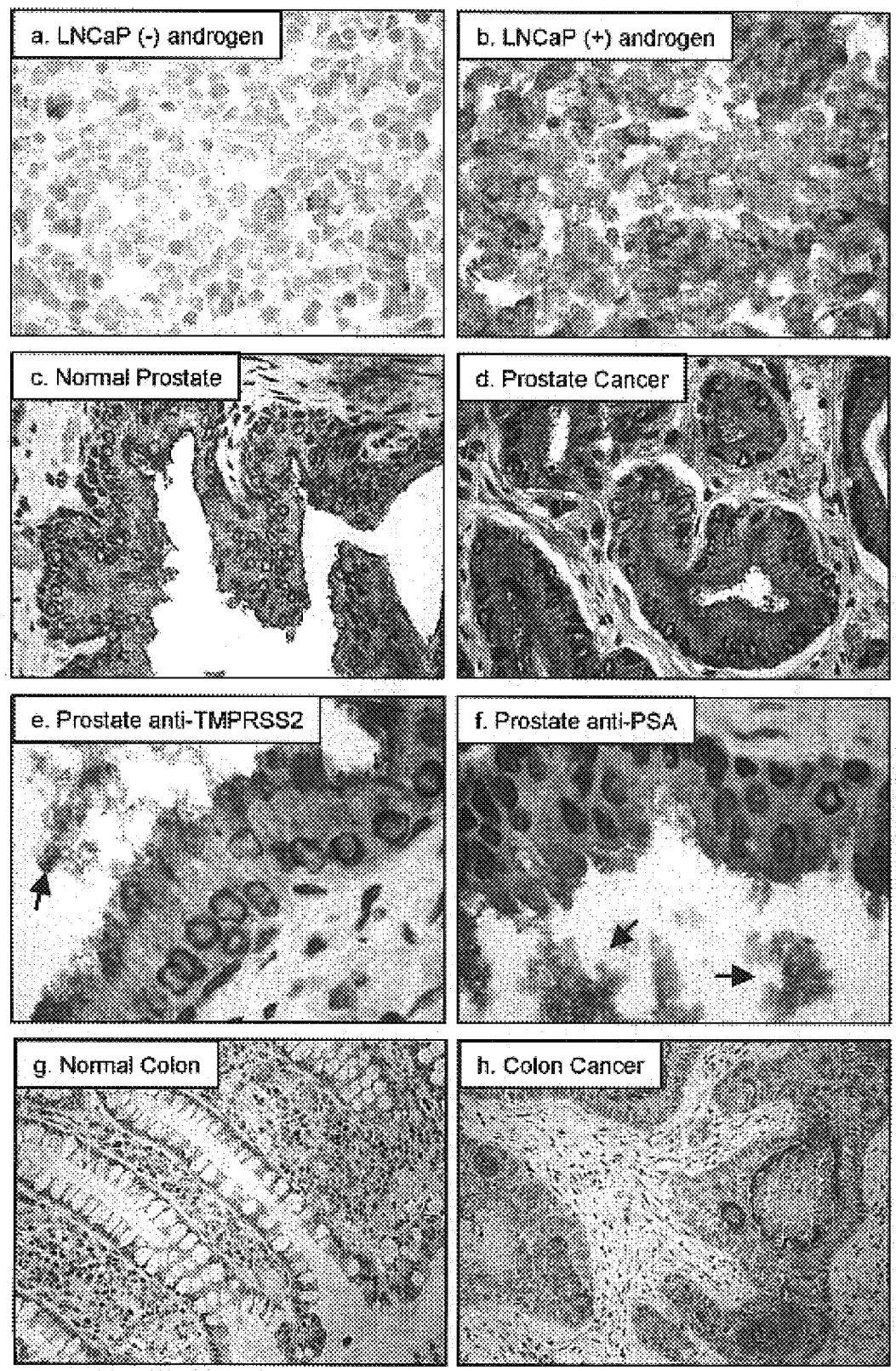
FIG. 17. Immunohistochemical analysis of prostate and colon cancer patient samples with anti-20P1F12/TMPRSS2 MAb. Samples include: (a) LNCaP cells grown in medium containing 2% CSS for 1 week, (b) LNCaP cells grown in medium containing 2% CSS for 1 week and stimulated with mibolerone (10 nM) for 9 hours, (c) normal prostate tissue, (d) grade 3 prostate carcinoma, (e) normal prostate tissue stained with 1F9 (1000×magnification), (f) normal prostate tissue stained with anti-PSA antibodies (1000× magnification), (g) normal colon, (h) colon cancer. Staining of secreted protein within the prostate gland lumen is indicated by the arrows. All pictures are at 400× magnification, except where indicated differently. Comparative observations of, for example, the staining localization of 20P1F12/TMPRSS2 in normal colon and colon cancer, show distinct differences in the accumulation of 20P1F12/TMPRSS2, a finding which provides confirmatory evidence of the use of 20P1F12/TMPRSS2 as a diagnostic and therapeutic target.
Figure 18:
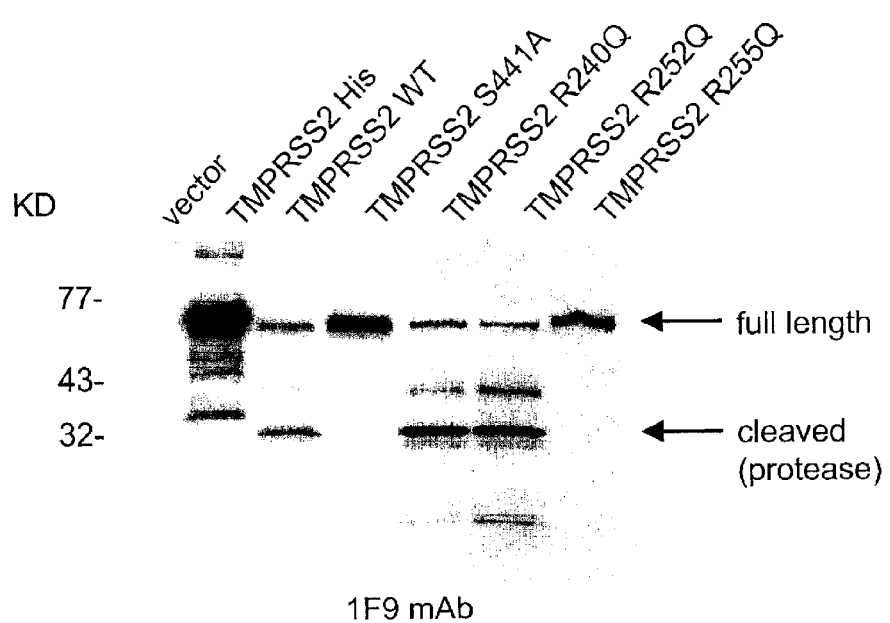
FIG. 18. Mutagenic analysis of 20P1F12/TMPRSS2 reveals auto-catalytic activity and proteolytic cleavage site. 293T cells were transfected with the different 20P1F12/TMPRSS2 point mutants as described in Example 10. Cell lysates (20 µg protein) were probed with 1F MAb. Molecular weight standards are indicated on the side in kilodaltons (KD).
Figure 19:
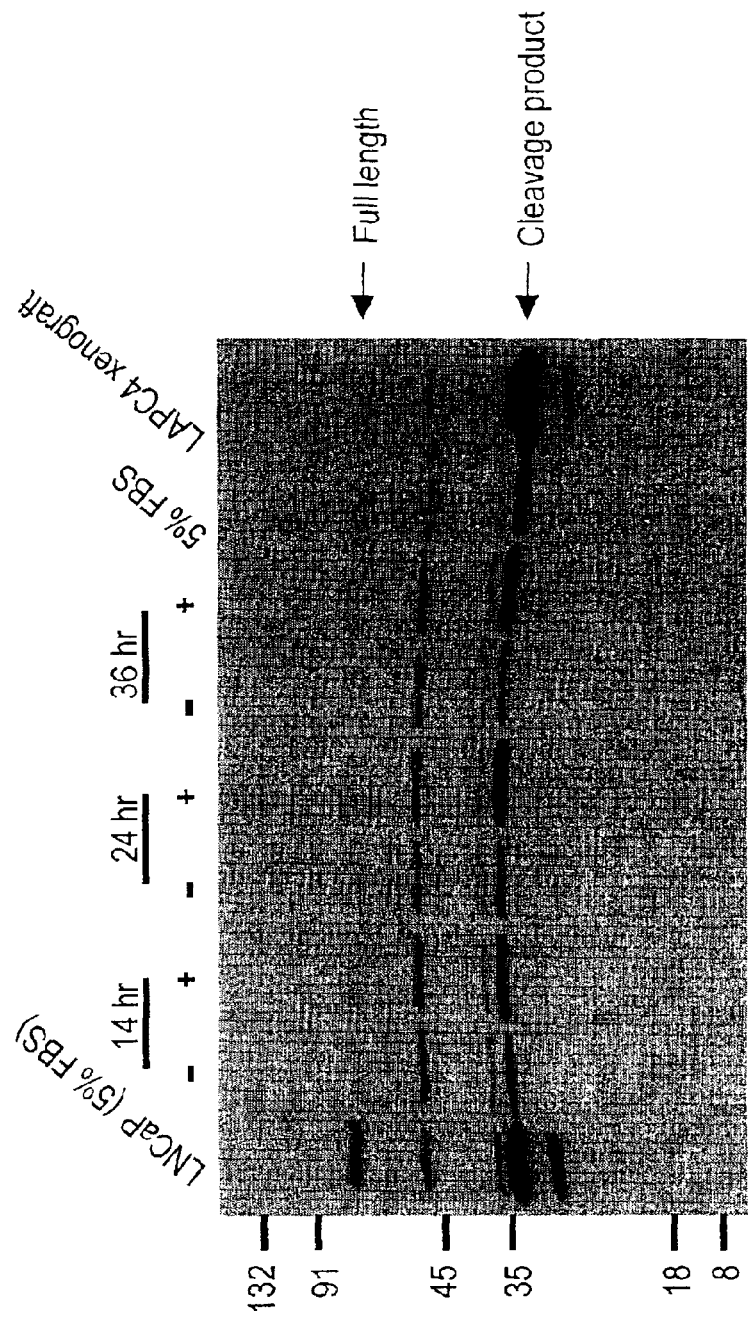
FIG. 19. Increased expression of 20P1F12/TMPRSS2 and of the 32 kD auto-proteolytic cleavage product in LAPC4 cells upon androgen stimulation. 70% confluent LAPC4 cells in 10 cm dishes were starved of androgen by incubating in RPMI media containing 2% charcoal-dextran treated FBS (CD-FBS) for 4 days. Media was then aspirated and replaced with fresh 2% CD-FBS RPMI in the presence or absence of 5 nM of the androgen analog mibolerone. At the indicated time, cells were harvested and lysed in RIPA buffer containing protease inhibitors. For comparison, lysates of LNCaP and LAPC4 cells grown in RPMI+5% FBS and of a whole tissue lysate of an LAPC4 SCID mouse xenograft were included in the analysis. 25 µg/lane of the indicated cell lysate was separated by 10–20% gradient SDS-PAGE, transferred to nitrocellulose and subjected to Western analysis using the anti-TMPRSS2 mAb 1F9 as follows. The blot was first blocked for 2 hours in 25 mM TRIS pH 7.5 and 150 mM NaCl (TBS) containing 3% non-fat milk. The blot was then incubated overnight at 4° C. with 2 µg/ml of 1F9 mAb in high salt TBS (500 mM NaCl+0.15% Tween-20 (hTBS-T) containing 1% milk. The blot was washed with hTBS-T and then incubated for 1 hour at room temperature with a 1:4,000 dilution of goat anti-mouse IgG1-HRP conjugated secondary antibody (Southern Biotechnology) 1 hTBS-T+1% milk. Following washing, anti-TMPRSS2 immunoreactive bands were visualized by enhanced chemiluminescence and exposure to autoradiographic film. Arrows indicate the 70 kD full length 20P1F12/TMPRSS2 protein and the auto-proteolytic 32 kD cleavage product.

The term "status" in this context is used according to its art accepted meaning and refers to the condition or state of a gene and its products. As specifically described herein, the status of 20P1F12/TMPRSS2 can be evaluated by a number of parameters known in the art. For example, as shown in FIG. 3 and described in Example 1, the status of 20P1F12/TMPRSS2 in a biological sample can be evaluated by examining the sequences of 20P1F12/TMPRSS2 polynucleotide and/or polypeptides in that biological sample. Alternatively, as shown in FIGS. 5–7 and described in Examples 3 and 4, the status of 20P1F12/TMPRSS2 in a biological sample can be evaluated by examining the levels of 20P1F12/TMPRSS2 gene products (e.g. mRNA and/or proteins) in the that biological sample. Alternatively, as shown in FIGS. 17 and Table 1, status of 20P1F12/TMPRSS2 in a biological sample can be evaluated by observing the location of 20P1F12/TMPRSS2 in normal biological samples and comparing that to the location of 20P1F12/TMPRSS2 in a biological samples suspected of containing evidence of disregulated cell growth. Alternatively, as shown in FIGS. 18 and described in Example 10, the status of 20P1F12/TMPRSS2 in a biological sample can be evaluated by looking at the presence or absence of a specific 20P1F12/TMPRSS2 species such as the 32 kD protease fragment that results from post-translations autocatalytic cleavage. Alternatively, as shown in FIGS. 20–23 and described in Example 11, the status of 20P1F12/TMPRSS2 in a biological sample can be evaluated by looking for the presence or absence of a specific 20P1F12/TMPRSS2 immunoreactive complex in the biological sample.

Typically, skilled artisans use a number of parameters to evaluate the condition or state of a gene and its products. These include, but are not limited to the integrity and/or methylation pattern of a gene including its regulatory sequences, the location of expressed gene products (including the location of 20P1F12/TMPRSS2 expressing cells), the presence, level, and biological activity of expressed gene products (such as 20P1F12/TMPRSS2 and mRNA polynucleotides and polypeptides), the presence or absence of transcriptional and translational modifications to expressed gene products as well as associations of expressed gene products with other biological molecules such as protein binding partners (e.g. a protein-protein complex as shown for example in FIG. 21).

Alternations in the status of 20P1F12/TMPRSS2 can be evaluated by a wide variety of methodologies well known in the art, typically those discussed below. Typically an alteration in the status of 20P1F12/TMPRSS2 comprises a change in the location of 20P1F12/TMPRSS2 and/or 20P1F12/TMPRSS2 expressing cells, an increase in 20P1F12/TMPRSS2 mRNA and/or protein expression and/or the association or dissociation of 20P1F12/TMPRSS2 with a binding partner. As the data presented herein provides evidence that 20P1F12/TMPRSS2 proteins are secreted into sera upon disruption of gland architecture (see e.g. FIG. 17 and Table 1)a specific representative alteration in the status of 20P1F12/TMPRSS2 includes a change in the levels of secured 20P1F12/TMPRSS2 proteins in sera.

As discussed in detail herein, in order to identify a condition or phenomenon associated with disregulated cell growth, the status of 20P1F12/TMPRSS2 in a biological sample may be evaluated by a number of methods utilized by skilled artisans including, but not limited to genomic Southern analysis (to examine, for example perturbations in the 20P1F12/TMPRSS2 gene), northerns and/or PCR analysis of 20P1F12/TMPRSS2 mRNA (to examine, for example alterations in the polynucleotide sequences or expression levels of 20P1F12/TMPRSS2 mRNAs), and western and/or immunohistochemical analysis (to examine, for example alterations in polypeptide sequences, alternations in polypeptide localization within a sample, alterations in expression levels of 20P1F12/TMRPSS2 proteins and/or associations of 20P1F12/TMPRSS2 proteins with polypeptide binding partners). Detectable 20P1F12/TMPRSS2 polynucleotides include, for example, a 20P1F12/TMPRSS2 gene or fragments thereof, 20P1F12/TMPRSS2 mRNA, alternative splice variants 20P1F12/TMPRSS2 mRNAs, and recombinant DNA or RNA molecules containing a 20P1F12/TMPRSS2 polynucleotide.

As discussed in Examples 6, 8, 9 and 11 and shown for example, in FIGS. 20, 22, 23, 24 and 26, a number of different 20P1F12/TMPRSS2 species are observed in various biological samples. In this context, the presence, absence and/or levels of detectable 20P1F12/TMPRSS2 polypeptides can be examined to obtain information on the status of a sample. Detectable 20P1F12/TMPRSS2 polypeptides include, for example, 32 kD protease domain polypeptide, the 70 kD full length 20P1F12/TMPRSS2 protein as well the 90 kD and 103 kD species which are likely to represent complexes of a 20P1F12/TMPRSS2 polypeptide and a second biological molecule (as is seen, for example with PSA). Moreover, skilled artisans are aware that observations of similar polypeptides and/or protein complex(es) and their ratio may then be applied in the diagnosis of patients with, for example, prostate or colon cancer (see e.g. 5,672,480, 5,939,533, 5,840,501, discussed below). This is particularly relevant in the context of 20P1F12/TMPRSS2 because, as shown for example in FIG. 23, in whole tissue lystate from the prostate of a normal 28 year old male accident victim (panel C),the ratio between the 70 kD and 32 kD species of 20P1F12/TMPRSS2 appears to be different from that observed in the sera of individuals suffering from cancer (panel B).

A variety of observations which examine various 20P1F12/TMPRSS2 species and their ratios in the context of diagnostic methods are contemplated. One can examine for example: the ratio of the 32 kD species to the 70 kD species, the 90 kD species and/or the 103 kD species; the ratio of the 70 kD species to the 32 kD species, the 90 kD species and/or the 103 kD species; the ratio of the 90 kD species to the 32 kD species, the 70 kD species and/or the 103 kD species; and the ratio of the 103 kD species to the 32 kD species, the 70 kD species and/or the 90 kD species etc. Alternatively, one can examine a ratio of a subset of 20P1F12/TMPRSS2 species and, in addition, the presence of another specific 20P1F12/TMPRSS2 species. One can examine for example the ratio of the 32 kD species to the 70 kD species and the presence of the 90 kD species and/or the 103 kD species; the ratio of the 70 kD species to the 90 kD species and the presence of the 32 kD species and/or the 103 kD species; the ratio of the 103 kD species to the 32 kD species and the presence of the 70 kD species and/or the 90 kD species etc. Alternatively, one can examine a ratio of one subset of 20P1F12/TMPRSS2 species and, in addition, a ratio of another subset of 20P1F12/TMPRSS2 species. One can examine for example: the ratio of the 32 kD species to the 70 kD species and the ratio of the 32 kD species to the 90 kD species; the ratio of the 70 kD species to the 103 kD species and the ratio of the 90 kD species to the 32 kD species; the ratio of the 70 kD species to the 90 kD species and the ratio of the 103 kD species to the 32 kD species etc.

Figure 20:
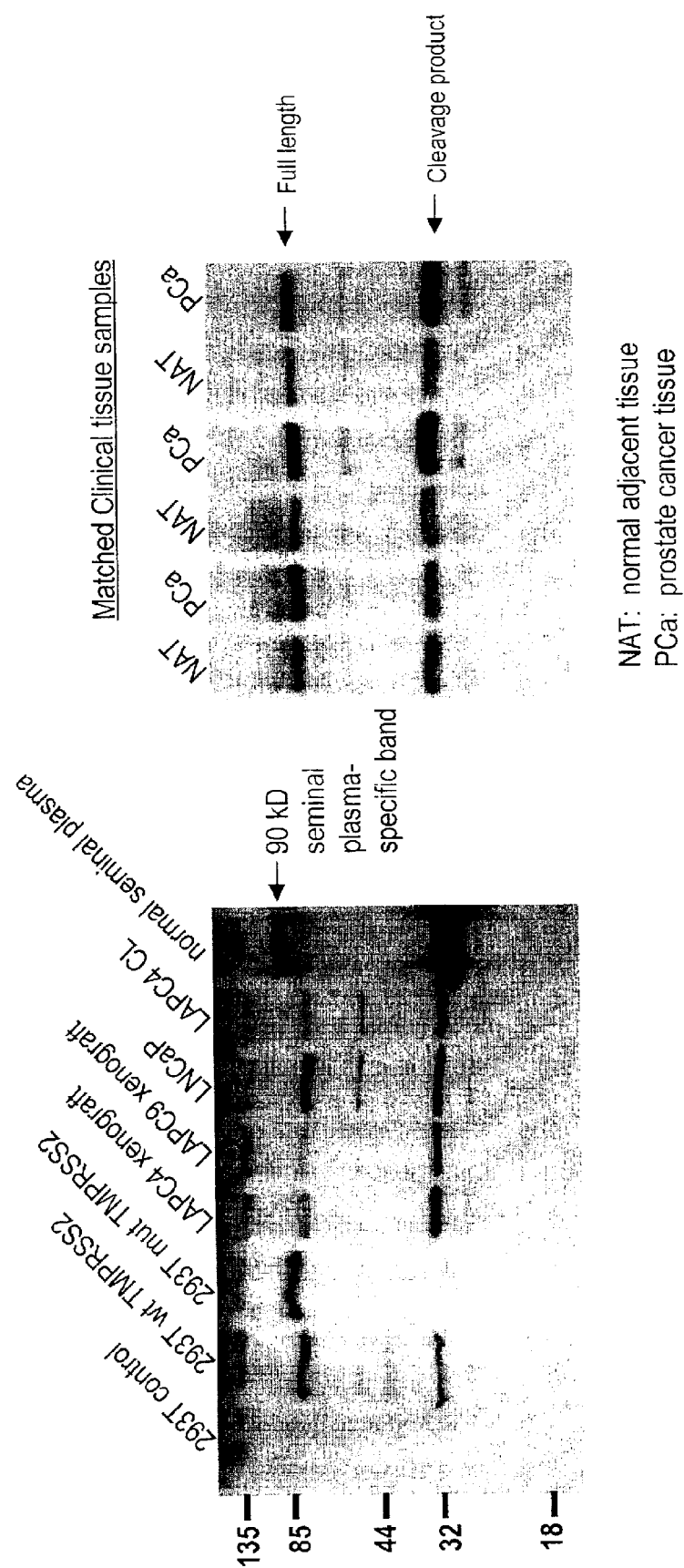
FIG. 20. 20P1F12/TMPRSS2 is expressed in prostate cancer xenografts, prostate cancer cell lines, normal seminal fluid, and clinical tissues. 20P1F12/TMPRSS2 protein expression analysis was carried out by Western blot using the anti-TMPRSS2 mAb 1F9 as indicated in FIG. 19. 293T samples were from cells transiently transfected with either an empty vector or with a retroviral expression plasmid encoding either wild-type 20P1F12/TMPRSS2 or with a protease deficient point mutant of 20P1F12/TMPRSS2. Protein lysates of LAPC4 cell line (LAPC4CL), LNCaP cells, LAPC4 and LAPC9 9 xenografts, and matched clinical tissues were obtained by solubilization of cell pellets, xenografts, and tissues in 2X SDS-PAGE sample buffer and heating. Normalization of lysate loading was verified by Ponceau S staining of nitrocellulose membranes following transfer. Seminal fluid from a normal male donor was spun for 5 minutes at 14,000 G to pellet cells and coagulated material and the supernatant was diluted 4 fold in RIPA buffer. 2 µl of this fluid was mixed in SDS-PAGE sample buffer and run in the indicated lane. Arrows indicate the 70 kD full length 20P1F12/TMPRSS2 protein, the 32 kD cleavage product, and a novel 90 kD anti-TMPRSS2 immunoreactive band in normal seminal plasma.
Figure 26:
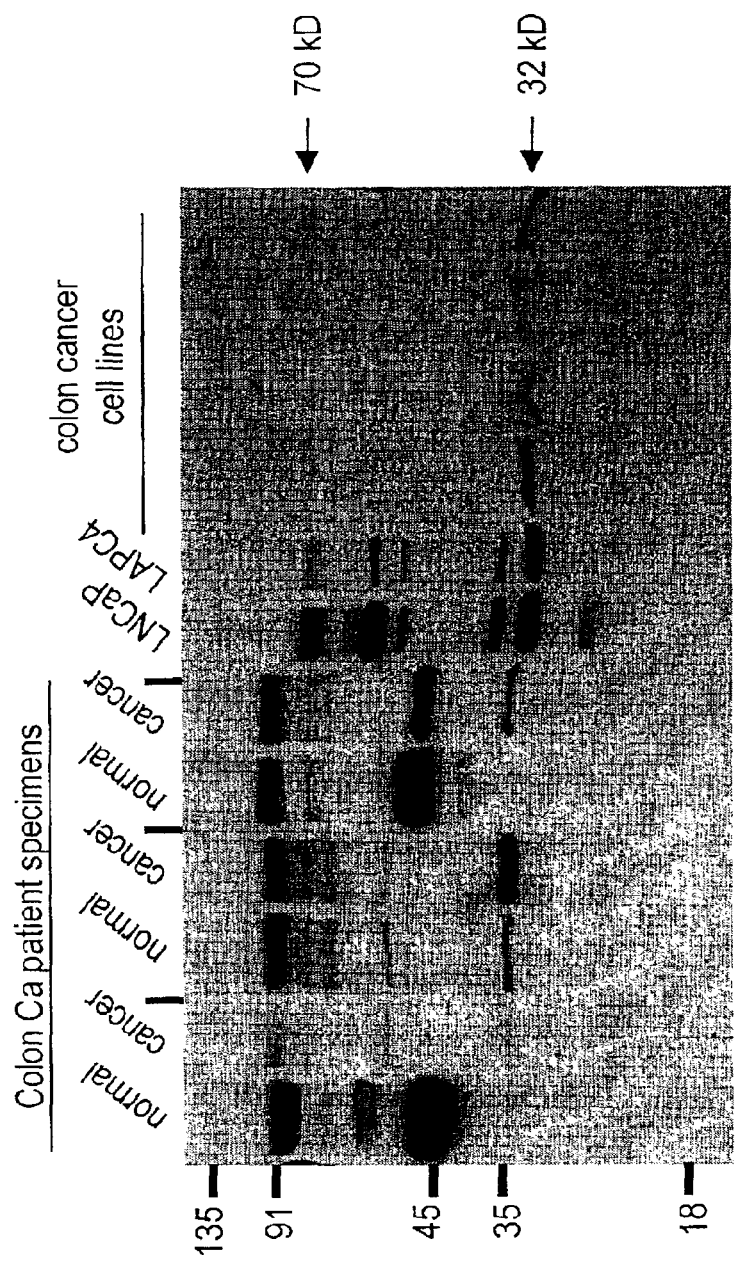
FIG. 26 High expression of the 32 kD cleavage fragment of 20P1F12/TMPRSS2 in colon cancer cell lines and colon cancer tissue samples compared to normal colon tissue. Lysates of clinical specimens representing matched colon cancer tissue or normal adjacent tissue (left side of blot) and of colon cancer cell lines (right side of blot), and of LAPC4 and LAPC9 prostate cancer xenografts were subjected to anti-TMPRSS2 Western blot analysis using 1F9 mAb. Arrows indicate the position of the 32 kD auto-catalytic fragment and the 70 kD full length 20P1F12/TMPRSS2 protein. Higher expression of the 32 kD fragment is seen in the colon cancer tissue than in the matched normal adjacent tissue. As well, the predominant immunoreactive species present in colon cancer cell lines is also the 32 kD fragment. Interestingly, there is very little expression of full length 20P1F12/TMPRSS2 protein in the colon samples but there is strong expression of an anti-TMPRSS2 immunoreactive band of ~90 kD in the colon tissues that may represent a complex of the 32 kD fragment.

When examining the various 20P1F12/TMPRSS2 species and their ratios in the context of diagnostic methods, one can also take into account additional factors such as its normal status in the specific biological tissue being examined (see e.g. tissue as shown in FIG. 17, seminal fluid as shown in FIG. 20 and serum as shown in FIG. 23). For example, various binding partners which can complex with 20P1F12/TMPRSS2 proteins may be present in varying amounts in different tissue lineages. Consequently, the relative levels of the binding partners which can complex with 20P1F12/TMPRSS2 proteins can be assayed. Lanes 5–7 of FIG. 26 illustrate the apparent different levels of such binding partners in different samples by providing evidence that certain 20P1F12/TMPRSS2 species appear to occur predominantly in colon and not in prostate derived samples (see e.g. the band at approximately 45–50 kD). In addition, this 45–50 kD band appears to be predominantly expressed in normal colon samples (see e.g. lanes 1 and 2), providing further support for methodologies which use the presence, absence or relative levels of one or more 20P1F12/TMPRSS2 species and/or 20P1F12/TMPRSS2 binding partners to provide diagnostic information on the status of a sample.

Figure 22:
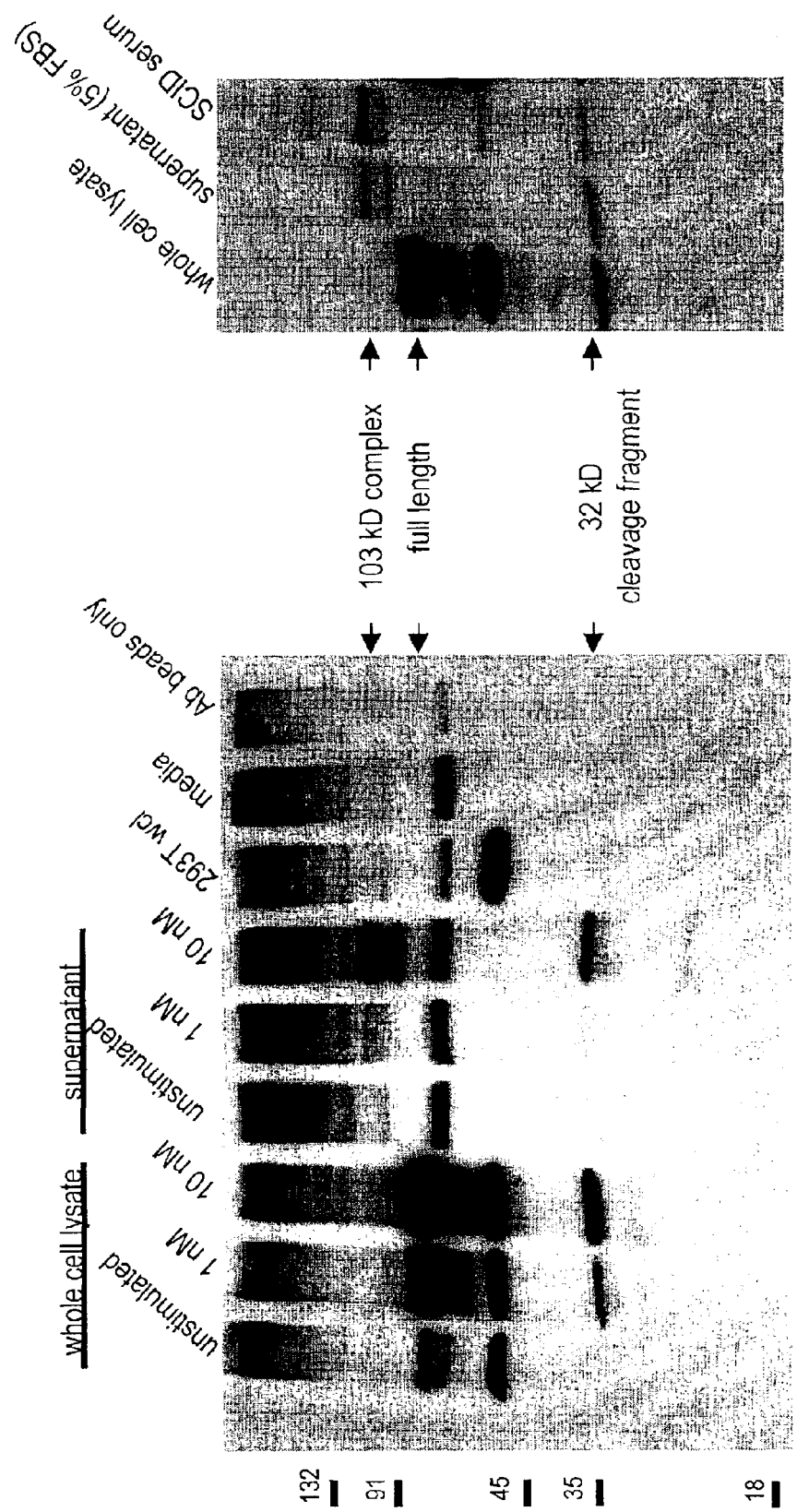
FIG. 22. Release of the proteolytic fragment of 20P1F12/TMPRSS2 protein into the supernatant of LNCaP cell cultures and into the serum of SCID mice bearing LNCaP xenografts. RIPA buffer whole cell lysates and conditioned tissue culture supernatants of LNCaP cells treated as described in FIG. 21 or grown in RPMI+5% FBS or serum from SCID mice bearing LNCaP xenografts were immunoprecipitated with anti-TMPRSS2 mAb covalently coupled to protein G beads as follows. 1 ml of RIPA whole cell lysates (600 µg of total protein), 2.5 mls of conditioned diluted with an equal volume of RIPA buffer, and 340 µl (15 mg total protein) of SCID serum diluted to 1 ml with RIPA buffer were first precleared for 3 hours at 4° C. by incubation with 50 µl of a 50% protein G bead slurry in RIPA buffer. 1F9 anti-TMPRSS2 mAb was covalently coupled to protein G beads using the homobifunctional crosslinking reagent dimethyl pimelimidate (DMP) as described in "Using Antibodies, a Laboratory Manual", Harlow and Lane, 1999, pg. 323. Then 50 µl of a 50% slurry of 1F9/protein G beads (~50 µg mAb) was added to each sample and incubated overnight at 4° C. Immunoprecipitates were washed 4 times in RIPA buffer and immune complexes were dissociated by the addition of 35 µl of 3X SDS-PAGE sample buffer and heating. 25 µl of each sample was then subjected to SDS-PAGE and Western blotting with 1F9 mAb as described in FIG. 19. RIPA buffer lysates of 293T cells (293T wcl) and 2% CD-FBS RPMI (media) were subjected to the IP/Western protocol as negative controls. Arrows indicate the full length 70 kD 20P1F12/TMPRSS2 protein, the 32 kD cleavage fragment, and the novel 103 kD anti-TMPRSS2 immunoreactive complex in androgen stimulated supernatants and SCID serum.

When examining the various 20P1F12/TMPSS2 species and their ratios in the context of diagnostic methods, one can also take into account factors such as the localization of the 20P1F12/TMPRSS2 species either within a cell (see e.g. the cell associated 20P1F12/TMPRSS2 species shown in FIG. 17) or outside of a cell (see e.g. the secreted 20P1F12/TMPRSS2 species shown in FIGS. 22 and 23). Such observations are well-known in the art and can be undertaken for example by utilizing antibodies specifically directed to domain within a secreted species (i.e. the protease domain) or antibodies specifically directed to a domain associated with the cell surface.

As discussed in detail below, 20P1F12/TMPRSS2 may be analyzed by any one of the wide variety of techniques employed for such purposes, including: (i) immunohistochemical analysis, (ii) in situ hybridization, (iii) RT-PCR analysis, (iv) western blot analysis of clinical samples and cells lines, (v) tissue array analysis, and (vi) in vivo imaging. Illustrative typical protocols for evaluating the status of a gene and its products can be found, for example in Current Protocols In Molecular Biology, Units 2 [Northern Blotting], 4 [Southern Blotting], 15 [Immunoblotting] and 18 [Proc Analysis], Frederick M. Ausubul et al. eds., 1995. Various specific immunological assays useful for the detection of 20P1F12/TMPRSS2 proteins include but are not limited to various types of radiommunoassays, enzyme-linked immunosorbent assays (ELISA), enzyme-linked immunofluoroescent assays (ELFIA), immunocytochemical methods, and the like. As an example, 20P1F12/TMPRSS2 antibodies may be labeled and used as immunological imaging reagents capable of detecting prostate and colon cancer cells (e.g., in radioscintigraphic imaging methods). For radioscintigraphic in vivo imaging, radiolabeled 20P1F12/TMPRSS2 antibodies specifically reactive with secreted epitopes of 20P1F12/TMPRSS2 are preferred.

Assays for identifying disorders associated with the disregulation of cell growth such as occurs in prostate and colon cancers can comprise detecting 20P1F12/TMPRSS2 polypeptides or polynucleotides in any one of a wide variety of biological samples used to evaluate pathological conditions, such as urine, stool, semen as well as cell preparations from tissues from the prostate, colon and other tissues which may be effected for example when a cancer metastasizes. Typical samples include peripheral blood and/or serum which can be conveniently assayed for the presence of 20P1F12/TMPRSS2 proteins or cancer cells, including but not limited to prostate and colon cancers. In this context, various 20P1F12/TMPRSS2 species are described herein in a variety of biological samples including tissue (see e.g. FIG. 17), sera (see e.g. FIG. 23) and seminal plasma (see e.g. FIG. 24).

Peripheral blood and serum may be conveniently assayed for the presence of 20P1F12/TMPRSS2 protein and/or prostate or colon cancer cells, using for example, immunological or Northern or RT-PCR analysis to detect 20P1F12/TMPRSS2. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25: 373–384, Ghossein et al., 1995, J. Clin. Oncol. 13: 1195–2000; Heston et al., 1995, Clin. Chem. 41: 1987–1688). In another approach, a recently described sensitive assay for detecting and characterizing carcinoma cells in blood may be used (Racila et al., 1998, Proc. Natl. Acad. Sci. USA 95: 4589–4594). This assay combines immunomagnetic enrichment with multiparameter flow cytomeric and immunohistochemical analyses, and is highly sensitive for the detection of cancer cells in blood, reportedly capable of detecting one epithelial cell in 1 ml of peripheral blood.

20P1F12/TMPRSS2 shares a number of characteristics with prostate specific antigen including androgen regulation, similar functional domains, a presence in serum, an ability to form a complex with one or more proteins and increased expression levels that are associated with cancer. Consequently, the various assays known in the art for evaluating PSA provide illustrations of typical methods that can also be used to evaluate 20P1F12/TMPRSS2. A number of representative assays involving the examination of PSA which contain methods which may be adapted for use with 20P1F12/TMPRSS2 are provided below. Such assays may also be used in combination with assays evaluating the status of 20P1F12/TMPRSS2.

U.S. Pat. No. 4,840,501, which is incorporated herein by reference, provides typical methods for examining immunologically determinable PSA in a blood sample. In this variation of such well known assays, PSA is examined by a two-site immunometric assays in which the blood sample is treated to render free PSA (fPSA) immunologically nondetectable. Measurement of cPSA blood levels in this context has been found to provide a method for aiding in the diagnosis and monitoring of prostate cancer that is highly sensitive and specific, and eliminates the need for a significant number of patients to undergo unnecessary prostate biopsy. A particularly preferred immunometric assay method described in U.S. Pat. No. 5,840,501 employs three anti-PSA antibodies: an antibody that binds to both cPSA and fPSA (anti-tPSA), a second anti-tPSA antibody which is characterized by the unique property that binding to fPSA is blocked by binding of fPSA-specific antibodies, and a third antibody which is a fPSA-specific antibody. Thus, binding of the fPSA-specific antibody to PSA in the sample alloys only cPSA to be measured in the immunometric assay. Following the methods described in U.S. Pat. No. 5,840,501 one skilled in the art could employ analogous methods with, for example three anti-20P1P12/TMPRSS2 antibodies: an antibody that binds to both c20P1F12/TMPRSS2 and f20P1F12/TMPRSS2 (anti-t20P1F12/TMPRSS2), a second anti-t20P1F12/TMPRSS2 antibody which is characterized by the unique property that binding to f20P1F12/TMPRSS2 is block by binding of f20P1F12/TMPRSS2 specific antibodies, and a third antibody which is a f20P1F12/TMPRSS2-specific antibody. Thus, binding of the f20P1F12/TMPRSS2-specific antibody to 20P1F12/TMPRSS2 in the same would allow only c20P1F12/TMPRSS2 to be measured in an immunometric assay.

U.S. Pat. No. 5,939,533, which is incorporated herein by reference, provides additional typical immunoassays to measure free PSA as well as a proteinase inhibitor complex. In the methods described in U.S. Pat. No. 5,939,533, free PSA and PSA complex are measured by a non-competitive immunoassay employing at least two different monoclonal antibodies. The invention is further characterized by that the PSA proteinase inhibitor complex of interest is formed either with $\alpha_1$-antichymotrypsin, $\alpha_1$-protease inhibitor (API) or $\alpha_2$-macroglobulin. Moreover, the invention described in U.S. Pat. No. 5,939,533, is characterized by the observation that free PSA, the PSA-proteinase inhibitor complex and their ratio can be applied in the diagnosis of patients with prostate cancer. Following the methods described in U.S. Pat. No. 5,939,533, one skilled in the art could employ analogous methods to observe, for example the 20P1F12/TMPRSS2 protein species as shown in FIGS. 23, 24 and 26. In this context, observations of free 20P1F12/TMPRSS2 and/or 20P1F12/TMPRSS2-protein complex(es) and their ratio may then be applied to the diagnosis of patients with, for example, prostate or colon cancer.

U.S. Pat. No. 5,672,480, which is incorporated herein by reference, provides additional typical immunoassay methods for prostate specific antigen (PSA). Also presented in the methods described in U.S. Pat. No. 5,672,480 is a complex which resembles a complex of PSA and $\alpha_1$-antichymotrypsin (ACT) that can be used as a calibrator or control in an immunoassay for PSA. Further presented in U.S. Pat. No. 5,672,480 are methods for fractionating polyclonal antibodies, to PSA, into those which bind epitopes that are masked by the binding of PSA to ACT and those which do not bind such epitopes. Following the methods described in the methods described in U.S. Pat. No. 5,672,480 one skilled in the art could employ analogous methods to generate a complex which resembles a complex of 20P1F12/TMPRSS2 and its binding partner that can be used as a calibrator or control in an immunoassay for 20P1F12/

TMPRSS2. In addition, one skilled in the art could employ the methods presented in 5,672,480 for fractionating polyclonal antibodies to 20P1F12/TMPRSS2, into those which bind epitopes that are masked by the binding of 20P1F12/TMPRSS2 to its binding partner and those which do not bind such epitopes.

U.S. Pat. No. 5,614,372 which is incorporated herein by reference describes another typical bioaffinity assay of prostate-specific antigen (PSA) comprising the measurement of either the concentration of total PSA (PSA-T), the concentration of free form of PSA (PSA-F) or the concentration of PSA complexed to alpha-1-antichymotrypsin (PSA-ACT), PSA-T being the sum of PSA-F and PSA-ACT. According to the disclosure of U.S. Pat. No. 5,614,372, additionally the concentration of another molecule, human glandular kallikrein (hGK-1) is measured. The concentrations of PSA-T and hGK-1 can be measured in one single assay or in separate assays, with the sum of the concentrations of PSA-T and hGK-1 used to determine the ratio a) PSA-F/(PSA-T+hGK-1) and/or b) PSA-ACT/(PSA-T+hGK-1). In the disclosure of U.S. Pat. No. 5,614,372 both of these ratios are shown to have clinical utility for the discrimination of prostate cancer and benign prostatic hyperplasia. Following the methods described in U.S. Pat. No. 5,614,372, one skilled in the art could employ analogous methods to analyze 20P1F12/TMPRSS2 comprising the measurement of either the concentration of total 20P1F12/TMPRSS2 (20P1F12/TMPRSS2-T), the concentration of free form of 20P1F12/TMPRSS2 (20P1F12/TMRSS2-F) or the concentration of 20P1F12/TMPRSS2 complexed to its binding partner (20P12F12/TMPRSS2-BP), 20P1F12/TMPRSS2-T being the sum of 20P1F12/TMPRSS2-F and 20P1F12/TMPRSS2-BP. Additionally the concentration of human glandular kallikrein (hGK-1) can be measured and used to determine the ratio a) 20P1F12/TMPRSS2-F/(20P1F12/TMPRSS2-T+hGK-1) and/or b) 20P1F12/TMPRSS2-ACT/(20P1F12/TMRSS2-T+hGK-1). As in the disclosure of U.S. Pat. No. 5,614,372 these ratios may be employed for clinical utility.

U.S. Pat. No. 5,939,258, which is incorporated herein by reference, provides other typical methods for diagnosing prostate micrometastasis whereby nucleic acids from a tissue sample from a patient are isolated, nucleic acids from the tissue sample specific for prostate cancer are amplified, or a signal generated by hybridization of a probe specific to a prostate cancer specific nucleic acid is amplified; and detection of amplified nucleic acids is indicative of micrometastasis of prostate cancer. As illustrated in detail below, probes specific to a 20P1F12/TMPRSS2 nucleic acid can similarly be amplified; with the detection of amplified nucleic acids providing evidence of micrometastasis of prostate or colon cancer.

U.S. Pat. No. 5,972,615, which is incorporated herein by reference, provides other typical diagnostic techniques for the detection of human prostate disease. The invention relates particularly to probes and methods for evaluating the presence of RNA species that are differentially expressed in metastatic prostate cancer compared to normal human prostate, benign prostatic hyperplasia, and non-metastatic prostate cancer. The invention also relates to probes and methods for evaluating the presence of RNA species that are differentially expressed in the peripheral blood of individuals with the disease state compared to normal healthy individuals. Described are methods of therapeutic use for genes identified as differentially expressed in metastatic prostate cancer, and means for screening pharmaceuticals effective in treatment of prostate cancer. Similarly, U.S. Pat. No. 5,972,615 provides isolated mammalian nucleic acid molecules encoding alternatively spliced prostate-specific membrane (PSM) antigen, isolated nucleic acid molecules encoding prostate-specific membrane antigen promoter sequences and methods for detecting hematogenous micrometastic tumor cells of a subject in the context of determining prostate cancer progression in a subject. As illustrated in detail below, molecules specific for 20P1F12/TMPRSS2 can be used for detecting hematogenous micrometastic tumor cells of subject in the context of determining prostate and/or colon cancer progression in a subject.

As illustrated in the various typical embodiments provided below, a wide variety of methods for determining the status of 20P1F12/TMPRSS2 in an individual may be used to provide prognostic and/or diagnostic information. Such methods for determining the status of 20P1F12/TMPRSS2 can provide information useful for predicting susceptibility to a particular disease, the stages and progression of the disease, and/or tumor aggressiveness. In this context a variety of illustrative aspects of the invention are provided below as typical methods and assays for determining the status of 20P1F12/TMPRSS2 and evaluating syndromes which involve the disregulation of cell growth.

A particularly preferred embodiment of the invention consists of a method of examining or testing a biological sample of interest for evidence of disregulated cellular growth comprising comparing the status of 20P1F12/TMPRSS2 in the test biological sample to the status of 20P1F12/TMPRSS2 in a corresponding normal sample, wherein alterations in the status of 20P1F12/TMPRSS2 in the biological sample are associated with disregulated cellular growth. As the disregulation of cell growth (i.e. the disruption of normal cellular proliferation that occurs in hyperplastic, precancerous and cancerous cells etc.) is a significant factor in the complex multistep process of carcinogenesis and tumor progression, methods for identifying a condition or phenomena that is indicative of disregulated cellular growth (i.e. an alteration in the normal biology of 20P1F12/TMPRSS2) are of particular interest to medical practitioners because the early detection of pathologies such as cancers has profound influence on morbidity and mortality.

As shown for example in FIG. 7, 20P1F12/TMPRSS2 is found to be overexpressed in prostate and colon cancer cell lines. Moreover, as discussed in detail below, 20P1F12/TMPRSS2 exhibits a constellation of characteristics which provide strong evidence that it is involved in oncogenic processes. Consequently, the identification of alterations in the status of 20P1F12/TMPRSS2 in a test sample (e.g., an increase in mRNA expression) as compared to a corresponding normal sample from, for example an unaffected proximal location (e.g. normal colon or prostate tissue) or an unaffected individual provides evidence of disregulated cellular growth.

As described in detail above, the status of 20P1F12/TMPRSS2 in a biological sample can be examined by a number of well known procedures in the art. For example, the status of 20P1F12/TMPRSS2 in a biological sample can be examined by comparing, for example, the level of 20P1F12/TMPRSS2 polynucleotide or polypeptide expression known to occur in non-cancerous samples versus precancerous or cancerous samples (with an overexpression of 20P1F12/TMPRSS2 polynucleotides or polypeptides providing evidence of disregulated cellular growth). In this context, 20P1F12/TMPRSS2 that can be evaluated includes both the 20P1F12/TMPRSS2 polynucleotide sequence shown in SEQ ID NO:1, as well as the 20P1F12/TMPRSS2 polypeptide sequence shown in SEQ ID NO:2.

A biological sample taken from a specific location in the body can also be examined by evaluating the sample for the presence or absence of 20P1F12/TMPRSS2 expressing cells (e.g. those that express 20P1F12/TMPRSS2 mRNAs or proteins). This examination can provide evidence of disregulated cellular growth for example, when 20P1F12/TMPRSS2 expressing cells are found in a biological sample from a region of the body that does not normally contain such cells (such as a lymph node, bone or liver etc.). Such alterations in the status of 20P1F12/TMPRSS2 in a biological sample are often associated with disregulated cellular growth. Specifically, one indicator of disregulated cellular growth is the metastases of cancer cells from an organ of origin (such as the prostate gland or the colon) to a different area of the body (such as a lymph node). Such evidence of disregulated cellular growth is important in the context of colon cancer for example because an understanding of the distribution of nodal metastasis in colon cancers will make it possible to recognize early recurrent nodal disease (see e.g. AJR Am J Roentgenol 1992 October 159(4):757–61). Such evidence of disregulated cellular growth is important in the context of prostate cancer for example because occult lymph node metastases can be detected in a substantial proportion of patients with prostate cancer, and such metastases are associated with known predictors of disease progression (see e.g. J Urol 1995 August 154(2 Pt 1):474–8).

In a specific embodiment of the invention, a method for detecting an alteration in the status of 20P1F12/TMPRSS2 mRNA in a biological sample of interest (typically from a patient suspected of having a pathological syndrome exhibiting a constellation of indicators, one of which is high 20P1F12/TMPRSS2 expression) comprises producing cDNA from the sample by reverse transcription using at least one primer; amplifying the cDNA so produced using a 20P1F12/TMPRSS2 polynucleotides as sense and antisense primers to amplify 20P1F12/TMPRSS2 cDNAs therein; and detecting the presence of the amplified 20P1F12/TMPRSS2 cDNA. In a typical embodiment, a method of detecting a 20P1F12/TMPRSS2 gene in a biological sample comprises first isolating genomic DNA from the sample; amplifying the isolated genomic DNA using 20P1F12/TMPRSS2 polynucleotides as sense and antisense primers to amplify the 20P1F12/TMPRSS2 gene therein; and detecting the presence of the amplified 20P1F12/TMPRSS2 gene. Any number of appropriate sense and antisense probe combinations may be designed from the nucleotide sequence provided for 20P1F12/TMPRSS2 (FIG. 1; SEQ ID NO:1) and used for this purpose. In another embodiment, a method of detecting the presence of a 20P1F12/TMPRSS2 protein in a biological sample comprises first contacting the sample with a 20P1F12/TMPRSS2 antibody, a 20P1F12/TMPRSS2-reactive fragment thereof, or a recombinant protein containing an antigen binding region of a 20P1F12/TMPRSS2 antibody; and then detecting the binding of 20P1F12/TMPRSS2 protein in the sample thereto.

Methods for identifying a cell which expresses and/or exhibits aberrant expression of 20P1F12/TMPRSS2 are also provided. In one embodiment, an assay for identifying a cell which expresses a 20P1F12/TMPRSS2 gene comprises detecting the presence of 20P1F12/TMPRSS2 mRNA in the cell. Methods for the detection of particular mRNAs in cells are well known and include, for example, hybridization assays using complementary DNA probes (such as in situ hybridization using labeled 20P1F12/TMPRSS2 riboprobes, Northern blot and related techniques) and various nucleic acid amplification assays (such as RT-PCR using complementary primers specific for 20P1F12/TMPRSS2, and other amplification type detection methods, such as for example, branched DNA, SISBA, TMA and the like). Alternatively, an assay for identifying a cell which expresses a 20P1F12/TMPRSS2 gene comprises detecting the presence of 20P1F12/TMPRSS2 protein in the cell or secreted by the cell. Various methods for the detection of proteins are well known in the art and may be employed for the detection of 20P1F12/TMPRSS2 proteins and 20P1F12/TMPRSS2 expressing cells.

A typical embodiment of the invention provides methods for monitoring or evaluating 20P1F12/TMPRSS2 gene products by determining the status of 20P1F12/TMPRSS2 gene products in a biological sample from an individual suspected of having a disease associated with disregulated cell growth (such as dysplasia, hyperplasia or cancer) and then comparing the status so determined to the status of 20P1F12/TMPRSS2 gene products in a corresponding normal biological sample, the presence of aberrant 20P1F12/TMPRSS2 gene products in the test biological sample relative to the normal biological sample providing an indication of the presence of disregulated cell growth within the individual.

A typical embodiment of the invention provides assays useful in determining the presence of cancer in an individual, comprising detecting a significant increase or decrease in 20P1F12/TMPRSS2 mRNA or protein expression in a biological sample relative to expression levels in the corresponding normal sample. The presence of 20P1F12/TMPRSS2 mRNA may, for example, be evaluated in biological samples including but not limited to blood and serum as well as tissue samples from colon, lung, prostate, pancreas, kidney, breast, cervix and ovary etc. Moreover, biological samples from tissues and sites associated with cancer metastases may also be evaluated. The presence of significant levels of 20P1F12/TMPRSS2 expression and/or alterations in 20P1F12/TMPRSS2 in any of these tissues may be useful to indicate the emergence, presence, metastases and/or severity of these cancers, since the corresponding normal tissues do not express 20P1F12/TMPRSS2 mRNA or protein or express it at lower levels.

A typical embodiment of the invention provides an assay useful in determining the presence of disregulated cell growth (such as occurs in cancer) in an individual which comprises detecting a significant increase in 20P1F12/TMPRSS2 mRNA or protein expression in a test cell or tissue sample relative to expression levels in the corresponding normal cell or tissue. The presence of 20P1F12/TMPRSS2 mRNA in a colon sample, for example, may indicate the emergence, presence and/or severity of colon cancer. In a related embodiment, the status of 20P1F12/TMPRSS2 gene products may be determined at the protein level rather than at the nucleic acid level. For example, such a method or assay would comprise determining the level of 20P1F12/TMPRSS2 protein expressed by cells in a test tissue sample and comparing the level so determined to the level of 20P1F12/TMPRSS2 expressed in a corresponding normal sample. The presence of 20P1F12/TMPRSS2 protein may be evaluated, for example, using immunohistochemical methods. 20P1F12/TMPRSS2 antibodies or binding partners capable of detecting 20P1F12/TMPRSS2 protein expression may be used in a variety of assay formats well known in the art for this purpose.

As noted above, the methods of detecting and quantifying the expression of 20P1F12/TMPRSS2 mRNA or protein described herein can use any of a variety of standard nucleic acid and protein detection and quantification technologies well known in the art. Standard methods for the detection and quantification of 20P1F12/TMPRSS2 mRNA include in situ hybridization using labeled 20P1F12/TMPRSS2 riboprobes, Northern blot and related techniques using 20P1F12/TMPRSS2 polynucleotide probes, RT-PCR analysis using primers specific for 20P1F12/TMPRSS2, and other amplification type detection methods, such as, for example, branched DNA, SISBA, TMA and the like. In a specific embodiment, semi-quantitative RT-PCR may be used to detect and quantify 20P1F12/TMPRSS2 mRNA expression as described in the Examples which follow. Any number of primers capable of amplifying 20P1F12/TMPRSS2 may be used for this purpose, including but not limited to the various primer sets specifically described herein. Standard methods for the detection and quantification of protein may be used for this purpose. In a specific embodiment, polyclonal or monoclonal antibodies specifically reactive with the 20P1F12/TMPRSS2 protein may be used in an immunohistochemical assay of biopsied tissue.

In related embodiments of the methods described above, one can evaluate the integrity 20P1F12/TMRPSS2 nucleotide and amino acid sequences in a biological sample in order to identify perturbations in the structure of these molecules such as insertions, deletions, substitutions and the like. Such embodiments are useful because perturbations in the nucleotide and amino acid sequences are observed in a large number of proteins associated with a growth disregulated phenotype (see e.g. Marrogi et al., J. Cutan. Pathol. 26(8): 369–378 (1999)). In this context, a wide variety of assays for observing perturbations in nucleotide and amino acid sequences are well known in the art. For example, the size and structure of nucleic acid or amino acid sequences of 20P1F12/TMPRSS2 gene products may be observed by the Northern, Southern, Western, PCR and DNA sequencing protocols discussed herein. In addition, other methods for observing perturbations in nucleotide and amino acid sequences such as single strand conformation polymorphism analysis are well known in the art (see e.g. U.S. Pat. Nos. 5,382,510 and 5,952,170).

In another embodiment, one can examine the methylation status of the 20P1F12/TMPRSS2 gene in a biological sample. Aberrant demethylation and/or hypermethylation of CpG islands in gene 5' regulatory regions frequently occurs in immortalized and transformed cells and can result in altered expression of various genes. For example, promoter hypermethylation of the pi=class glutathione S-transferase (a protein expressed in normal prostate but not expressed in <90% of prostate carcinomas) appears to permanently silence transcription of this gene and is the most frequently detected genomic alteration in prostate carcinomas (De Marzo et al., Am. J. Pathol. 155(6): 1985–1992 (1999)). In addition, this alteration is present in at least 70% of cases of high-grade prostatic intraepithelial neoplasia (PIN) (Brooks et al., Cancer Epidemiol. Biomarkers Prev., 1998, 7:531–536). In another example, expression of the LAGE-I tumor specific gene (which is not expressed in normal prostate but is expressed in 25–50% of prostate cancers) is induced by deoxy-azacytidine in lymphoblastoid cells, suggesting that tumoral expression is due to demethylation (Lethe et al., Int. J. Cancer 76(6): 903–908 (1998)). In this context, a variety of assays for examining methylation status of a gene are well known in the art. For example, one can utilize in Southern hybridization approaches methylation-sensitive restriction enzymes which can not cleave sequences that contain methylated CpG sites in order to assess the overall methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Units 12, Frederick M. Ausubul et al. eds., 1995.

An examination of gene amplification provides an additional method of assessing the status of 20P1F12/TMPRSS2. Gene amplification may be measured in a sample directly, for example, by conventional Southern blotting, Northern blotting to quantitate the transcription of mRNA [Thomas, Proc. Natl. Acad. Sci. USA, 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

A related aspect of the invention is directed to predicting susceptibility to developing a syndrome associated with disregulated 20P1F12/TMRPSS2 expression (such as cancer) in an individual. In one embodiment, a method for predicting susceptibility to cancer comprises detecting 20P1F12/TMPRSS2 mRNA or 20P1F12/TMPRSS2 protein in a biological sample, its presence indicating susceptibility to cancer, wherein the degree of 20P1F12/TMPRSS2 mRNA expression present is proportional to the degree of susceptibility. In a specific embodiment, the presence of 20P1F12/TMPRSS2 in serum or prostate or colon tissue is examined, with the presence of 20P1F12/TMPRSS2 in the sample providing an indication of prostate or colon cancer susceptibility (or the emergence or existence of a prostate or colon tumor). In a closely related embodiment, one can evaluate the integrity 20P1F12/TMPRSS2 nucleotide and amino acid sequences in a biological sample in order to identify perturbations in the structure of these molecules such as insertions, deletions, substitutions and the like, with the presence of one or more perturbations in 20P1F12/TMPRSS2 gene products in the sample providing an indication of cancer susceptibility (or the emergence, existence or metastasis of a tumor).

Yet another related aspect of the invention is directed to methods for gauging tumor aggressiveness. In one embodiment, a method for gauging aggressiveness of a tumor comprises determining the level of 20P1F12/TMPRSS2 mRNA or 20P1F12/TMPRSS2 protein expressed in serum, semen, urine, stool etc. or by cells in a sample of the tumor, comparing the level so determined to the level of 20P1F12/TMPRSS2 mRNA or 20P1F12/TMPRSS2 protein expressed in a corresponding normal sample taken from the same individual or a normal tissue reference sample, wherein the degree of 20P1F12/TMRSS2 mRNA or 20P1F12/TMRPSS2 protein expression in the suspect sample relative to the normal sample indicates the degree of aggressiveness. In a specific embodiment, the aggressiveness of prostate or colon tumors is evaluated by determining the extent to which 20P1F12/TMPRSS2 is expressed in a sample from an individual, with higher expression levels indicating more aggressive tumors. In a closely related embodiment, one can evaluate the integrity 20P1F12/TMPRSS2 nucleotide and amino acid sequences in a biological sample in order to identify perturbations in the structure of these molecules such as insertions, deletions, substitutions and the like, with the presence of one or more perturbations indicating more aggressive tumors.

Yet another related aspect of the invention is directed to methods for observing the progression of a malignancy in an individual over time. In one embodiment, methods for observing the progression of a malignancy in an individual over time comprises determining the level of 20P1F12/TMPRSS2 mRNA or 20P1F12/TMPRSS2 protein expressed in a biological sample, comparing the level so determined to the level of 20P1F12/TMPRSS2 mRNA or 20P1F12/TMPRSS2 protein expressed in an equivalent biological sample taken from the same individual at a different time, wherein the degree of 20P1F12/TMPRSS2 mRNA or 20P1F12/TMPRSS2 protein expression in the sample over time provides information on the progression of the cancer. In a specific embodiment, the progression of a cancer is evaluated by determining the extent to which 20P1F12/TMPRSS2 expression in the tumor cells alters over time, with higher expression levels indicating a progression of the cancer. In an alternative embodiment, the progression of a cancer is evaluated by determining the extent to which 20P1F12/TMPRSS2 expression in serum alters over time, with higher concentrations indicating a progression of the cancer. In a closely related embodiment, one can evaluated the integrity 20P1F12/TMPRSS2 nucleotide and amino acid sequences in a biological sample in order to identify perturbations in the structure of these molecules such as insertions, deletions, substitutions and the like, with the presence of one or more perturbations indicating a progression of the cancer.

The above diagnostic approaches may be combined with any one of a wide variety of prognostic and diagnostic protocols known in the art. For example, another embodiment of the invention disclosed herein is directed to methods for observing a coincidence between the expression of 20P1F12/TMRPSS2 gene and 20P1F12/TMPRSS2 gene products (or perturbations in 20P1F12/TMPRSS2 gene and 20P1F12/TMPRSS2 gene products) and a factor that is associated with malignancy as a means of diagnosing and prognosticating the status of a tissue sample. In this context, a wide variety of actors associated with malignancy may be utilized such as the expression of genes otherwise associated with malignancy (including PSA, PSCA, PSM and human glandular kallikrein expression) as well as gross cytological observations (see e.g. Bocking et al., Anal Quant Cytol. 6(2):74–88 (1984); Eptsein, Hum Pathol. 1995 February;26 (2):223–9 (1995); Thorson et al., Mod Path. 1998 June;11 (6):543–51; Baisden et al., Am J Surg Pathol. 23(8):918–24 9199)). Methods for observing a coincidence between the expression of 20P1F12/TMPRSS2 gene and 20P1F12/TMPRSS2 gene products (or perturbations in 20P1F12/TMPRSS2 gene and 20P1F12/TMPRSS2 gene products) and an additional factor that is associated with malignancy are useful, for example, because the presence of a set or constellation of specific factors that coincide provides information crucial for diagnosing and prognosticating the status of a tissue sample.

In a typical embodiment, methods for observing a coincidence between the expression of 20P1F12/TMPRSS2 gene and 20P1F12/TMPRSS2 gene products (or perturbations in 20P1F12/TMPRSS2 gene and 20P1F12/TMPRSS2 gene products) and a factor that is associated with malignancy entails detecting the overexpression of 20P1F12/TMPRSS2 mRNA or protein in a biological sample, detecting the overexpression of PSA mRNA or protein in a biological sample, and observing a coincidence of 20P1F12/TMPRSS2 mRNA or protein and PSA mRNA or protein overexpression. In a specific embodiment, the expression of 20P1F12/TMPRSS2 and PSA mRNA in serum or prostate and colon tissue is examined. In a preferred embodiment, the coincidence of 20P1F12/TMPRSS2 and PSA mRNA overexpression in the sample provides an indication of prostate or colon cancer, prostate or colon cancer susceptibility or the emergence, existence or metastases of a prostate or colon tumor.

In these methods, the status of 20P1F12/TMPRSS2 can be examined in a wide variety of biological samples, such as urine, stool, semen as well as cell preparations from tissues from the prostate, colon and other tissues which may be effected for example when a cancer metastasizes. In addition to these samples, peripheral blood and/or serum may be conveniently assayed for the presence of 20P1F12/TMPRSS2 proteins or cancer cells, including but not limited to prostate and colon cancers. The status of 20P1F12/TMPRSS2 in the biological sample is evaluated by any one of a large variety of art accepted methods such as Southern analysis, northern analysis, polymerase chain reaction analysis and immunoassay. Preferably, the biological sample is evaluated by examining the level of 20P1F12/TMPRSS2 mRNA expression or 20P1F12/TMPRSS2 protein expression. In especially preferred methods of the invention, the disregulated cellular growth is indicative of a prostate cancer. In alternative preferred methods, the disregulated cellular growth is indicative of a colon cancer. Preferably, the 20P1F12/TMRPSS2 evaluated in the biological sample is secreted from cells exhibiting disregulated growth.

An alternative embodiment of the invention consists of a method of identifying evidence of a neoplasm in an individual by examining a level of 20P1F12/TMPRSS2 gene expression in a test sample obtained from the individual and then comparing the level of 20P1F12/TMPRSS2 gene expression in the test biological sample (e.g. one suspected of containing evidence of a pathological condition) obtained from the individual to a level of 20P1F12TMPRSS2 gene expression found in a comparable normal biological sample (e.g. one not suspected of containing evidence of a pathological condition) wherein differences in the level of 20P1F12/TMPRSS2 gene products in the test biological sample relative to the normal biological sample are associated with the neoplasm. Preferably, the test biological sample is evaluated by examining the level of 20P1F12/TMPRSS2 mRNA expression or 20P1F12/TMPRSS2 protein expression. In especially preferred methods of the invention, the neoplasm is a prostate cancer. In alternative preferred methods, the neoplasm is a colon cancer.

A typical preferred embodiment of the invention consists of a method of detecting a cancer in an individual by examining 20P1F12/TMPRSS2 gene expression in a test biological sample obtained from the individual and then examining the individual for the presence of a factor associated with disregulated cellular growth where a coincidence of 20P1F12/TMPRSS2 gene expression in the test biological sample obtained from the individual and the presence of the factor associated with disregulated cellular growth is indicative of the cancer. In this context, a wide variety of factors associated with disregulated cellular growth may be utilized as this other factor such as the expression of genes otherwise associated with disregulated cellular growth (including mucin, laminin-5, PSA, PSCA and PSM expression) as well as gross cytological observations (see e.g. Pyke et al. Cancer Res. 1995 September 15;55(18) :4132–9; Bocking et al., Anal Quant Cytol. 6(2):74–88 (1984); Epstein, Hum Pathol. 1995 February; 26(2); 223–9 (1995); Thorson et al., Mod Pathol. 1998 June;11(6) :543–51; Baisden et al., Am J Surg Pathol. 23(8):918–24 91999)). In especially preferred methods of the invention, the cancer is a prostate cancer. In alternative preferred methods, the cancer is a colon cancer. In specific embodiments of this method, Southern analysis, northern analysis, polymerase chain reaction analysis or an immunoassay is used to examine the level of 20P1F12/TMPRSS2 mRNA expression or the level of 20P1F12/TMPRSS2 protein expression. Preferably, the 20P1F12/TMPRSS2 evaluated in the test biological sample is secreted from prostate or colon cancer cells.

IDENTIFYING MOLECULES THAT INTERACT WITH 20P1F12/TMPRSS2

The 20P1F12/TMPRSS2 protein sequences disclosed herein allow the skilled artisan to identify molecules that interact with them via any one of a variety of art accepted protocols. For example one can utilize one of the variety of so-called interaction trap systems (also referred to as the "two-hybrid assay"). In such systems, molecules that interact reconstitute a transcription factor and direct expression of a reporter gene, the expression of which is then assayed. Typical systems identify protein-protein interactions in vivo through reconstitution of a eukaryotic transcriptional activator and are disclosed for example in U.S. Pat. Nos. 5,955,280, 5,925,523, 5,846,722 and 6,004,746.

As discussed in Example 12, one can screen for molecules that interact with 20P1F12/TMPRSS2 protein sequences by examining a known panel of molecules which are likely to interact with 20P1F12/TMPRSS2 (based on observations with like molecules such as PSA) such as serum and semen serpins. Alternatively one can identify molecules that interact with 20P1F12/TMPRSS2 protein sequences by screening peptide libraries. In such methods, peptides that bind to selected receptor molecules such as 20P1F12/TMPRSS2 are identified by screening libraries that encode a random or controlled collection of amino acids. Peptides encoded by the libraries are expressed as fusion proteins of bacteriophage coat proteins, and bacteriophage particles are then screened against the receptors of interest. Peptides having a wide variety of uses, such as therapeutic or diagnostic reagents, may thus be identified without any prior information on the structure of the expected ligand or receptor molecule. Typical peptide libraries and screening methods that can be used to identify molecules that interact with 20P1F12/TMPRSS2 protein sequences are disclosed for example in U.S. Pat. Nos. 5,723,286 and 5,733,731.

Alternatively, cell lines expressing 20P1F12/TMPRSS2 can be used to identify protein-protein interactions mediated by 20P1F12/TMPRSS2. This possibility can be examined using immunoprecipitation techniques known in the art including those described as generating the data shown in FIG. 22 (see also Hamilton, B. J., et al., 1999, Biochem. Biophys. Res. Commun. 261:646–51). Typically 20P1F12/TMPRSS2 protein can be immunoprecipitated from 20P1F12/TMPRSS2 expressing prostate cancer cell lines using anti-20P1F12/TMPRSS2 antibodies. Alternatively, antibodies against His-tag can be used in cell line engineered to express 20P1F12/TMPRSS2 (vectors mentioned above). The immunoprecipitated complex can be examined for protein association by procedures such as western blotting, $^{35}$S-methionine labeling of proteins, protein microsequencing, silver staining and two dimensional gel electrophoresis.

Related embodiments of such screening assays include methods for identifying small molecules that interact with 20P1F12/TMPRSS2. Typical methods are discussed for example in U.S. Pat. No. 5,928,868 and include methods for forming hybrid ligands in which at least one ligand is a small molecule. In an illustrative embodiments, the hybrid ligand is introduced into cells that in turn contain a first and a second expression vector. Each expression vector includes DNA for expressing a hybrid protein that encodes a target protein linked to a coding sequence for a transcriptional module. The cells further contains a reporter gene, the expression of which is conditioned on the proximity of the first and second hybrid proteins to each other, an event that occurs only if the hybrid ligand binds to target sites on both hybrid proteins. Those cells that express the reporter gene are selected and the unknown small molecule or the unknown hybrid protein is identified.

A typical embodiment of this invention consists of a method of screening for a molecule that interacts with a 20P1F12/TMPRSS2 amino acid sequence shown in FIG. 1, comprising the steps of contacting a population of molecules with the 20P1F12/TMPRSS2 amino acid sequence, allowing the population of molecules and the 20P1F12/TMPRSS2 amino acid sequence to interact under conditions that facilitate an interaction, determining the presence of a molecule that interacts with the 20P1F12/TMRPSS2 amino acid sequence and then separating molecules that do not interact with the 20P1F12/TMPRSS2 amino acid sequence from molecules that do interact with the 20P1F12/TMRPSS2 amino acid sequence. In a specific embodiment, the method further includes purifying a molecule that interacts with the 20P1F12/TMPRSS2 amino acid sequence. In a preferred embodiment, the 20P1F12/TMPRSS2 amino acid sequence is contacted with a library of peptides.

KITS

The invention further provides kits for the diagnostic and therapeutic applications described or suggested above. Such kits may comprise a carrier means being compartmentalized to receive in close confinement one or more container means such as vials, tubes, and the like, each of the container means comprising one of the separate elements to be used in the method. For example, one of the container means may comprise a vector which encodes a 20P1F12/TMPRSS2 protein. Alternatively, one of the container means may comprise a probe which is or can be detectably labeled. Such probe may be an antibody (for example, for use in an ELISA assay) or polynucleotide specific for 20P1F12/TMPRSS2 protein or gene/mRNA, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

EXAMPLES

Example 1

Isolation of cDNA Corresponding to 20P1F12/ TMPRSS2 Gene by SSH Cloning and Expression Analysis Materials and Methods Cell lines and Human Tissues All human cancer cell lines used in this study were obtained from the ATCC. All cell lines were maintained in DMEM with 10% fetal calf serum. PrEC (primary prostate epithelial cells) were obtained from Clonetics and were grown in PrEBM media supplemented with growth factors (Clonetics).

All human prostate cancer xenografts were originally provided by Charles Sawyers (UCLA) (Klein et al., 1997; Craft et al. Cancer Res. 1999 October 1;59(19):5030–6). LAPC-4 AD and LAPC-9 AD xenographs were routinely passaged as small tissue chunks in recipient SCID males. LAPC-4 AI and LAPC-9 AI xenografts were derived as described previously (Klein et al., 1997; Craft et al. Cancer Res. 1999 October 1;59(19):5030–6) and were passaged in castrated males or in female SCID mice.

Human tissues for RNA and protein analyses were obtained from the Human Tissue Resource Center (HTRC) at the UCLA (Los Angles, Calif.) and from QualTek, Inc. (Santa Barbara, Calif.). A benign prostatic hyperplasia tissue sample was patient-derived.

RNA Isolation

Tumor tissue and cell lines were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides

The following HPLC purified oligonucleotides were used.
RSACDN (cDNA synthesis primer):
5'TTTTGTACAAGCTT$_{30}$3' (SEQ ID NO:6)
Adaptor 1:
5'CTAATACGACTCACTATAGGGCTCGAGCGGCC G0C0GGGCAGGT3'(SEQ ID NO:7) 3'GGC-CCGTCCA5' (SEQ ID NO:14)
Adaptor 2:
5'GTAATACGACTCACTATAGGGCAGCGTGGTCGC GGCCGAGGT3'(SEQ ID NO:8) 3'CGGCTCCA5' (SEQ ID NO:15)
PRC primer 1:
5'CTAATACGACTCACTATAGGGC3' (SEQ ID NO:9)
Nested Primer (NP)1:
5'TCGAGCGGCCGCCCGGGCAGGT3 (SEQ ID NO:10)
Nested primer (NP) 2:
5'AGCGTGGTCGCGGCCGAGGT3' (SEQ ID NO:11)

Suppression Subtractive Hybridization

Suppression Subtractive Hybridization (SSH) was used to identify cDNAs corresponding to genes which may be up-regulated in androgen dependent prostate cancer compared to benign prostatic hyperplasia.

Double stranded cDNAs corresponding to the LAPC-4 AD xenograft (tester) and the BPH tissue (driver) were synthesized from 2 µg of poly(A)$^+$ RNA isolated from xenograft and BPH tissue, as described above, using CLONTECH's PCR-Select cDNA Subtraction Kit and 1 ng of oligonucleotide RSACDN as primer. First- and second-strand synthesis were carried out as described in the Kit's user manual protocol (CLONTECH Protocol No. PT1117-1, Catalog No. K1804-1). The resulting cDNA was digested with Rsa I for 3 hrs. at 37° C. Digested cDNA was extracted with phenol/chloroform (1:1) and ethanol precipitated.

Driver cDNA (BPH) was generated by combining in a 4 to 1 ratio Rsa I digested BPH cDNA with digested cDNA from mouse liver, in order to ensure that minute genes were subtracted from the tester cDNA (LAPC-4 AD).

Tester cDNA (LAPC-4 AD) was generated by diluting 1 µl of Rsa I digested LAPC-4 AD cDNA (400 ng) in 5 µl of water. The diluted cDNA (2 µl, 160 ng) was then ligated to 2 µl of adaptor 1 and adaptor 2 (10 µM) in separate ligation reactions, in a total volume of 10 µl at 16° C. overnight, using 400 u of T4 DNA ligate (CLONTECH). Ligation was terminated with 1 µl of 0.2 M EDTA and heating at 72° C. for 5 min.

The first hybridization was performed by adding 1.5 µl (600 ng) of driver cDNA to each of two tubes containing 1.5 µl (20 ng) adaptor 1- and adaptor 2- ligated tester cDNA. In a final volume of 4 µl, the samples were overlayed with mineral oil, denatured in an MJ Research thermal cycler at 98° C. for 1.5 minutes, and then allowed to hybridize for 8 hrs at 68° C. The two hybridizations were then mixed together with an additional 1 µl of fresh denatured driver cDNA and were allowed to hybridize overnight at 68° C. The second hybridization was then diluted in 200 µl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH

To amplify gene fragments resulting from SSH reactions, two PCR amplifications were performed. In the primary PCR reaction 1 µl of the diluted final hybridization mix was added to 1 µl of PCR primer 1 (10 µM), 0.5 µl dNTP mix (10 µM), 2.5 µl 10× reaction buffer (CLONTECH) and 0.5 µl 50×Advantage cDNA polymerase Mix (CLONTECH) in a final volume of 25 µl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 µl from the pooled and diluted primary PCR reaction was added to the same reaction mix as used for PCR 1, except that primers NP1 and NP2 (10 µM) were used instead of PCR primer 1. PCR 2 was performed using 10–12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed E. coli were subjected to blue/white and ampicillin selection. White colonies were picked and arrayed into 96 well plates and were grown in liquid culture overnight. To identify inserts, PCR amplification were performed on 1 ml of bacterial culture using the conditions of PCR1 and NP1 and NP2 as primers PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis

First strand cDNAs were generated from 1 µg of mRNA with oligo (dT) 12–18 priming using the Gibco-BRL Superscript Preamplification system. The manufacturers protocol was used and included an incubation for 50 min at 42° C. with reverse transcriptase followed by RNAse H treatment at 37° C. for 20 min. After completing the reaction, the volume was increased to 200 µl with water prior to normalization. First strand cDNAs from 16 different normal human tissues were obtained from Clontech.

Normalization of the first strand cDNAs from multiple tissues was performed by using the primers 5'ATATCGC-CGCGCTCGTCGTCGACAA3' (SEQ ID NO:28) and 5'AGCCACACGCAGCTCATTGTAGAAGG3' (SEQ ID NO:29) to amplify β-actin. First strand cDNA (5 µl) was amplified in a total volume of 50 µl containing 0.4 µM primers, 0.2 μM each dNTPs, 1XTPC buffer (Clontech, 10 mM Tris-HCL, 1.5 mM MgCl$_2$, 50 mM KCl, pH8.3) and 1X Klentaq DNA polymerase (Clontech). Five μl of the PCR reaction was removed at 18, 20, and 22 cycles and used for agarose gel electrophoresis. PCR was performed using an MJ Research thermal cycler under the following conditions: initial denaturation was at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the bland intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization were required to achieve equal band intensities in all tissues after 22 cycles of PCR.

To determine expression levels of the 20P1P12 gene, 5 μl of normalized first strand cDNA was analyzed by PCR using 25, 30, and 35 cycles of amplification using the following primer pairs, which were designed with the assistance of (MIT; for details, see, www.genome.wi.mit.edu):
5'AGT CTT CCT GCT GAG TCC TTT CC 3' (SEQ ID NO:12)
5'CAA GGG CAC TGT CTA TAT TCT CAC C3' (SEQ ID NO:13)
Semi quantitative expression analysis was achieved by comparing the PCR products at cycle numbers that give light band intensities.

RESULTS

Several SSH experiments were conducted as described in the Materials and Methods, supra, and led to the isolation of numerous candidate gene fragment clones. All candidate clones were sequenced and subjected to homology analysis against all sequences in the major public gene and EST databases in order to provide information on the identity of the corresponding gene and to help guide the decision to analyze a particular gene for differential expression.

One of the cDNA clones, designated 20P1F12, showed identity to a recently described serine protease TMPSS2 (Paoloni-Giacobino et al., 1997, Genomics 44: 309–320). The isolated 20P1F12 cDNA fragment is 388 bp in length and has the nucleotide sequence shown in FIG. 4. Differential expression analysis by RT-PCR showed that the 20P1F12 gene is expressed at approximately equal levels in normal prostate and the LAPC-4 and LAPC-9 xenografts (FIG. 5, panel A). Further RT-PCR expression analysis of first strand cDNAs from 16 normal tissues showed greatest levels of 20P1F12 expression in prostate. Substantially lower level expression was observed in several other normal tissues (i.e., colon, pancreas, kidney, liver and lung) (FIG. 5, panels B and C).

Example 2

Northern Blot Analysis of 20P1F12/TMPRSS2 Gene Expression

Northern blot analysis on a panel of 16 normal human tissues using a labeled 20P1F12/TMPRSS2 probe (corresponding to the 20P1F12 SSH cDNA of FIG. 4) were conducted to confirm the prostate specificity of 20P1F12/TMPRSS2 expression initially established by RT-PCR expression analysis. The results, shown in FIG. 6 confirm and extended the RT-PCR analyses and show that 20P1F12/TMPRSS2 expression is relatively prostate specific, as expression in prostate is greater than expression in lung, kidney, pancreas or colon. No detectable expression was observed in any of the other 11 normal tissues used in this panel.

In addition, 20P1F12/TMPRSS2 expression levels in the LAPC-4 and LAPC-9 xenografts were also examined by Northern blot analysis. Northern blotting was performed on 10 μg of total RNA prepared from cell lines and LAPC xenografts using random hexamer-labeled (Boehringer Mannheim) 20P1F12/TMPRSS2 cDNA. The results, shown in FIGS. 6 and 7, indicate similar expression levels in the xenografts and normal tissue, with lower level expression seen in the LAPC-9 AI xenograft only. Further Northern blot analysis of 20P1F12/TMPRSS2 expression in a large panel of cancer cells is described in Example 4, below.

Example 3

Cloning of Full Length 20P1F12 cDNA

A full length cDNA encoding the 20P1F12/TMPRSS2 gene was isolated from a human prostate library and designated 20P1F12-GTC1. The nucleotide and amino acid sequences of 20P1F12-GTC1 are shown in FIG. 1. Plasmid p20P1F12-GTC1 (carrying the 20P1F12-GTC1 cDNA) was deposited with the ATCC (Manassas, Va.) on Feb. 12, 1999 and has been accorded ATCC Designation Number 207097. The approximately 3.5 kb 20P1F12-GTC1 cDNA encodes a protein of 492 amino acids which is almost, but not completely, identical to the sequence previously described (FIG. 2). There are several differences in the nucleotide sequence of the 20P1F12-GTC1 cDNA relative to the published TMPRSS2 sequence, six of which result in different encoded amino acids, as shown in the amino acid alignment of FIG. 3. Specifically, four of the amino acid differences are in the protease domain, three of which are non-conservative amino acid differences which could affect protease function and/or specificity. A close examination of the sequence shows 8 differences in the nucleotide sequence that result in 6 amino acid differences at positions 160, 242, 329, 449, 489 and 491 compared to the previously published sequence. All six differences were confirmed by sequencing additional 20P1F12/TMPRSS2 cDNA clones and gene fragments derived from normal prostate, LAPC-4 and LAPC-9 cDNA libraries. All of these differences occur in the membrane associated domain, two of which (amino acids 160 and 242) reside in the scavenger receptor cysteine rich (SRCR) domain, while the others are all located within the protease domain. It is unclear how these amino acid sequence differences might affect biological activity. However, it is possible that 20P1F12/TMPRSS2 and TMPRSS2 are differentially expressed in view of applicants' data showing divergent mRNA expression pattern in normal human tissue.

Example 4

20P1F12/TMPRSS2 Expression in Prostate and Colon Cancer

To analyze 20P1F12/TMPRSS2 expression in cancer tissues and cell lines, Northern blotting was performed on RNA derived from the LAPC xenografts and a panel of prostate and non-prostate cancer cell lines. The results show high levels of 20P1F12/TMPRSS2 expression in all the LAPC xenografts and in colon cancer cell lines (FIG. 7). Similar expression levels were detected in prostate, LAPC-4 AD, LAPC-4 AI, LAPC-9 AD and LNCaP. Lower levels of 20P1F12/TMPRSS2 were seen in LAPC-9 AI and AI PC-3 cells with no expression seen in DU145. High levels of 20P1F12/TMPRSS2 expression were also detected in three out of four colon cancer cell lines, including LoVo, T84 and Colo-205.

As noted above, the first report on 20P1F12/TMPRSS2 (Paoloni-Giacobino et al., 1997, Genomics 44: 309–320) identified a cDNA encoding a protein which is highly related to, but structurally distinct from the 20P1F12/TMPRSS2 disclosed herein. Moreover, the TMPRSS2 gene disclosed by Paoloni-Giacobino et al. also showed a very different expression pattern relative to the expression profile of 20P1F12/TMPRSS2. Recently, however, a second report has been published which confirms this data relating to both the 20P1F12/TMPRSS2 sequence and pattern of expression in various tissues (Lin et al., 1999 Cancer Res. Sep 1;59 (17):4180-4).

Example 5

Characterization of 20P1F12/TMPRSS2 Protein
Generation of 20P1F12/TMPRSS2 Monoclonal Antibodies TMPRSS2 represents a potential therapeutic target for prostate and colon cancers. As a cell surface associated antigen as well as a secreted protease fragment, it may be a particularly good target for antibody therapy. To explore this possibility and to further characterize the 20P1F12/TMPRSS2 protein, monoclonal antibodies directed against a GST-20P1F12/TMPRSS2 fusion protein were generated. Specifically, mouse MAbs were generated towards a carboxyl-terminal region of the protease (residues 362–440) fused to bacterial glutathione-S-transferase (GST). The GST-fusion protein was generated by PCR using the following primers to amplify the 20P1F12/TMPRSS2 sequence: 5'-TTGAATTCCAAACCAGTGTGTCTGCCC-3' (SEQ ID NO:16), 5'-AAGCTCGAGTCGTCACCCTGGCAAGAAT-3' (SEQ ID NO:17). The PCR product was inserted into pGEX-4T-3 using the EcoRI and XhoI cloning sites. GST-fusion protein was purified and used to immunize mice. The immunogen comprised an approximately 8 kD region within the protease domain, specifically amino acid residues 362 through 440 (see FIG. 1).

Mice were immunized with purified GST-TMPRSS2 and hybridomas were generated. Hybridoma supernatants were screened for specific antibodies by western blotting using lysates from 293T cells transfected with 20P1F12/TMPRSS2. 1,205 wells screened by Western Blot using pools of 3–5 wells and multi-lane. Western apparatus (every well was positive to GST-fusion protein and cleavage product by ELISA). Subclones derived by limiting dilution cloning and screening by Western blot. Seven hybridomas were identified that specifically recognize 20P1F12/TMPRSS2 by Western blotting and were designated 1F9 (IgG1, K), 2D10 (IgG1, K), 2F8 (IgG1, K), 6B11 (IgG1, K), 3G3 (IgG1, K), 8C6 (IgG1, K) and 9G8 (IgG2a, K). One clone, 1F9, was subsequently used for all studies. Western blotting of tissue, xenograft and cancer cell line lysates were performed on 20 μg of cell lysate protein. Normalization of extracts was achieved by probing cell extracts with anti-GRB-2 antibodies (Transduction Laboratories) or by visualization of total protein amounts of lanes by Ponceau S staining of membranes.

Epitope Mapping of anti-TMPRSS2 mAbs

For epitope mapping studies, anti-TMPRSS2 mAbs 1F9, 2F8, and 8C6, were biotinylated to approximately 4–7 molecules of biotin per molecule of antibody using the "EZ-link" Sulfo-NHS-LC-Biotinylation kit (Pierce, Rockford, Ill.) according to the manufacturer's protocol. These biotinylated antibodies were used in a competition ELISA in the presence and absence of a 50 fold excess of each of the other 7 unlabelled anti-TMPRSS2 antibodies (1F9, 2D10, 2F8, 3G3, 6B11, 8C6, and 9G8) using GST-TMPRSS2 protease domain (AA 255–492) as target antigen. ELISA plates were coated with 100 ng/well of GST-TMPRSS2 protease domain and blocked with PBS containing 3% milk. Plates were then incubated with or without excess unlabelled mAb (12.5 ug/ml) for 1 hour at room temperature (RT). Plates were washed and then incubated with 250 ng/ml of either biotinylated 2F8 or 8C6mAbs, or 100 ng/ml of 1F9 mAb for 1.5 hour at RT. Plates were washed and then incubated with a 1:2000 dilution of avidin HRP conjugate (Neutralite, Fisher Scientific) for 1 hour. Plates were washed, developed with TMB substrate, neutralized with 1 M H2SO4, and ODs of wells were obtained at 450 nm.

Table 2 below provides the results of these epitope mapping studies. Data in Table 2 are the means±range of duplicate determinations. 1F9-B, 2F8-B, 8C6-B: biotinylated forms of mAbs. In Table 2, unlabelled mAbs that compete for binding of biotinylated Abs are indicated in bold.

The antibodies described above are useful for analyzing and characterizing 20P1F12/TMPRSS2 polypeptides. Two major protein bands of approximately 54 (the predicted molecular weight (MW) of 20P1F12/TMPRSS2) and approximately 32 kilodaltons are identified in in vitro translation assays using the 20P1F12/TMPRSS2 cDNA and 1F9. Western blotting of LNCaP, LAPC-4 and LAPC-9 cell lysates identifies two major protein bands of approximately 70 and 32 kilodaltons (kD) (FIG. 8b). Molecular weights of Western blot protein bands were determined using the molecular weight calculating function of AlphaEase image analysis software (Alpha Innotech Corporation, San Leandro, Calif.) with pre-stained molecular weight markers (BioRad) as calibrators. As the predicted molecular weight (MW) of 20P1F12/TMPRSS2 is 54 kD, this data suggests that the 70 kD isoform is modified, possibly by glycosylation. The 32 kD form is a proteolytically cleaved fragment containing the carboxyl-terminal epitopes recognized by the antibodies.

Additional 20P1F12/TMPRSS2 mAbs may be generated by cell-based immunization using LAPC-9 cells expressing 20P1F12/TMPRSS2 as a screening agent for cell-based ELISAs. In addition, 20P1F12/TMPRSS2 mAbs may be generated using a purified 20P1F12/TMPRSS2 protein such as the secreted protease domain fragment as an immunogen. For example, recombinant 20P1F12/TMPRSS2 having an amino-terminal His-tag may be expressed in a baculovirus system using pBlue-Bac4.5 (Invitrogen). His-tagged 20P1F12/TMRSS2 may then be purified using a Nickel column, quantified and used as immunogen. Alternatively, 20P1F12/TMPRSS2 protease domain may be purified from a biological sample (e.g. seminal plasma) using immunoaffinity chromatography with am anti-20P1F12/TMPRSS2 antibody such as the 1F9 antibody described herein. Screening of monoclonal may be performed using cell-based ELISAs with, for example, LNCaP and PC-3-/TMPRSS2 cells.

Tissue Staining

Immunohistochemical analysis of formalin fixed, paraffin-embedded tissues with 1F9 MAb was performed on 4 micron tissue sections. After steam treatment in sodium citrate (10 mM, pH 6.0), slides were incubated with 10 μg/ml 1F9 MAb followed by an incubation with biotinylated rabbit-anti-mouse IgG. Competitive inhibition studies were carried out in the presence of 50 µg/ml of GST or GST-20P1F12/TMPRSS2 fusion protein. The reactions were visualized using avidin conjugated horseradish-peroxidase (Vector Labs, Burlingame, Calif.).

Cellular Localization

To study the characteristics of the 20P1F12/TMPRSS2 protein, 20P1F12 cDNA (FIG. 1) was cloned into pcDNA 3.1 Myc-His (Invitrogen), which provides a 6-His tag at the carboxyl-terminus. The construct was transfected into 293T cells and was analyzed by cell-surface biotinylation. Biotinylated cell surface proteins were affinity purified using streptavidin-sepharose. Western blot analysis of streptavidin affinity purified proteins using an anti-His antibody demonstrated the presence of 20P1F12/TMPRSS2 proteins in various biological samples (see e.g. FIG. 9a and FIG. 23). Therefore, 20P1F12/TMPRSS2 can be found both at the cell surface as well as being secreted form cells.

To examine surface localized endogenous 20P1F12/TMPRSS2 in LNCaP and PC-3 prostate cancer cells, biotinylated cell surface proteins were affinity purified with streptavidin-sepharose and probed with anti-20P1F12/TMPRSS2 antibodies. Western blotting of streptavidin purified proteins suggest cell surface biotinylation of endogenous 20P1F12/TMPRSS2 in both LNCaP and PC-3 cells appearing as 32 and 70 kD protein bands (FIG. 9b). In additional controls, 20P1F12/TMPRSS2 protein was not detected in streptavidin precipitates from non-biotinylated cells (FIG. 8b).

Interestingly, 293T cells transfected with a carboxyl-terminal His-tagged 20P1F12/TMPRSS2 express primarily the 70 kD protein (FIG. 9a). As the 20P1F12/TMPRSS2 protease domain is located at the carboxyl-terminus, the 32 kD fragment is a result of auto-catalytic cleavage (see Example 10 below), is likely inhibited by the His tag. The related molecule, hepsin (TMPRSS1), appears to be capable of autoactivation in a concentration dependent manner (Vu et al., 1997, J. Biol. Chem. 272: 31315–31320). This auto-catalytic cleavage may be exploited to identify small molecules that inhibit 20P1F12/TMPRSS2 activity. Cells may be grown in the presence or absence of small molecule inhibitors to specifically look for inhibition of cleavage. As discussed above, such small molecules may be tested as prostate cancer therapeutics.

Glycosylation of 20P1F12/TMPRSS2

Figure 10:
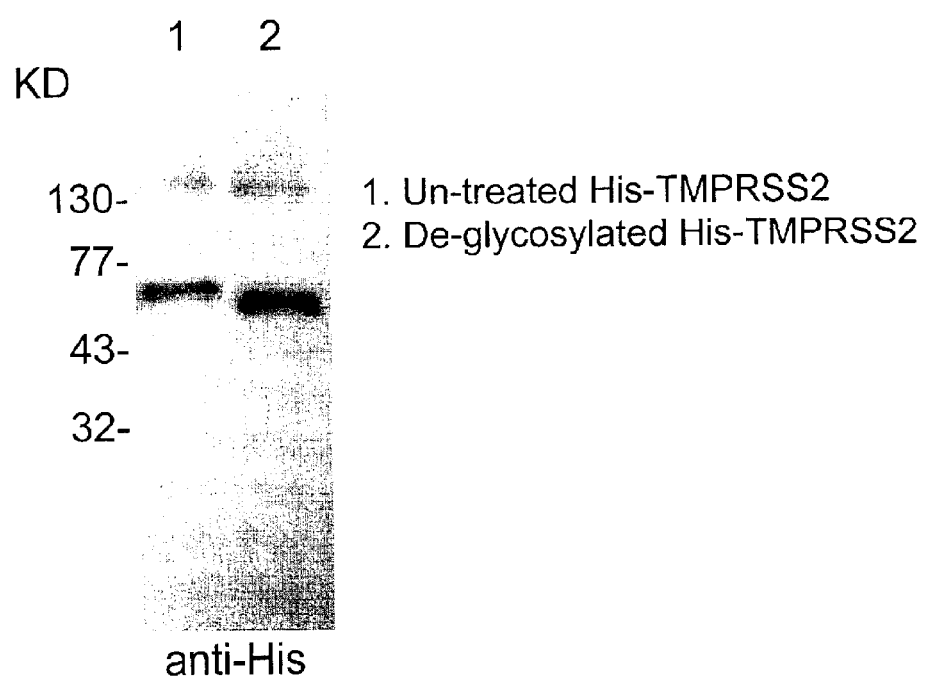
FIG. 10. De-glycosylation of 20P1F12/TMPRSS2 in transfected 293T cells. His-tagged 20P1F12/TMPRSS2 transfected into 293T cells was purified using Nickel-agarose. 20P1F12/TMPRSS2 protein was then de-glycosylated using N-glycosidase F. Untreated 20P1F12/TMPRSS2 (lane 1) and de-glycosylated protein (lane 2) were analyzed by western blotting using anti-His antibodies. A shift in molecular weight is detected with de-glycosylation. Molecular weight standards are indicated on the side in kilodaltons (KD).

The predicted MW of 20P1F12/TMPRSS2 is significantly smaller than the apparent MW detected by Western blotting. This suggests that 20P1F12/TMPRSS2 may be glycosylated. The GTC1 sequence indicates that there are three potential glycosylation sites with the consensus sequence of NXS/T (residues 128, 213, 249). To explore the possibility that 20P1F12/TMPRSS2 is glycosylated, His-tagged 20P1F12/TMPRSS2 was transfected into 293T cells and purified using a Nickel-agarose (Invitrogen). Affinity purified protein was eluted with 50 mM EDTA, pH 8.0, and was de-glycosylated using N-glycosidase F (Boehringer Mannheim) according to the manufacturers protocol. Untreated and de-glycosylated protein were analyzed by western blotting using anti-His antibodies. The results show a 5–8 kD MW shift of 20P1F12/TMPRSS2 with N-glycosidase F treatment (FIG. 10), indicating that 20P1F12/TMPRSS2 is indeed a glycosylated protein. De-glycosylated 20P1F12/TMPRSS2 still exhibited a MW of at least 5–10 kD larger than the predicted size, indicating that either the de-glycosylation reaction was not complete (or that glycosylation is O-linked), or that 20P1F12/TMPRSS2 may exhibit additional post-translational modifications (such as phosphorylation, sulfation).

Androgen Regulation

Figure 11:
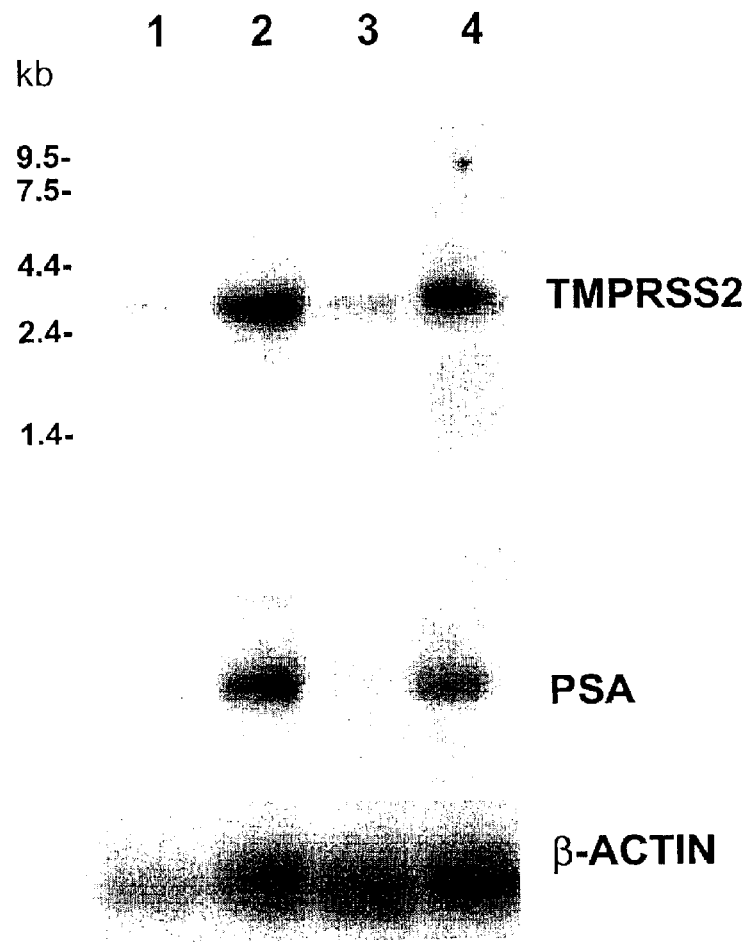
FIG. 11. Androgen regulation of 20P1F12/TMPRSS2 cell surface protease. LNCaP cells were deprived of androgen by growing cells in 2% charcoal-stripped fetal bovine serum for 1 week (lane 1), or 24 hours (lane 3). Androgen regulation was determined by stimulating 24 hour starved cells with 10 nM mibolerone (androgen analogue) for 9 hours (lane 4). Expression of 20P1F12/TMPRSS2 was compared to 20P1F12/TMPRSS2 levels in LNCaP cells growing in complete medium (lane 2) by northern blotting of 10 μg of RNA/lane probed with a 20P1F12/TMPRSS2 probe. Equal RNA loading was determined by ethidium bromide staining and subsequent probing with a β-acting probe. PSA levels were determined as a control for androgen regulation. Molecular weight standards are indicated on the side in kilobases (kb).

Northern blotting shows that expression of 20P1F12/TMPRSS2 seems to decrease in the androgen independent LAPC-9 xenograft and the androgen independent cell lines PC-3 and DU145 (FIG. 6), suggesting that 20P1F12/TMPRSS2 may be an androgen regulated gene. To explore this possibility, LNCaP cells, which are androgen dependent and express significant levels of 20P1F12/TMPRSS2, were deprived of androgen for one week by growing them in media containing 2% charcoal-stripped fetal bovine serum (FBS). The cells were then stimulated with mibolerone, a synthetic androgen analogue, at various time points. Cells were harvested for RNA and Northern blotting. As a loading control, the same blot was also probed with β-actin. The results (FIG. 11) show a clear reduction of 20P1F12/TMPRSS2 expression during androgen deprivation (FIG. 11). Addition of mibolerone increased 20P1F12/TMPRSS2 expression significantly, indicating that it is an androgen responsive gene. Expression of prostate-specific antigen (PSA) in the same samples was monitored as a positive control for androgen regulation (FIG. 11).

To determine the optimal time of 20P1F12/TMPRSS2 induction, androgen starved cells were stimulated with mibolerone for various time points. Cells were harvested for RNA and protein isolation to perform northern and western blotting respectively. The results (FIG. 12) show induction of 20P1F12/TMPRSS2 message within three hours of stimulation and increased through 24 hours after hormone addition. In addition, 20P1F12/TMPRSS2 expression appears to go down slightly in the LAPC-4 xenografts.

To analyze the protein levels, western blotting of cell lysates using the 1F9 mAb was performed. Additional controls for 20P1F12/TMPRSS2 expression included PC-3 cells infected with a retrovirus encoding either neo or 20P1F12/TMPRSS2. Infected PC-3 cells were selected in G418 for 2–3 weeks and harvested for western blotting. The results showed expression of 20P1F12/TMPRSS2 in the cells infected with a 20P1F12/TMPRSS2 virus, and no detectable 20P1F12/TMPRSS2 expression in the neo cells.

Figure 12:
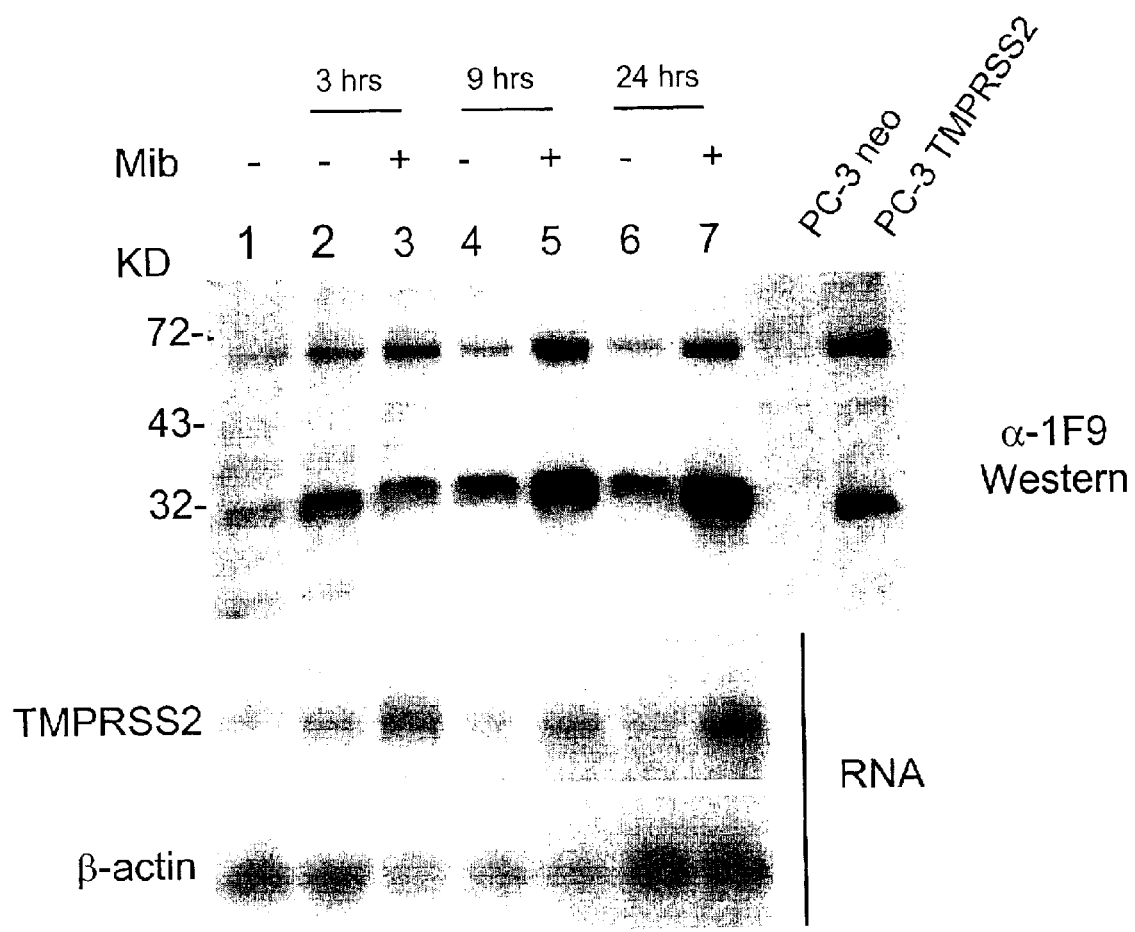
FIG. 12. Androgen regulation of 20P1F12/TMPRSS2 in LNCaP. LNCaP cell were deprived of androgen by growing cells in 2% charcoal-stripped fetal bovine serum for 1 week. Androgen regulation was determined by stimulating cells with mibolerone (Mib) for various time points. Expression of 20P1F12/TMPRSS2 was determined by western blotting of cell lysates using anti-1F9 mAb. As additional controls cell lysates from PC-3 cells infected with either neo (as a control) or 20P1F12/TMPRSS2 were used. Equal protein loading was determined by probing the western blot with anti-Grb-2 antibodies (Transduction Laboratories). Protein expression of 20P1F12/TMPRSS2 was compared to RNA levels by northern blotting of 10 μg RNA/lane probed with a 20P1F12/TMPRSS2 probe. Equal RNA loading was determined by probing the northern blot with a β-acting probe.

When looking at androgen deprived LNCaP cells, 20P1F12/TMPRSS2 expression is still detectable, but visibly reduced when compared to androgen stimulated cells. However, the first time point of induced expression appears for 9 hours of stimulation, indicating that protein expression of 20P1F12/TMPRSS2 lags behind RNA induction (FIG. 12). Moreover, FIG. 21 shows the androgen induction and release of the 32 kD auto-proteolytic fragments into the supernatants LAPC4 and LNCaP cells and appearance of a novel 103 kD anti-TMPRSS2 immunoreactive protein complex.

These results demonstrate that 20P1F12/TMPRSS2 is an androgen regulated gene, similar to other prostate specific proteases, such as PSA and hK2 (Young et al., 1995, J. Androl. 16:97).

Effect of 20P1F12/TMPRSS2 on NIH 3T3 Morphology

20P1F12/TMPRSS2 exhibits prostate specific expression and seems to be regulated by androgen. To determine the effect of expressing 20P1F12/TMPRSS2 in a heterologous non-prostate cancer cell line, 20P1F12/TMPRSS2 retrovirus was used to infect NIH 3T3 cells. The morphology of cells infected with 20P1F12/TMPRSS2 retrovirus was compared to the morphology of control (neo) virus infected cells. A population of infected cells exhibited a distinct vacuolar appearance compared to control cells (FIG. 13), which seem to correlate with high levels of expression. Upon passaging this infected cell population, vacuole-bearing cells gradually disappeared with apparently reduced expression of 20P1F12/TMPRSS2.

Evaluation of 20P1F12/TMPRSS2 Function

20P1F12/TMPRSS2 function was assessed in mammalian cells engineered to express 20P1F12/TMPRSS2. For this purpose, 20P1F12/TMPRSS2 was cloned into several vectors, including pcDNA 3.1 myc-His-tag (Invitrogen), the retroviral vector pSRαtkneo (Muller et al., 1991, MCB 11:1785), and pIND (Invitrogen) an ecdysone-inducible expression system. Using these expression vectors, 20P1F12/TMPRSS2 was expressed in several cell lines, including PC-3. Expression of 20P1F12/TMPRSS2 was monitored using anti-20P1F12TMPRSS2 antibodies by Western and FACS analysis. Purified 20P1F12/TMPRSS2 is used to identify the substrate.

Such mammalian cell lines expressing 20P1F12/TMPRSS2 can then tested in several in vitro, including cell proliferation, cell adhesion, cell invasion using a membrane invasion culture system (MICS) (Welch et al., Int. J. Cancer 43: 449–457) in tissue culture, and in vivo assays, including tumor formation in SCID mice. The 20P1F12/TMPRSS2 cell phenotype is compared to the phenotype of cells which do not express 20P1F12/TMPRSS2.

To assess the functional role of the different domains in 20P1F12/TMPRSS2, the following deletion mutants and point mutants are generated: (i) ΔSRCR (93 a.a. deletion); (ii) ΔLDLRA (35 a.a. deletion); and (iii) mutant of the catalytic triad: H296Q, D345N, S441A (single point mutants). 20P1F12/TMPRSS2 mutants were cloned into the retroviral vectors psRαtkneo for expression in mammalian cells. The resulting mutants are useful for elucidating the importance of the different domains and residues See e.g. Example 10 below). In addition, these mutants are useful for determining whether such mutants function as dominant negative molecules. Dominant negative activity may be manifested in cells that express endogenous 20P1F12/TMPRSS2, such as LNCaP. Dominant negative activity may be due to interactions with substrates via protease domain, or via the protein-protein interaction domains. The mutant 20P1F12/TMPRSS2 molecules are tested in the same in vitro and in vivo assays as wild-type 20P1F12/TMPRSS2 (see above). Such dominant negative 20P1F12/TMPRSS2 molecules may be useful therapeutically. For example, a dominant negative 20P1F12/TMPRSS2 may introduced into prostate cancer cells via gene therapy vectors capable of delivering and expressing the corresponding coding sequence into prostate tumor cells. Similarly, such methods may be useful in the treatment of colon cancer.

Determining the characteristics of 20P1F12/TMPRSS2 expression in normal mouse tissues and in transgenic mice provided further information about the function of 20P1F12/TMPRSS2. Northern blot analysis using probes designed from the 20P1F12/TMPRSS2 sequences provided herein may be used to define the expression pattern of murine 20P1F12/TMPRSS2. In addition, 20P1F12/TMPRSS2 expression during development in the mouse embryo can be analyzed. The resulting data will identify a tissue source for cloning the mouse gene and predict which tissues would be affected in a transgenic mouse knock-out study.

Transgenic mice may be generated and used to define the biological role of 20P1F12/TMPRSS2 in an in-vivo setting. In one approach, the human or mouse 20P1F12/TMPRSS2 genes are used to generate transgenic mice. Over-expression of spontaneous tumor formation in mice may be studies using transgenic mice. In another approach, 20P1F12/TMPRSS2 gene knock-outs are generated in mice. Such mice may also be crossed with other prostate cancer mouse models, such as the TRAMP model (Greenberg et al., 1995, PNAS 92:3439) to study the influence on prostate cancer aggressiveness and metastasis and to observe changes in disease progression.

Experiments testing 20P1F12/TMPRSS2 functional interaction with serine protease inhibitors will also provide information on 20P1F12/TMPRSS2 function. For this purpose, inhibition is accomplished using small molecule inhibitors or biological inhibitors.

Example 6

20P1F12/TMPRSS2 Protein is Proteolytically Cleaved in Tissues and Cell Lines

Figure 15:
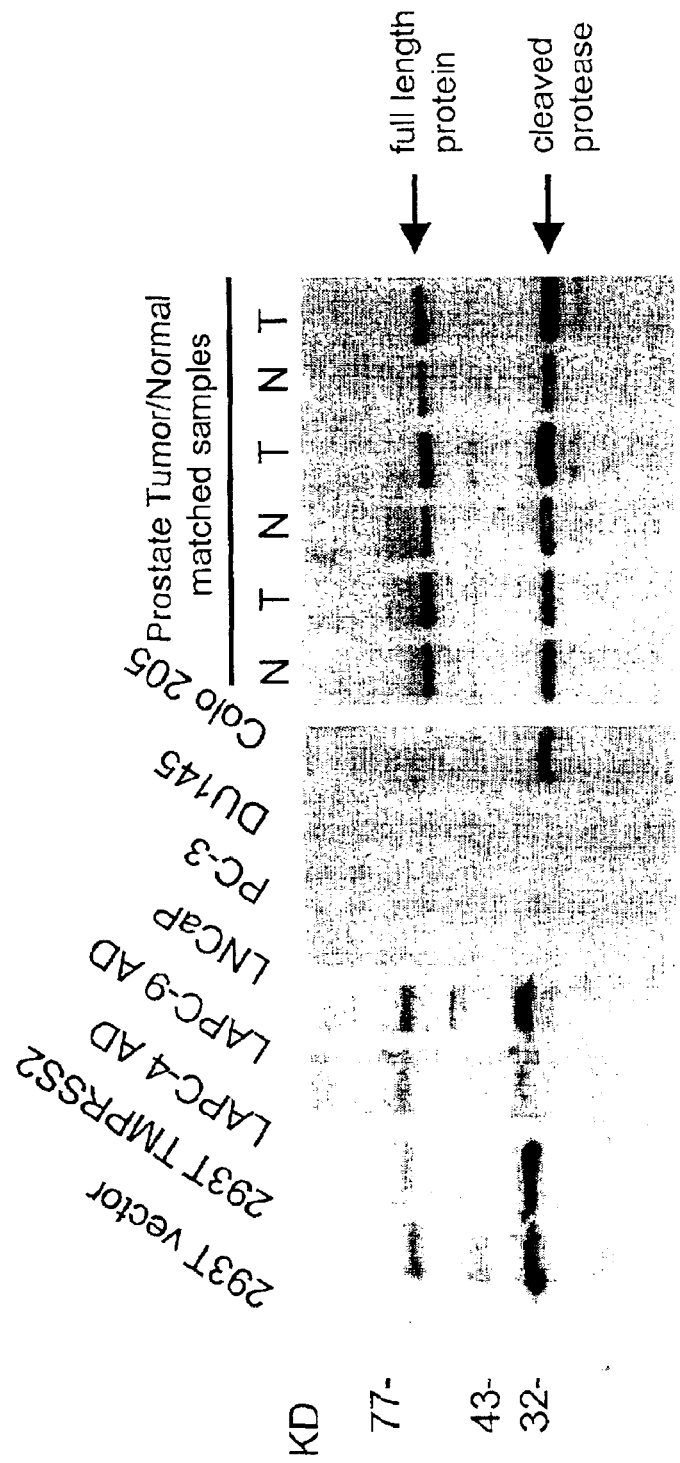
FIG. 15. 20P1F12/TMPRSS2 protein is expressed as a full length and proteolytically cleaved form in tissues and cell lines. Cell and tissue lysates (20 μg protein) were prepared in sample buffer and probed on western blots using the 1F9 anti-20P1F12/TMPRSS2 MAb. Prostate tumor tissues (T) with matched adjacent tissues (N) were derived from patients with Gleason scores of 7, 9 and 7 respectively. Lysate from 293T cells transfected either with control vector or with vector expressing 20P1F12/TMPRSS2 were used as negative and positive controls respectively.

Mouse MAbs were generated towards the protease domain of 20P1F12/TMPRSS2. Western blotting of protein extracts from 293T cells using the 1F9 MAb showed equal expression of two protein species with apparent molecular weights of 70 and 32 kilodaltons (kd) only in 20P1F12/TMPRSS2-transfected cells and not in control vector transfected cells (FIG. 15). The predicted molecular weight (MW) of 20P1F12/TMPRSS2 is 54 kd, suggesting that the 70 kd isoform is modified, possibly by glycosylation. The 20P1F12/TMPRSS2 protein sequence contains three possible N-linked linked glycosylation sites at residues 128, 213 and 249. Preliminary studies using endoglycosidase F treated 20P1F12/TMPRSS2 protein indicates that the protein is indeed glycosylated. The 32 kd form may be a proteolytically cleaved fragment containing the carboxyl-terminal epitopes recognized by the antibody.

Figure 14:
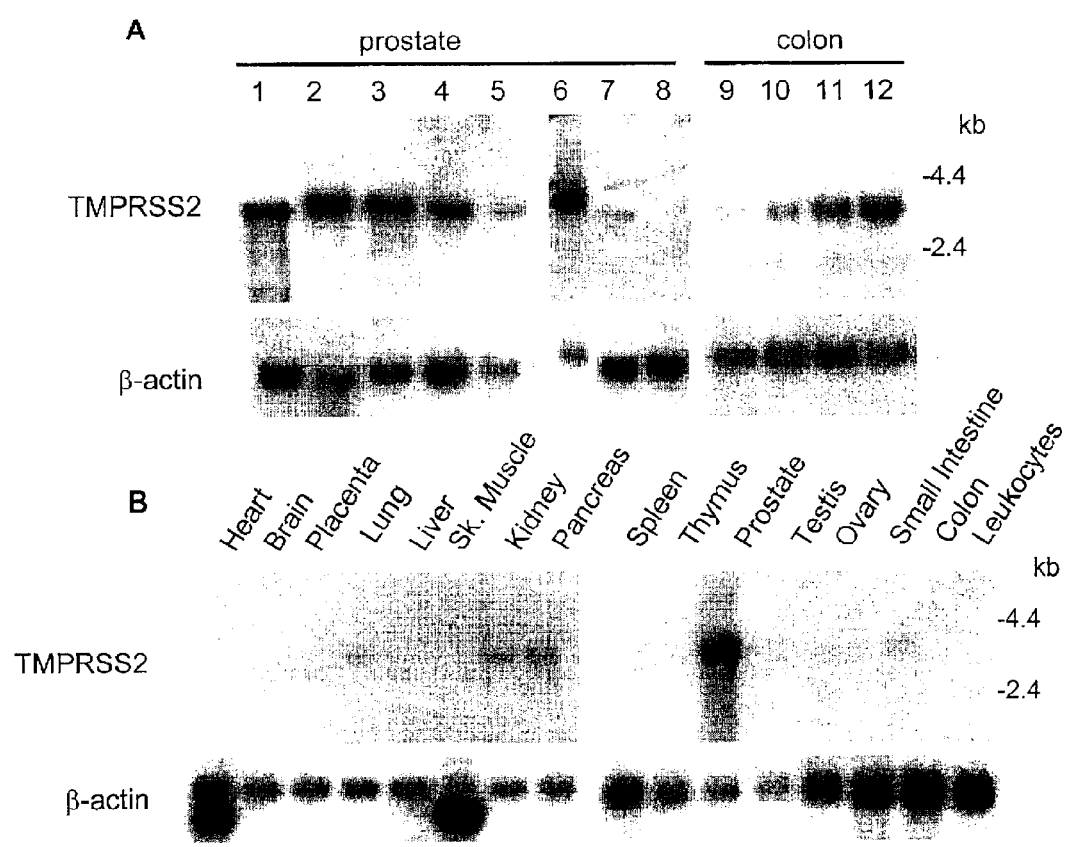
FIG. 14. High expression levels of 20P1F12/TMPRSS2 in prostate, prostate cancer and colon cancer cells. Northern blots containing RNA derived from normal tissues, prostate cancer xenografts and cell lines, and colon cancer cell lines were probed using a 20P1F12/TMPRSS2 cDNA fragment. The samples are 1. prostate, 2. LAPC-4 AD, 3. LAPC-4 AI, 4. LAPC-9 AD, 5. LAPC-9 AI, 6. LNCaP, 7. PC-3, 8. DU145, 9. CaCo-2, 10. LoVo, 11. T84, 12. Colo-205. All RNA samples were normalized with a β-actin probe. Size standards in kilobases (kb) are indicated on the side.

Analysis of human tissue and cell lines, which express varying levels of 20P1F12/TMPRSS2 by Northern blotting showed the same pattern of protein expression as in 20P1F12/TMPRSS2-transfected 293T cells. 20P1F12/TMPRSS2 expression was detected in protein lysates from LAPC-4 AD, LAPC-9 AD, and LNCaP cells, but not in the androgen independent PC-3 and DU145 cells. Analysis of three prostate cancer specimens with the matched normal adjacent tissue showed significant expression of 20P1F12/TMPRSS2 protein in all samples, including the normal prostate tissues. High expression was also detected in the colon cancer cell line Colo-205 (FIG. 14).

Interestingly, as shown in FIG. 23, in whole tissue lysate from the prostate of a normal 28 year oil male accident victim (panel C), the ratio between the 70 kD and 32 kD species of 20P1F12/TMPRSS2 appears to be different from that observed in the sera of individuals suffering from cancer (panel B), providing evidence that the induction of proteolysis may be correlated with the disease.

Example 7

20P1F12/TMPRSS2 Protein Expression is Dependent on the Androgen Receptor Signal

Figure 16:
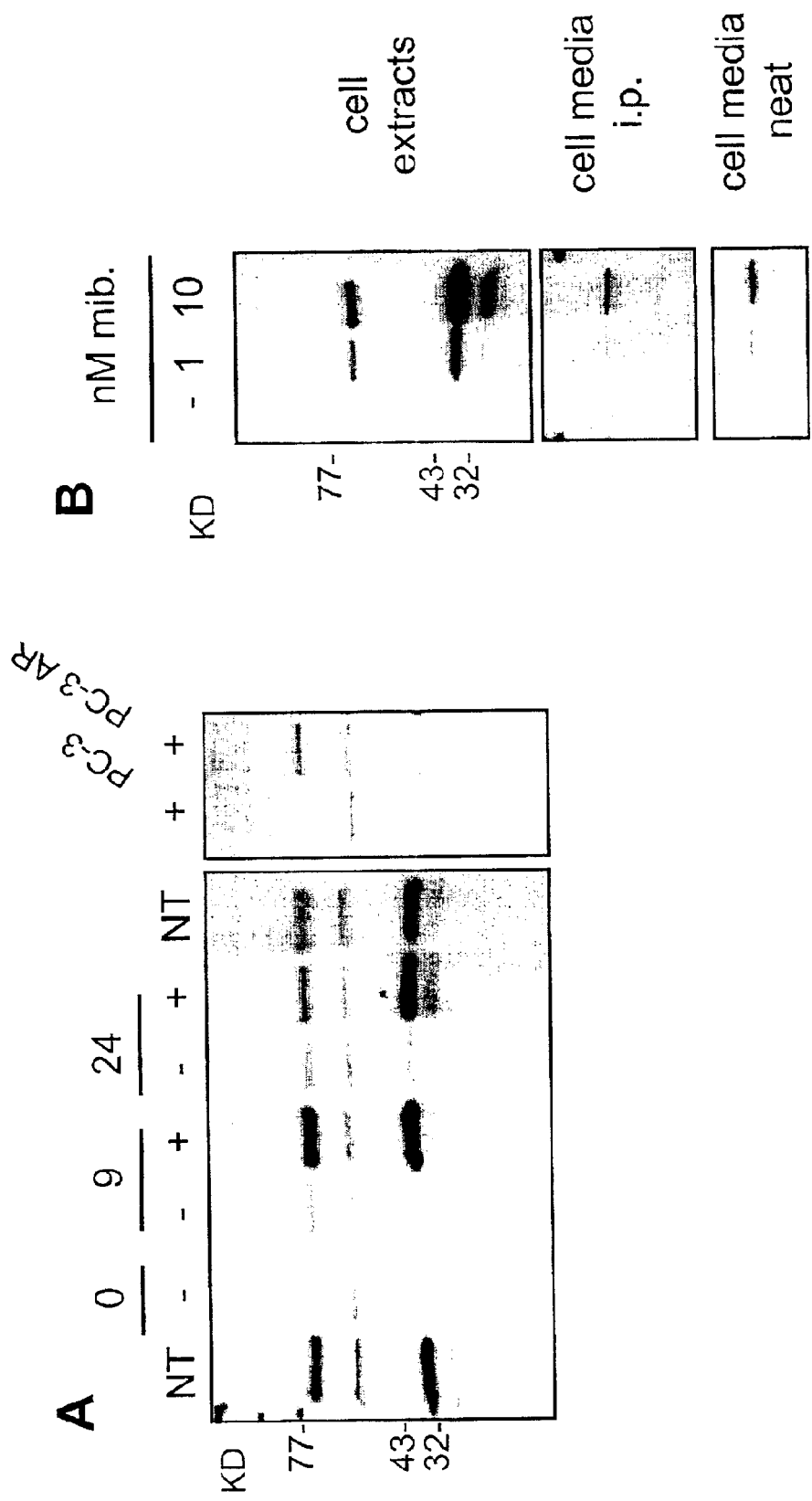
FIG. 16. 20P1F12/TMPRSS2 protease is androgen regulated and secreted into the media of prostate cancer cells. (A) LNCaP cells were grown in medium containing either 10% fetal bovine serum (NT) or in 2% charcoal-stripped serum (CSS) for 1 week. Cells growing in CSS were then left untreated (−) or were stimulated (+) with mibolerone (10 nM) for 9 or 24 hours. PC-3 cells and PC-3 cells expressing androgen receptor (AR) were stimulated with mibolerone for 9 hours. Lysates were probed with 1F9 MAb. (B) LNCaP cells were androgen deprived (−) and were then treated with either 1 nM or 10 nM mibolerone for 36 hours. Cell extracts and cell media were collected for anti-1F9 western blotting. The media was analyzed wither after immunoprecipitation (i.p.) with 1F9 MAb or neat (20 μl). Molecular weight standards are indicated on the side in kilodaltons (KD).

Our analysis shows that expression of 20P1F12/TMPRSS2 is lower in the androgen independent LAPC-9 xenograft and the androgen independent cells lines PC-3 and DU145, compared to the androgen dependent xenografts and cells lines. Castration of male mice harboring androgen dependent LAPC-9 tumors results in a dramatic decrease of 20P1F12/TMPRSS2 expression. To extend these findings, LNCaP cells, which are androgen dependent and express significant levels of 20P1F12/TMPRSS2, were deprived of androgen for one week. 20P1F12/TMPRSS2 protein expression in the androgen-deprived cells was compared to expression in cells treated with mibolerone. The results show that 20P1F12/TMPRSS2 expression was significantly reduced during androgen deprivation (FIG. 16A). Stimulation of androgen-deprived LNCaP cells with mibolerone for 9 and 24 hours resulted in an increase in 20P1F12/TMPRSS2 expression that is comparable to the levels seen in untreated LNCaP cells. PSA protein levels were measured in parallel, showing a similar regulation.

PC-3 cells, which do not normally express androgen receptor (Tilley et al., 1990, Cancer Res. 1990, 50:5382–5386) and grow in an androgen-independent manner, express little to no 20P1F12/TMPRSS2. However, PC-3 cells that have been engineered to express the wild-type androgen receptor exhibit low levels of 20P1F12/TMPRSS2 expression when treated with mibolerone (FIG. 16A). This indicates that 20P1F12/TMPRSS2 expression in prostate cancer cells is dependent on an androgen-receptor signal and restoration of this pathway in androgen independent prostate cancer cells re-activates expression of 20P1F12/TMPRSS2. PSA expression in PC-3 cells can also be induced by heterologous expression of androgen receptor and concomitant androgen stimulation (Dai et al., 1996, Steroids 61:531–539). These studies demonstrate that, similar to PSA, 20P1F12/TMPRSS2 protein is critically dependent on the androgen receptor pathway.

Example 8

20P1F12/TMPSS2 Protease is released into the Media of Prostate Cancer Cells

Structural predictions for 20P1F12/TMPRSS2 suggest that it is a type II transmembrane protein with a protease domain. The size of the cleaved 32 KD 20P1F12/TMPRSS2 fragment suggests that it contains the entire protease region. Cleavage of this domain is thus results in the release of the protease into the extracellular space. To test this hypothesis, media was collected from androgen-starved and androgen-stimulated LNCaP and LAPC4-cells. The media was then analyzed for the presence of 20P1F12/TMPRSS2 protein by immunoprecipitation and Western blotting using anti-20P1F12/TMPRSS2 MAb. The results show clear detection of cleaved 20P1F12/TMPRSS2 protein in the media of androgen-stimulated cells, but not in androgen-deprived cells (FIG. 16B). The amount of protease present in the media is directly correlated to the amount of 20P1F12/TMPRSS2 protein present in the cell extracts, which increases with an increased dose of mibolerone (FIG. 16B). Secreted 20P1F12/TMPRSS2 protease is also detected in the sera of mice that harbor LNCaP cells.

Example 9

29P1F12/TMRSS2 is Expressed in the Secretory Epithelia of Prostate and Colon Cancer Cells The expression of 20P1F12/TMPRSS2 in prostate cancer biopsies and surgical samples was examined by immunohistochemical analysis. Specific staining of 20P1F12/TMPRSS2 protein was validated using LNCaP cells that were androgen-deprived for one week and then were either left un-treated, or were stimulated with mibolerone for 9 hours. The cells were then fixed, embedded in paraffin and stained with the 1F9 anti-20P1F12/TMPRSS2 antibody. 20P1F12/TMPRSS2 staining of androgen-deprived LNCaP showed very little staining of the cells. In contrast, the majority of androgen-stimulated cells showed strong intracellular staining (FIG. 17A, B). LNCaP cells growing in regular media exhibited similar staining to androgen-stimulated cells. The majority of staining appeared localized to granular structures within the cell.

Analysis of 20 clinical specimens showed moderate to strong staining in the glandular epithelia of all normal prostate, PIN and prostate cancer samples tested (FIG. 17C and D, and Table 1 below). The signal appeared to be strongest at the apical side of the secretory cells, and in some cases granular staining was seen as was observed in LNCaP. The prostate tissue staining was specific, since GST-20P1F12/TMPRSS2 immunogen could competitively inhibit staining of prostate cancer tissue, while GST alone could not. Similar to PSA, 20P1F12/TMPRSS2 protein was found to accumulate within the lumen of the epithelial glands (FIG. 17E, F), indicating that 20P1F12/TMPRSS2 protein is secreted by the secretory epithelia.

No protein expression was detected in the basal cell layers of the normal prostate samples examined. This staining pattern is in contrast to the RNA in situ hybridization analysis, which showed expression of 20P1F12/TMPRSS2 RNA primarily in the basal cell layer of normal prostate glands (Lin et al., 1999).

Analysis of several non-prostate tissues showed no staining in most tissues (Table 1), including kidney and lung, which express some 20P1F12/TMPRSS2 message. Protein expression was detected in normal pancreas samples, normal colon tissues, and colon cancer tissues (Table 1). The pancreatic staining was restricted to the pyramidal exocrine acinar cells. No staining was detected in the islets of Langerhans. The staining in normal colon appeared primarily in the mucosal lining (FIG. 17G). The staining in colon cancer was generally more profound than in the normal colon tissues. Significant accumulation of 20P1F12/TMPRSS2 (as shown by staining with the antibody direct to the protease domain) was also detected in luminal areas (FIG. 17H), providing evidence of secretion of the antigen. Moreover, as illustrated for example in FIG. 17H, in cancer the tissue architecture is disrupted, which is likely to result in the leakage of 20P1F12/TMPRSS2 into the bloodstream in a manner analogous to PSA.

Example 10

20P1F12/TMPRSS2 Cleavage is a Consequence of Autocatalytic Activity

Single point mutants of 20P1F12/TMPRSS2 were generated using a two-step PCR method. Arginine residues 240, 252 and 255 were mutated to glutamines, and serine 441 was mutated to alanine. Using a full length cDNA clone as template, a 5'-20P1F12/TMPRSS2 PCR fragment was generated using one mutagenic primer (5'-GGCCCTCCAGCGTCACCC-3' (SEQ ID NO:18) for S441A mutant, 5'-CCGCAGGCTATACATTGTAAAGAAACC-3' (SEQ ID NO:19) for R240Q, 5'-TCCTGCTCTGTTGGCTTGAGTTCA-3' (SEQ ID NO:20) for R252Q and 5'-CCCACAATCTGGCTCTGGCG-3' (SEQ ID NO:21) for R255Q) and one 5'-specific 20P1F12/TMPRSS2 primer containing the start codon, a kozak sequence, and an EcoRI site for cloning (5'CGAATTCGCAAGATGGCTTTGAAC-3') (SEQ ID NO:22). The 3' fragment was generated by PCR using the reverse complement of the mutagenic primer (5'-GGGTGACGCTGGAGGGCC-3' (SEQ ID NO:23) for S441A, 5'-GGTTTCTTTACAATGTATAGCCTGCGG-3' (SEQ ID NO:24) for R240Q, 5'-TGAACTCAAGCCAACAGAGCAGGA-3' (SEQ ID NO:25) for R252Q mutant, and 5'-CGCCAGAGCCAGATTGTGGG-3' (SEQ ID NO:26) for R255Q) and a 3'-specific 20P1F12/TMPRSS2 primer containing the stop codon and a XbaI site for cloning (5'CGTCTAGATTAGCCGTCTGCCCTCA-3') (SEQ ID NO:27). For the second round of PCR, the 3' and 5' fragments were used as templates. The final PCR product was digested with EcoRI and XbaI, and cloned into pSRαMSV-tkNeo. Protein expression was analyzed after transfection into 293T cells.

20P1F12/TMPRSS2 is predominantly expressed as a 32 KD protein that is most likely the result of proteolytic cleavage. To determine if this cleavage is due to 20P1F12/TMPRSS2 catalytic activity, serine residue 441 of the catalytic triad in the protease domain was mutated to alanine (S441A). Mutant 20P1F12/TMPRSS2 cDNA was cloned into a retroviral vector for expression in 293 T cells. Western blot analysis of cell extracts of 293T cells transfected with either wild-type or S441A mutant 20P1F12/TMPRSS2 showed that in contrast to wild-type protein, 20P1F12/TMPRSS2 S441A appeared as a single protein species with an apparent molecular weight of 70 KD. Interestingly, 20P1F12/TMPRSS2 with a carboxyl-terminal myc-His tag also showed predominant expression of the full length tagged protein, although some cleavage product is detected. This suggests that the myc-His tag at the carboxyl-terminus of the protease domain exerts some inhibitory activity on the proteolytic cleavage (FIG. 18). These results of these experiments demonstrate that the proteolytic cleavage of 20P1F12/TMPRSS2 in cells and tissues is a consequence of auto-catalytic activity.

The protease domain of 20P1F12/TMPRSS2 belongs to the S1 family of serine proteases with cleavage activity after Arg or Lys residues. Examination of the protein sequence reveals the presence of three Arg residues (amino acids 240, 252, 255) near the amino-terminal region of the 20P1F12/TMPRSS2 protease domain. To identify the actual cleavage site of the protease domain, the three Arg residues were mutated to Gln residues. The mutants were expressed in 293T cells by transient transfection and were analyzed by Western blotting. Only the R255Q mutation resulted in a loss of autocatalytic cleavage, identifying the Arg 255-Ile 256 bond as the site of proteolytic cleavage.

Example 11

Observation of Distinct 20P1F12/TMPRSS2 Species in Different Biological Samples

To determine whether autocatalysis and generation of the 32 kD fragment of 20P1F12/TMPRSS2 protein may have biological and clinical relevance in prostate and colon cancer, 20P1F12/TMPRSS2 protein expression was monitored in human clinical colon and prostate cancer serum samples and in serum from mice bearing LNCaP prostate cancer xenografts. Immunoprecipitation/Western analysis of these serum samples with anti-20P1F12/TMPRSS2 1F9 mAb demonstrates expression of the 32 kD cleavage fragment, in LNCaP mouse serum and in prostate and colon cancer samples, but not in 2 normal male serum samples analyzed (FIGS. 23A and B). The band representing the 32 kD fragment in the human serum samples runs at a lower molecular weight than the fragment in LNCaP supernatants due to the predominant presence of human light chain immunoglobulin of the same molecular weight that carried over in the immunoprecipitation. The presence of 20P1F12/TMPRSS2 proteolytic fragment in cancer but not normal serum samples suggest that 20P1F12/TMPRSS2 may be a serum diagnostic marker for prostate and colon cancer. As is tissue culture supernatants of LNCaP cells, a 103 kD anti-20P1F12/TMPRSS2 immunoreactive complex was detected in serum samples in which the 32 kD fragment was expressed. The disclosure provided herein provides evidence that the 32 kD fragment encodes a biological active serine protease and that the 103 kD novel band may represent a complex of the 32 kD protease domain of 20P1F12/TMPRSS2 and a serine protease inhibitor (serpin). Such serum complexes are well described for the prostate specific kallikreins PSA and hK2 which each are present in serum both as the free form and in complexes with the serpin alpha-1-antichymotrypsin (See e.g. Grauer, L S, et al. Detection of human glandular kallidrein, hK2, as its precursor form and in complex with protease inhibitors in prostate carcinoma serum. J. Androl. 19:407–411, 1998; Christensson A et al Serum prostate specific antigen complexed to alpha 1-antichymotrypsin as an indicator of prostate cancer. J. Urol 150:100–105, 1993; Clements J A. The human kallikrein gene family: a diversity of expression and function. Mol. Cell. Endocrinol. 99:C1–C6, 1994). Interestingly, analysis of 20P1F12/TMPRSS2 expression in prostate tissue from a young normal male (28 years old) show predominant expression of full length 20P1F12/TMPRSS2 compared to samples from prostate cancer patients and cell lines (FIG. 23C). This observation provides evidence that the relative ratio of cleavage fragment to full length 20P1F12/TMPRSS2 may increase in diseased versus healthy prostate and colon tissue.

Due to the similarities of PSA and 20P1F12/TMPRSS2 being prostate-specific androgen regulated serine proteases, we investigated whether the natural function of 20P1F12/TMPRSS2, like PSA, as a secreted serine protease in seminal fluid. Western analysis of normal serminal plasma demonstrates high level expression of the 32 kD cleavage fragment of 20P1F12/TMPRSS2 as well as a slightly smaller 30 kD fragment (FIG. 24A). No detectable expression of full length 70 kD 20P1F12/TMPRSS2 protein is seen in seminal plasma as is seen in tissue lysates, however a novel higher molecular weight immunoreactive band of 90 kD is seen that may represent a covalent complex of 20P1F12/TMPRSS2 protease domain and a seminal plasma serpin. Immunoprecipitation/Western analysis of 20P1F12/TMPRSS2 in LNCaP supernatants and seminal fluid demonstrates expression of the 32 kD fragment in both, but distinct higher molecular complexes in serum containing supertants (103 kD) compared to seminal plasma (90 kD). PSA is found complexed with alpha-1-antichymotrypsin in serum but with protein C inhibitor in seminal plasma (Espana et al. Thromb. Res. 64:309–320, 1991; Christensson et al. Eur. J. Biochem. 220:45–53, 1994). A similar situation may exists for 20P1F12/TMPRSS2 in that the 103 kD serum band and 90 kD seminal plasma band represent complexes with distinct serpins and that the relative concentration of serpins in these fluids may govern complex formation. Interestingly, a lighter band of 90 kD is also seen in the LNCaP supernatant immunoprecipitation (FIG. 24B).

In addition, as shown in FIG. 26, a high level of expression of the 32 kD cleavage fragment of 20P1F12/TMPRSS2 is seen in colon cancer cell lines and colon cancer tissue samples as compared to normal colon tissue. Specifically, lysates of clinical specimens representing matched colon cancer tissue or normal adjacent tissue (left side of blot) and of colon cancer cell lines (right side of blot), and of LAPC4 and LAPC9 prostate cancer xenografts were subjected to anti-TMPRSS2 Western blot analysis using 1F9 mAb. Arrows indicate the position of the 32 kD auto-catalytic fragment and the 70 kD full length 20P1F12/TMPRSS2 protein. Higher expression of the 32 kD fragment is seen in the colon cancer tissue than in the matched normal adjacent tissue. As well, the predominant immunoreactive species present in colon cancer cell lines is also the 32 kD fragment. Interestingly, there is very little expression of full length 20P1F12/TMPRSS2 protein in the colon samples but there is strong expression of anti-TMPRSS2 immunoreactive bands of ~90 kD and ~50 kD in the colon tissues that may represent a complex of the 32 kD fragment.

Example 12

Methodologies to Determine the Potential of 20P1F12/TMPRSS2 as a Diagnostic and/or Therapeutic Target for Prostate and Colon Cancer A variety of methodologies well known in the art can be used to examine the potential of 20P1F12/TMPRSS2 as a diagnostic and/or therapeutic target for prostate and colon cancer and to characterize and quantitate 20P1F12/TMPRSS2 protein in clinical fluids of prostate and colon cancer patients. For example, one can further develop sensitive capture ELISA using existing panel of mAbs as described in Example 5 above (6 IgG1, 1 IgG2a). Such ELISA protocols can be found for example in Current Protocols In Molecular Biology, Unit 11, Frederick M. Ausubul et al. eds., 1995. Additionally, as illustrated above, one skilled in the art can analyze a spectrum of clinical samples to evaluate 20P1F12/TMPRSS2 expression and complex formation in different contexts using, for example a Western strategy. Such Western strategies are described for example in Current Protocols In Molecular Biology, Unit 10, Frederick M. Ausubul et al. eds., 1995. Additionally, one skilled in the art can determine the potential use of Abs to complex 20P1F12/TMPRSS2 binding partner (an a manner analogous to that observed with PSA and anti-serpin Abs) in ELISA development. Moreover, one can generate panels of mAbs to the protease domain as well as domains other than protease (SRCR, LCL, intracellular etc.).

In addition, a variety of methodologies well known in the art can be used to identify and characterize novel high molecular weight 20P1F12/TMPRSS2 immunoreactive bands in serum (103 kD) and semen (90 kD). For example, one skilled in the art can screen a known panel of molecules which are likely to interact with 20P1F12/TMPRSS2 (based on observations with like molecules such as PSA) such as serum and semen serpins to identify 20P1F12/TMPRSS2 complex formation. Such candidate molecules also include alpha-1-antichymotrypsin (PSA and hK2 complexes in serum), protein C inhibitor (PSA and hK2 complexes in semen), alpha-2-macroglobulin, alpha-1-antitrypsin, alpha-2-antiplasmin, anti-thrombin III and other serpins. Alternatively, one can isolate and sequence the binding partner using known protein purification (such as affinity columns etc.) and sequencing techniques.

In addition, a variety of methodologies well known in the art can be used to identify and characterize proteolytic activity and substrate specificity of 20P1F12/TMPRSS2. In particular, one can employ protease assays using purified or recombinant 20P1F12/TMPRSS2 (both the full length molecule as well as the protease domain fragment) to examine, for example, the effects of 20P1F12/TMPRSS2 polypeptides on in vitro and in vivo tumor growth. In addition, one can assay potential in vivo substrates (which may be natural targets in semen) such as semenogelin I and II (targeted by PSA and hK2), fibronectin (targeted by PSA and hK2), PSA (targeted by hK2), high molecular weight kininogen (targeted by hK1, hK2), the release of bradykinin, and autocatalysis. In addition, using techniques known in the art, fluorescent peptide substrates can be used to determine cleavage specificity.

In addition, a variety of methodologies well known in the art can be used to examine the in vivo and in vitro effects of anti-20P1F12/TMPRSS2 mAbs on tumor growth. For example, one can examine the effects of such molecules on tumor take and metastasis in SCID model (see e.g. Sato et al., Cancer Res. 1997 Apr 15;57(8):1584–9).

Alternatively, one can examine the effects of such molecules on proliferation/invasion/colony growth in vitro, using, for example, the matrigel assays described below and known in the art as providing models for cancer systems (see e.g. Bae et al., Breast Cancer Res. Tret. 24(3): 241–55 (1993)).

Example 13

Modulation of Invasion by 20P1F12/TMPRSS2

As disclosed in the data provided in this Example 20P1F12/TMPRSS2 is a protease which exhibits anti-invasive activities that are analogous to those observed with PSA.

To compare the invasive potential of tumor cells exposed to 20P1F12/TMPRSS2 in various contexts, these populations were assayed for their invasive potential using a Transwell Insert System (Becton Dickinson). Following manufacturers instructions, the cells were loaded with a fluorescent dye, namely calcein, and plated in the top well of the transwell insert. Invasion was then determined by measuring the fluorescence of cells in the lower chamber relative to the fluorescence of the entire cell population. All assays were performed in triplicate.

In these experiments, Becton Dickinson's technical bulletins describing invasion chambers and assay were relied upon in facilitating the performance of the described assays. Two relevant bulletins are (i) Technical Bulletin 427: an improved MATRIGEL Invasion Chamber and (ii) Technical bulletin 428: A Fluorescence Blocking Membrane Insert Enhances Analysis of Cell Motility Assays and information from both bulletins was used to optimize our assay system. Materials purchased were (i) the 8 micron FluoroBlock inserts and (ii) Matrigel. The inserts were coated with Matrigel, dried overnight and rehydrated for a minimum of 2 hours. Then, for example as shown in FIG. 27, parental and engineered PC3 cells were labeled with the fluorescent indicator, calcein, and incubated in the matrigel coated inserts. Invasion was detected by measuring the fluorescence of cells that migrated from the top chamber though the matrigel coated insert, into the bottom chamber. As a control for "total cell count" or "total invasion", cells were plated directly in the bottom chamber. Percent invasion was calculated by the following formula: (fluorescence of the cells that migrated to the bottom well/fluorescence of total cells)× 100. See also the procedures as discussed in Cancer Res. 1999 Dec 1;59(23):6010–4; Clin Exp Metastasis. 1998 Aug; 16(6):513–28 and J Urol. 2000 Mar; 163(3):985–92.

The in vitro matrigel assays utilized herein are well known models for studying cancer cell invasion that are recognized as correlating with the specific condition of the cancer cell invasion (e.g. the movement of prostate cancer cells from the prostate to the lymph nodes) that occurs in pathologies including prostate and colon cancer. Consequently this model provides a particularly useful tool for identifying the mechanisms involved in tumor and endothelial cell invasion of basement membranes and for the screening of anti-invasive agents (see e.g. Albini, Pathol. Oncol. Res. 1998, 4(3): pages 230–241; Hazan et al., J. Cell Biol. 2000 Feb. 21, 148(4):779–90 and Zing et al., Endocrinology 1999 Sep;140(9):4056–64). Consequently this system is widely used to assess therapeutic agents in large variety of cancers including prostate and colon cancers (see e.g. Festuccia et al., Clin. Exp. Metastasis 1998, 16(6): pages 513–528, Festuccia et al., Oncol. Res. 1999, 11(1): pages 17–31, Hiscox et al., Clin. Exp. Metastasis 1995, 13(5): pages 396–404 and Rao et al., J. Neurooncol. 1994, 18(2): pages 129–138).

In the results shown in FIGS. 27A–27C, parental PC3 cells and PC3 cells stably expressing 20P1F12/TMPRSS2 were assayed for their invasive potential using a Transwell Insert System (Becton Dickinson). The cells were loaded with a fluorescent dye, namely calcein, and plated in the top well of the transwell insert. Invasion was determined by measuring the fluorescence of cells in the lower chamber relative to the fluorescence of the entire cell population. The data in FIGS. 27A–27C show that cells expressing 20P1F12/TMPRSS2 have reduced invasive capabilities and provides evidence that 20P1F12/TMPRSS2 expression inhibits the invasion of tumors in vivo.

In the results shown in FIG. 28, 20P1F12/TMPRSS2 is shown to have proteolytic activity. In particular, purified recombinant GST-20P1F12/TMPRSS2 can cleave a universal substrate, namely casein in a dose dependent manner. Using a kit purchased from Molecular Probes, (EnzChek protease assay, catalog #E-6638) and following the manufacturer's protocol, purified recombinant GST-20P1F12/TMPRSS2 (aa255–492) was assayed for protease activity using fluorescein thiocarbamoyl-labeled (FTC) casein as a substrate (Molecular Probes). Different doses of GST-20P1F12/TMPRSS2 were incubated at 37° C. with FTC-casein for a total period of 6 hours. Fluorescence was real at 10 minutes intervals using a fluorometer. Cleavage of casein by 20P1F12/TMPRSS2 is detected by increased fluorescence. The assay was performed in triplicate and run over a period of 6 hours, with reading being performed every 10 minutes.

In the results shown in FIG. 29, the effects of purified recombinant 20P1F12/TMPRSS2 fusion protein on invasion are demonstrated. Calcein-loaded PC3 cells were plated in invasion chamber in media alone or in the presence of purified recombinant 20P1F12/TMPRSS2 fusion protein, i.e. GST-TMPRSS2 (aa 255–492). Purified GST was used as a control. Invasion was determined by measuring the fluorescence of cells in the lower chamber relative to the fluorescence of the entire cell population. The data in FIG. 29 demonstrates how the 20P1F12/TMPRSS2 protease fragment reduces the invasion of PC3 cells through the extracellular matrix and provides evidence that the protease domain of 20P1F12/TMPRSS2 can inhibit the formation of tumors in vivo.

In the results shown in FIG. 30, calcein-loaded PC3 cells were plated in invasion chamber in media alone or in the presence of 1ng/ml purified recombinant 20P1F12/TMPRSS2 fusion protein, i.e. GST-20P1F12/TMPRSS2 (aa 255–492). Control or anti-20P1F12/TMPRSS2 (1F9) mAb were added to the indicated samples. Invasion was determined by measuring the fluorescence of cells in the lower chamber relative to the fluorescence of the entire cell population. The assay was performed in triplicate. The data in FIG. 30 demonstrates how an anti-20P1F12/TMPRSS2 antibody can abrogate the invasion inhibiting activity of 20P1F12/TMPRSS2 and provides confirmatory evidence that this molecular can inhibit the formation of tumors in vivo.

Example 14

Effects of Antisense Oligonucleotides on 20P1F12/TMPRSS2 Expression

As noted in above, the skilled artisan can generate in vitro knock out cells and compare cells expressing or lacking the 20P1F12/TMPRSS2 protein in order to confirm the role of 20P1F12/TMPRSS2 in tumor progression, invasion and angiogenesis. As LNCaP cells endogenously express and secrete significant amounts of 20P1F12/TMPRSS2 protein, this line was selected as a experimental model for preliminary confirmatory studies using antisense morpholino oligonucleotides.

Figure 31:
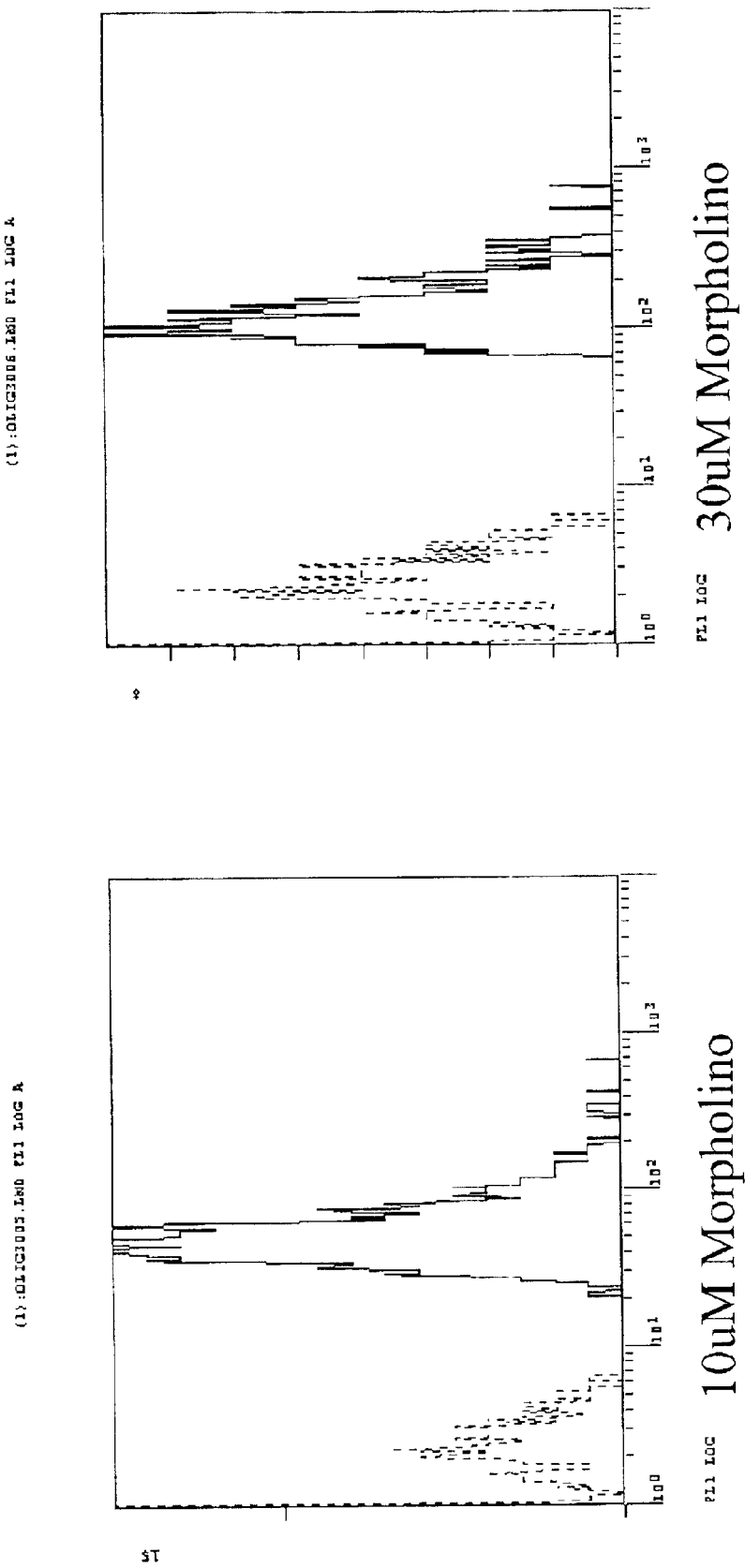
FIG. 31. 20P1F12/TMPRSS2 antisense oligonucleotides. LNCaP cells were scrape-loaded with either 10 or 30 μM of FITC-labeled morpholino oligonucleotide. The cells were grown for 24 hours and evaluated for fluorescence using flow cytometry. This histogram shows that 100% of cells exposed to morpholino oligonucleotides retain these oligonucleotides 24 hours post loading.
Figure 32:
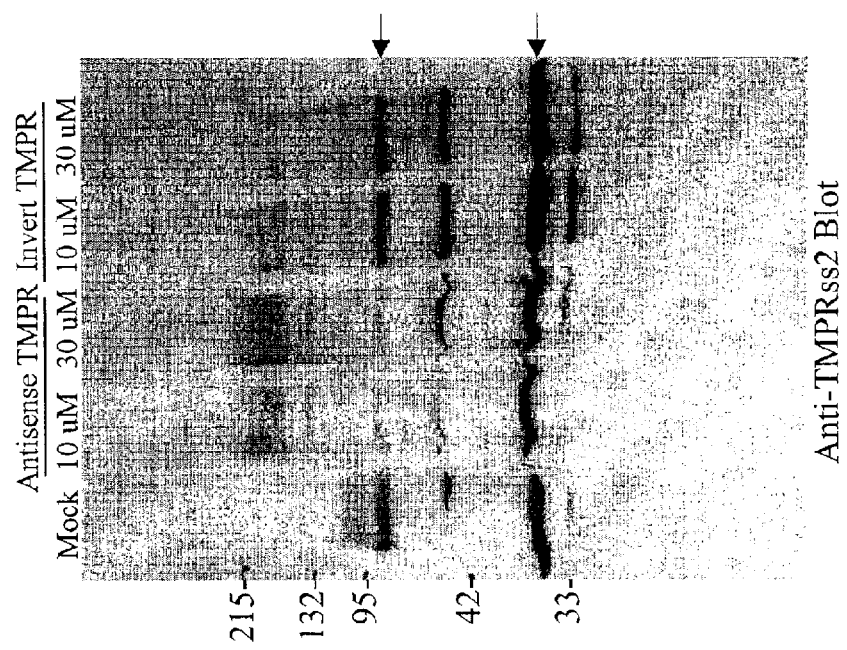
FIG. 32. 20P1F12/TMPRSS2 antisense oligonucleotides decrease 20P1F12/TMPRSS2 protein levels. LNCaP cells were scrape-loaded with either 10 or 30 μM morpholino oligonucleotides. The cells were grown for 48 hours and evaluated for 20P1F12/TMPRSS2 expression by western blotting using the anti-TMPRSS2 1F9 antibody. 20P1F12/TMPRSS2 antisense oligonucleotides specifically decrease expression of the full length 20P1F12/TMPRSS2 in LNCaP cells (lanes 3 and 4).

In a first confirmatory study, we demonstrate that 100% of cells exposed to morpholino oligonucleotides retain these oligonucleotides 24 hours post loading (FIG. 31). In a second confirmatory study, we demonstrate the ability to specifically eliminate expression of the full length 20P1F12/TMPRSS2 in LNCaP cells using these antisense morpholino oligonucleotides (FIG. 32, lanes 3 and 4).

This in vitro KO system enables one to directly compare antisense KO and parental LNCaP cells using functional assays, and confirm results generated using other model systems. In particular, parental and antisense 20P1F12/TMPRSS2 KO LNCaP cells may be compared using the well described transwell system for their ability to invade matrigel. In parallel, these cells can be compared for their ability to form tumors in SCID mice. They can also be evaluated using an in vitro angiogenesis assay measuring endothelial cell proliferation and tube formation.

TABLE 1

Immunohistochemical staining of human tissues with anti-TMPRSS2 monoclonal antibody

| | | Predominant Staining Localization | |
|---|---|---|---|
| Staining Intensity | Tissue | Cytoplasmic | Luminal surface/secretion |
| None | Kidney | | |
| | Skin | | |
| | Lung | | |
| | Liver | | |
| | Testis | | |
| | Spleen | | |
| Light | Fallopian tubes | + | |
| | Colon cancer (1/4) | + | + |
| Moderate to strong | Prostate (7/7) | + | + |
| | BPH (7/7) | + | + |
| | PIN (1/1) | + | + |
| | Colon (4/4) | + | |
| | Pancreas (4/4) | + | |
| | Prostate cancer (5/5) | + | + |
| | Colon cancer (3/3) | + | + |

TABLE 2

Epitope mapping of anti-TMPRSS2 mAbs

| test mAb | competitor mAb | | | | | | | |
|---|---|---|---|---|---|---|---|---|
| | none | 1F9 | 2D10 | 2F8 | 3G3 | 6B11 | 8C6 | 9G8 |
| 1F9-B | 2.371 ± 0.012 | 0.269 ± 0.001 | 0.730 ± 0.004 | 2.230 ± 0.037 | 0.359 ± 0.005 | 0.353 ± 0.008 | 2.625 ± 0.033 | 2.183 ± 0.105 |
| 2F8-B | 1.390 ± 0.015 | 1.258 ± 0.020 | 1.169 ± 0.005 | 0.407 ± 0.032 | 1.250 ± 0.009 | 1.242 ± 0.020 | 0.371 ± 0.005 | 0.611 ± 0.039 |
| 8C6-B | 1.512 ± 0.004 | 1.899 ± 0.013 | 1.434 ± 0.031 | 1.216 ± 0.062 | 1.803 ± 0.044 | 1.806 ± 0.056 | 0.161 ± 0.005 | 1.473 ± 0.014 |

A decrease in signal intensity of the biotinylated antibody in the presence of an excess of unlabelled antibody indicates that the mAbs compete for the same or overlapping binding sites (shown in bold). As indicated in Table 2 a decrease in signal intensity of biotinylated 1F9 (1F9-B) is seen in the presence of mAbs 2D10, 3G3, and 6B11, and itself, but not by 2F8, 8C6, and 9G8. These results indicate that mAbs 1F9, 2D10, 3G3, 6B11 share the same (or overlapping) epitope that is distinct from those of 2F8, 8C6, and 9G8. MAb 2F8-B is competed by itself and by mAbs 8C6 and 9G8 indicating these mAbs share the same or overlapping epitopes. MAb 8C6-B is competed by itself and moderately by mAb 2F8. Taken together, these results indicate that the panel of anti-TMPRSS2 antibodies recognize different epitopes within the protease domain of TMPRSS2.

Throughout this application, various publications are referenced within parentheses. The disclosures of these publications are thereby incorporated by reference herein in their entireties.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. A method of identifying evidence of a neoplasm in a biological sample comprising:
   (a) examining a level of expression of 20P1F12/TMPRSS2 gene, which encodes the protein of SEQ. ID. NO:2 (FIG. 1), in a test biological sample; and
   (b) comparing the level of said 20P1F12/TMPRSS2 gene expression in the test biological sample to a level of said 20P1F12/TMPRSS2 gene expression found in a comparable normal biological sample,
   wherein an enhanced level of 20P1G12/TMPRSS2 gene expression in the test biological sample relative to the normal biological sample is evidence of a neoplasm, and
   wherein the neoplasm is a prostate cancer.

2. The method according to claim 1, wherein the level of 20P1F12/TMPRSS2 gene expression in the test biological sample is evaluated by examining the level of 20P1F12/TMPRSS2 protein.

3. The method of claim 2, wherein the level of 20P1F12/TMPSS2 protein is evaluated by an immunoassay by contacting the sample with an antibody or antibody fragment which is immunoreactive with said protein and observing the presence or absence of an immunocomplex formed from the antibody or fragment with any 20P1F12/TMPRSS2 protein.

4. A method of identifying evidence of a neoplasm in a biological sample comprising:
   (a) examining a level of expression of 20P1F12/TMPRSS2 gene, which encodes the protein of SEQ. ID. NO:2 (FIG. 1), in a test biological sample; and
   (b) comparing the level of said 20P1F12/TMPRSS2 gene expression in the test biological sample to a level of said 20P1F12/TMPRSS2 gene expression found in a comparable normal biological sample,
   wherein an enhanced level of 20P1F12/TMPRSS2 gene expression in the test biological sample relative to the normal biological sample is evidence of a neoplasm,
   wherein the 20P1F12/TMPRSS2 evaluated in the test biological sample is secreted from neoplastic cells, and
   wherein the neoplastic cells are prostate cancer cells.

5. The method according to claim 4, wherein the level of 20P1F12/TMPRSS2 gene expression in the test biological sample is evaluated by examining the level of 20P1F12/TMPRSS2 protein.

6. The method of claim 5, wherein the level of 20P1F12/TMPRSS2 protein is evaluated by an immunoassay by contacting the sample with an antibody or antibody fragment which is immunoreactive with said protein and observing the presence or absence of an immunocomplex formed from the antibody or fragment with 20P1F12/TMPRSS2 protein.

7. A method of identifying evidence of a neoplasm in a biological sample comprising:
   (a) examining a level of expression of 20P1F12/TMPRSS2 gene, which encodes the protein encoded by a cDNA clone 20P1F12-GTC1 contained in the plasmid deposited with the American Type Culture Collection (ATCC) as Accession No. 207097, in a test biological sample; and
   (b) comparing the level of said 20P1F12/TMPRSS2 gene expression in the test biological sample to a level of said 20P1F12/TMPRSS2 gene expression found in a comparable normal biological sample;
   wherein an enhanced level of 20P1F12/TMPRSS2 gene expression in the test biological sample relative to the normal biological sample is evidence of a neoplasm; and
   wherein the neoplasm is a prostate cancer.

8. The method according to claim 7, wherein the level of 20P1F12/TMPRSS2 gene expression in the test biological sample is evaluated by examining the level of 20P1F12/TMPRSS2 protein.

9. The method of claim 8, wherein the level of 20P1F12/TMPRSS2 protein is evaluated by an immunoassay by contacting the sample with an antibody or antibody fragment which is immunoreactive with said protein and observing the presence or absence of an immunocomplex formed from the antibody or fragment with 20P1F12/TMPRSS2 protein.

10. The method of claim 8, wherein the 20P1F12/TMPRSS2 protein is secreted from prostate cancer cells.

* * * * *